(12) United States Patent
Parker et al.

(10) Patent No.: US 12,011,373 B2
(45) Date of Patent: Jun. 18, 2024

(54) MOUNTING BRACKET FOR CONNECTING A PROSTHETIC LIMB TO A PROSTHETIC FOOT

(71) Applicant: Proteor USA, LLC, Tempe, AZ (US)

(72) Inventors: Gene Parker, San Tan Valley, AZ (US); James M. Scott, Hartford, CT (US); Brian Werner, Mesa, AZ (US); Keith B. Smith, Yorba Linda, CA (US); Kodi Nixon, Mesa, AZ (US); Steven D. Liddiard, Mayfield, UT (US)

(73) Assignee: Proteor USA, LLC, Tempe, AZ (US)

( * ) Notice: Subject to any disclaimer, the term of this patent is extended or adjusted under 35 U.S.C. 154(b) by 437 days.

(21) Appl. No.: 17/350,621

(22) Filed: Jun. 17, 2021

(65) Prior Publication Data

US 2021/0307937 A1    Oct. 7, 2021

Related U.S. Application Data

(63) Continuation-in-part of application No. 16/281,278, filed on Feb. 21, 2019, now abandoned, which is a
(Continued)

(51) Int. Cl.
*A61F 2/66* (2006.01)
*A61F 2/50* (2006.01)

(52) U.S. Cl.
CPC ........ *A61F 2/66* (2013.01); *A61F 2002/5009* (2013.01); *A61F 2002/6614* (2013.01);
(Continued)

(58) Field of Classification Search
CPC ........................................................ A61F 2/66
See application file for complete search history.

(56) References Cited

U.S. PATENT DOCUMENTS

| 4,578,082 A | 3/1986 | Sen-Jang |
| 4,822,363 A | 4/1989 | Phillips |

(Continued)

FOREIGN PATENT DOCUMENTS

| CA | 2054588 | 5/1999 |
| CN | 2089799 U | 8/1990 |

(Continued)

OTHER PUBLICATIONS

Roland D. Christensen, U.S. Appl. No. 09/607,494 for "Prosthetic Foot," filed Jun. 30, 2000, abandoned Oct. 29, 2002.
(Continued)

*Primary Examiner* — Jacqueline Woznicki
(74) *Attorney, Agent, or Firm* — Noblitt & Newson, PLLC

(57) ABSTRACT

A mounting bracket for a prosthetic foot configured to attach to a residual limb, comprising an upper member, a lower member and compression torsion joint. The upper member comprises an upper flange, a mating post, and mounting portion configured to attach to the residual limb. The lower member comprises a mating portion, a lower flange, and a mounting portion configured to attach to the prosthetic foot. The compression torsion joint couples the upper member to the lower member and is configured to limit the vertical movement and torsional movement of the upper member with respect to the lower member.

19 Claims, 81 Drawing Sheets

SECTION H-H

Related U.S. Application Data continuation-in-part of application No. 15/726,712, filed on Oct. 6, 2017, now Pat. No. 10,405,998, application No. 17/350,621, filed on Jun. 17, 2021 is a continuation-in-part of application No. 14/976,129, filed on Dec. 21, 2015, now abandoned, application No. 17/350,621, filed on Jun. 17, 2021 is a continuation-in-part of application No. 15/726,712, filed on Oct. 6, 2017, now Pat. No. 10,405,998, which is a continuation-in-part of application No. 14/976,129, filed on Dec. 21, 2015, now abandoned, which is a continuation of application No. 14/731,818, filed on Jun. 5, 2015, now abandoned, which is a continuation of application No. 13/568,535, filed on Aug. 7, 2012, now abandoned, which is a continuation-in-part of application No. PCT/US2011/033319, filed on Apr. 20, 2011, which is a continuation-in-part of application No. 12/799,215, filed on Apr. 20, 2010, now abandoned, which is a continuation-in-part of application No. 11/901,845, filed on Sep. 19, 2007, now Pat. No. 8,048,173, application No. 17/350,621, filed on Jun. 17, 2021 is a continuation-in-part of application No. 14/731,771, filed on Jun. 5, 2015, now abandoned, which is a continuation of application No. 13/642,501, filed as application No. PCT/US2011/033319 on Apr. 20, 2011, now Pat. No. 9,078,773.

(60) Provisional application No. 63/078,748, filed on Sep. 15, 2020, provisional application No. 63/137,970, filed on Jan. 15, 2021, provisional application No. 62/539,743, filed on Aug. 1, 2017, provisional application No. 62/451,870, filed on Jan. 30, 2017, provisional application No. 62/407,954, filed on Oct. 13, 2016.

(52) U.S. Cl.
CPC ............... *A61F 2002/6642* (2013.01); *A61F 2002/6664* (2013.01)

(56) References Cited

U.S. PATENT DOCUMENTS

| | | | |
|---|---|---|---|
| 5,062,859 A | 11/1991 | Naeder | |
| 5,112,356 A | 5/1992 | Harris et al. | |
| 5,116,382 A | 5/1992 | Wilson et al. | |
| 5,156,632 A | 10/1992 | Wellershaus | |
| 5,258,038 A | 11/1993 | Robinson et al. | |
| 5,258,039 A | 11/1993 | Goh et al. | |
| 5,352,189 A | 10/1994 | Schumann et al. | |
| 5,443,522 A | 8/1995 | Hiemisch | |
| 5,458,656 A | 10/1995 | Phillips | |
| 5,443,528 A | 11/1995 | Allen | |
| 5,514,186 A | 5/1996 | Phillips | |
| 5,571,213 A | 11/1996 | Allen | |
| 5,653,767 A | 8/1997 | Allen | |
| 5,701,686 A | 12/1997 | Herr | |
| 5,766,265 A | 6/1998 | Phillips | |
| 5,888,239 A | 3/1999 | Wellershaus et al. | |
| 5,897,594 A | 4/1999 | Martin et al. | |
| 5,944,760 A | 8/1999 | Christensen | |
| 5,954,075 A | 9/1999 | Gilmour | |
| 5,993,488 A | 11/1999 | Phillips | |
| 6,077,301 A | 6/2000 | Pusch | |
| 6,099,572 A | 8/2000 | Mosler et al. | |
| 6,120,547 A | 9/2000 | Christensen | |
| 6,197,068 B1 | 3/2001 | Christensen | |
| 6,214,056 B1* | 4/2001 | Wilkinson | A61F 2/7812 623/35 |
| 6,241,776 B1 | 6/2001 | Christensen | |
| 6,261,324 B1 | 7/2001 | Merlette | |
| 6,406,500 B1 | 6/2002 | Phillips | |
| 6,468,315 B1 | 10/2002 | Wilkinson et al. | |
| 6,511,512 B2 | 1/2003 | Phillips et al. | |
| 6,663,673 B2 | 12/2003 | Christensen | |
| 6,669,737 B2 | 12/2003 | Mosler et al. | |
| 6,682,569 B2 | 1/2004 | Wilkinson et al. | |
| 6,702,858 B2 | 3/2004 | Christensen | |
| 6,712,860 B2 | 3/2004 | Rubie et al. | |
| 6,764,522 B1 | 7/2004 | Cehn | |
| 6,767,370 B1 | 7/2004 | Mosler et al. | |
| 6,805,717 B2 | 10/2004 | Christensen | |
| 6,811,571 B1 | 11/2004 | Phillips | |
| 6,827,343 B2 | 12/2004 | Skiera | |
| 6,852,131 B1 | 2/2005 | Chen et al. | |
| 6,875,241 B2 | 4/2005 | Christensen | |
| 6,875,242 B2 | 4/2005 | Christensen | |
| 6,911,052 B2 | 6/2005 | Christensen | |
| 6,929,665 B2 | 8/2005 | Christensen | |
| 6,942,704 B2 | 9/2005 | Sulprizio | |
| 6,966,933 B2 | 11/2005 | Christensen | |
| 6,972,043 B1 | 12/2005 | Biedermann et al. | |
| 7,063,727 B2 | 6/2006 | Phillips et al. | |
| 7,172,630 B2 | 2/2007 | Christensen | |
| 7,178,218 B1 | 2/2007 | Houser et al. | |
| 7,341,603 B2 | 3/2008 | Christensen | |
| 7,419,509 B2 | 9/2008 | Christensen | |
| 7,462,201 B2 | 12/2008 | Christensen | |
| 7,520,904 B2 | 4/2009 | Christensen | |
| 7,572,299 B2 | 8/2009 | Christensen | |
| 7,578,852 B2 | 8/2009 | Townsend et al. | |
| 7,618,464 B2 | 11/2009 | Christensen | |
| 7,655,050 B2 | 2/2010 | Palmer | |
| 7,686,848 B2 | 3/2010 | Christensen | |
| 7,727,285 B2 | 6/2010 | Christensen | |
| 7,740,602 B2 | 6/2010 | Christensen | |
| 7,771,488 B2 | 8/2010 | Asgeirsson et al. | |
| 7,794,506 B2 | 9/2010 | Christensen | |
| 7,824,446 B2 | 11/2010 | Christensen et al. | |
| 7,846,213 B2 | 12/2010 | Lecomte et al. | |
| 7,951,101 B2 | 5/2011 | Pusch | |
| 7,955,399 B2 | 6/2011 | Townsend et al. | |
| 8,007,544 B2 | 8/2011 | Jonsson et al. | |
| 8,034,121 B2 | 10/2011 | Christensen | |
| 8,070,828 B2 | 12/2011 | Shannon | |
| 8,092,550 B2 | 1/2012 | McCarvill et al. | |
| 8,202,325 B2 | 6/2012 | Albrecht-Laatsch et al. | |
| 8,246,695 B2 | 8/2012 | Mosler | |
| 8,317,877 B2 | 11/2012 | Doddroe et al. | |
| 8,474,329 B2 | 7/2013 | Schulze et al. | |
| 8,500,825 B2 | 8/2013 | Christensen et al. | |
| 8,568,489 B2 | 10/2013 | Finlinson et al. | |
| 8,628,585 B2 | 1/2014 | Harris et al. | |
| 8,771,370 B2 | 7/2014 | Albrecht-Laatsch et al. | |
| 8,771,372 B1 | 7/2014 | Rubie | |
| 8,900,326 B2 | 12/2014 | Doddroe et al. | |
| 8,945,238 B2 | 2/2015 | Mosler et al. | |
| 9,161,846 B2 | 10/2015 | Mosler | |
| 9,265,626 B1 | 2/2016 | Lecomte et al. | |
| 9,351,853 B2 | 5/2016 | Doddroe et al. | |
| 9,486,331 B2 | 11/2016 | Friesen et al. | |
| 10,342,680 B2 | 7/2019 | Nijman et al. | |
| 10,485,682 B2 | 11/2019 | Herr et al. | |
| 2002/0013628 A1 | 1/2002 | Harris | |
| 2002/0040249 A1 | 4/2002 | Phillips | |
| 2002/0133237 A1 | 9/2002 | Christensen | |
| 2002/0188355 A1 | 12/2002 | Chen | |
| 2003/0109638 A1 | 6/2003 | Briggs et al. | |
| 2004/0225375 A1 | 11/2004 | Chen | |
| 2004/0236435 A1 | 11/2004 | Chen | |
| 2005/0033450 A1 | 2/2005 | Christensen | |
| 2005/0033451 A1 | 2/2005 | Aigner et al. | |
| 2005/0038525 A1 | 2/2005 | Doddroe | |
| 2005/0071017 A1 | 3/2005 | LeComte et al. | |
| 2005/0187640 A1 | 8/2005 | Christensen | |
| 2005/0203640 A1 | 9/2005 | Christensen | |
| 2005/0216098 A1 | 9/2005 | Christensen | |
| 2005/0261783 A1* | 11/2005 | Geilman | A61F 2/60 267/140.2 |
| 2005/0267601 A1 | 12/2005 | Chen | |

(56) References Cited

U.S. PATENT DOCUMENTS

| | | |
|---|---|---|
| 2006/0069450 A1 | 3/2006 | McCarvil et al. |
| 2006/0167563 A1 | 7/2006 | Johnson et al. |
| 2006/0212131 A1 | 9/2006 | Curtis |
| 2006/0224246 A1 | 10/2006 | Clausen |
| 2006/0241782 A1 | 10/2006 | Curtis |
| 2006/0241783 A1 | 10/2006 | Christensen |
| 2007/0100466 A1 | 5/2007 | Allert |
| 2008/0033578 A1 | 2/2008 | Christensen |
| 2008/0167730 A1 | 7/2008 | Pusch |
| 2008/0188951 A1 | 8/2008 | Christensen et al. |
| 2008/0228288 A1 | 9/2008 | Nelson et al. |
| 2008/0312752 A1 | 12/2008 | Miller |
| 2009/0076626 A1 | 3/2009 | Ochoa |
| 2009/0105845 A1 | 4/2009 | Curtis |
| 2009/0157197 A1 | 6/2009 | Bonacini |
| 2009/0204229 A1 | 8/2009 | Mosler et al. |
| 2009/0204231 A1 | 8/2009 | Bonacini |
| 2010/0004757 A1 | 1/2010 | Clausen et al. |
| 2010/0042228 A1 | 2/2010 | Doddroe et al. |
| 2011/0009982 A1 | 1/2011 | King et al. |
| 2011/0029097 A1 | 2/2011 | Ochoa |
| 2011/0197682 A1 | 8/2011 | Palmer |
| 2011/0199101 A1 | 8/2011 | Steele |
| 2011/0202144 A1 | 8/2011 | Palmer |
| 2011/0208322 A1 | 8/2011 | Rifkin et al. |
| 2011/0320012 A1 | 12/2011 | Christensen et al. |
| 2012/0046760 A1 | 2/2012 | Nissels et al. |
| 2012/0179274 A1 | 7/2012 | Christensen |
| 2012/0205206 A1 | 8/2012 | Chen et al. |
| 2012/0209406 A1 | 8/2012 | Chen et al. |
| 2012/0271434 A1 | 10/2012 | Friesen et al. |
| 2013/0030549 A1 | 1/2013 | Zahedi |
| 2013/0066439 A1 | 3/2013 | Zamora et al. |
| 2013/0173023 A1 | 7/2013 | Lecomte et al. |
| 2013/0289742 A1 | 10/2013 | Halldorsson et al. |
| 2014/0018938 A1 | 1/2014 | Bertels et al. |
| 2014/0046456 A1 | 2/2014 | Smith et al. |
| 2014/0156027 A1 | 6/2014 | Smith et al. |
| 2014/0243997 A1 | 8/2014 | Clausen et al. |
| 2014/0336782 A1 | 11/2014 | Mosler et al. |
| 2015/0134081 A1 | 5/2015 | Geiger et al. |
| 2015/0282953 A1 | 10/2015 | Smith et al. |
| 2015/0289996 A1 | 10/2015 | Smith |
| 2016/0038311 A1 | 2/2016 | Gonzalez et al. |
| 2016/0158030 A1 | 6/2016 | Doddroe et al. |
| 2018/0042737 A1* | 2/2018 | Smith ................. A61F 2/66 |
| 2019/0192314 A1 | 6/2019 | Parker et al. |
| 2020/0179139 A1* | 6/2020 | Kaltenborn .......... A61F 2/66 |

FOREIGN PATENT DOCUMENTS

| | | |
|---|---|---|
| CN | 2075074 U | 9/1990 |
| CN | 2178511 U | 12/1993 |
| CN | 2614649 Y | 5/2004 |
| CN | 2614650 Y | 5/2004 |
| CN | 2614651 Y | 5/2004 |
| CN | 201524155 U | 7/2010 |
| CN | 101621973 A | 12/2011 |
| CN | 102665614 A | 3/2016 |
| DE | 20307200 U1 | 6/2003 |
| DE | 20307948 U1 | 7/2003 |
| DE | 20307949 U1 | 7/2003 |
| DE | 102014006571 B3 | 8/2015 |
| DE | 102014006687 A1 | 11/2015 |
| EP | 0401864 B1 | 11/1992 |
| EP | 1395209 B1 | 6/2010 |
| IN | 201841014821 A | 4/2018 |
| JP | 5126919 B1 | 1/2013 |
| RU | 2473323 C2 | 8/2010 |
| TW | 229414 | 11/1993 |
| TW | 339646 | 9/1998 |
| TW | 340371 | 9/1998 |
| TW | 353939 | 3/1999 |
| TW | 382260 | 2/2000 |
| TW | M253331 | 12/2004 |
| TW | M291283 | 6/2006 |
| TW | M336777 U | 7/2008 |
| TW | D124156 | 8/2008 |
| TW | D124157 | 8/2008 |
| TW | M377969 U | 4/2010 |
| TW | M409061 U | 8/2011 |
| TW | M438897 U | 10/2012 |
| TW | M438898 U | 10/2012 |
| TW | M450362 U | 4/2013 |
| TW | M467446 U | 12/2013 |
| TW | M484416 U | 8/2014 |
| WO | 93/24080 A1 | 12/1993 |
| WO | 2005027802 A1 | 3/2005 |
| WO | 2006099580 A2 | 9/2006 |
| WO | 2008070177 A1 | 6/2008 |
| WO | 2011133717 A1 | 10/2011 |
| WO | 2012005856 A1 | 1/2012 |
| WO | 2012009319 A2 | 1/2012 |
| WO | 2013101848 A1 | 7/2013 |
| WO | 2014008306 A1 | 1/2014 |
| WO | 2014147070 A1 | 9/2014 |
| WO | 2015169443 A1 | 11/2015 |

OTHER PUBLICATIONS

Moloney et al., "Parameters determining the strength and toughness of particulate filled epoxide resins," Journal of Materials Science, Feb. 1, 1987, pp. 381-393.

* cited by examiner

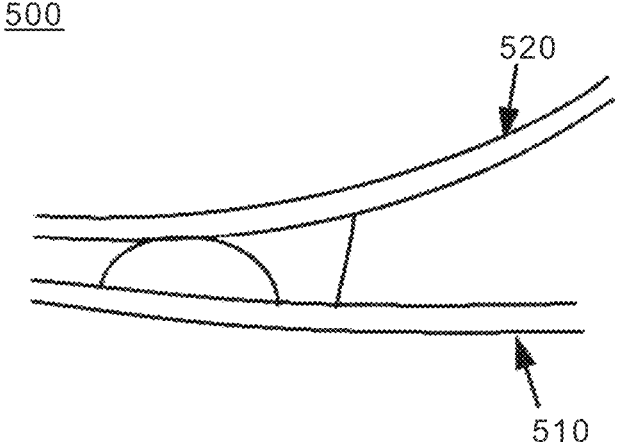
Fig. 5A
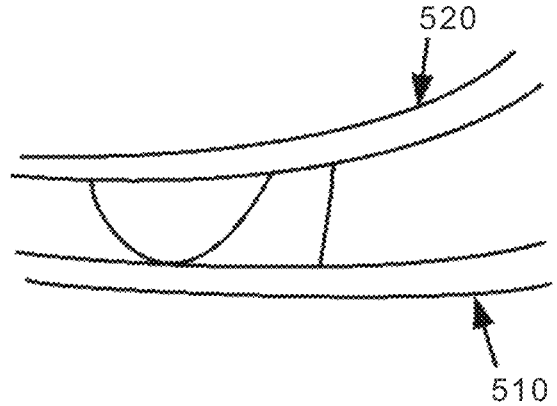
Fig. 5B
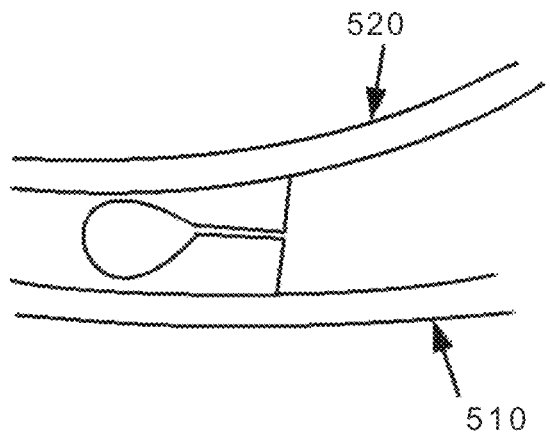
Fig. 5C
FIGs. 5A-5C

SECTION A-A

PARTIAL ASSY (UPPPER COMPONENTS
OMITTED FOR CLARITY)

EXPLODED VIEW

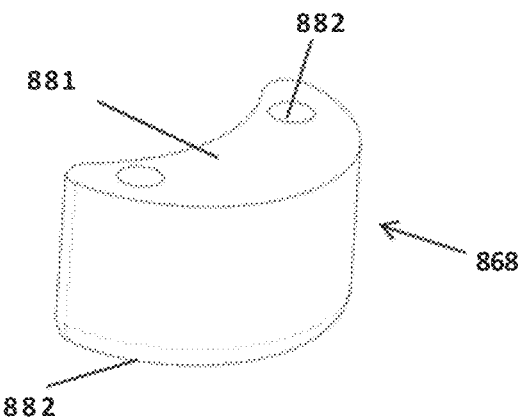
Figure 23A
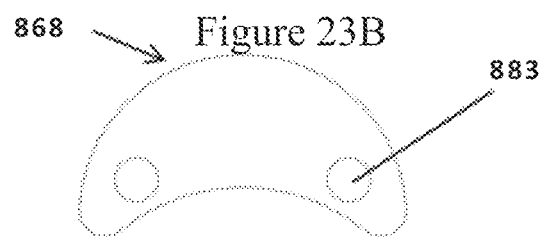
Figure 23B
Figure 23C
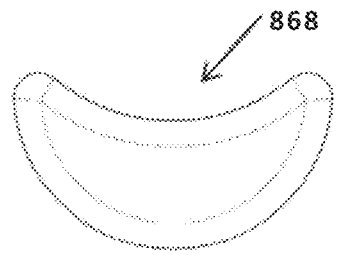

SECTION A-A

SECTION B-B

SECTION C-C

SECTION A-A

SECTION C-C

SECTION D-D

SECTION E-E

SECTION G-G

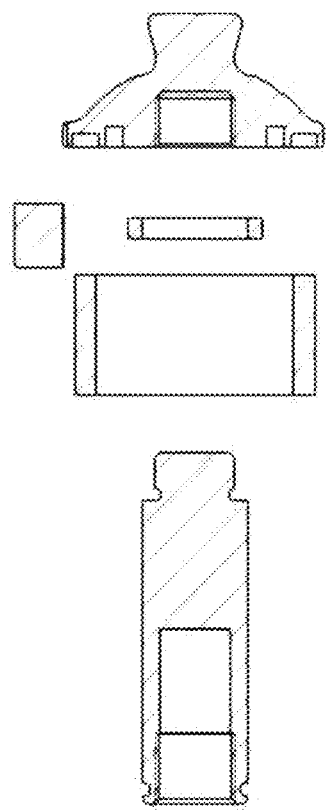
Figure 55
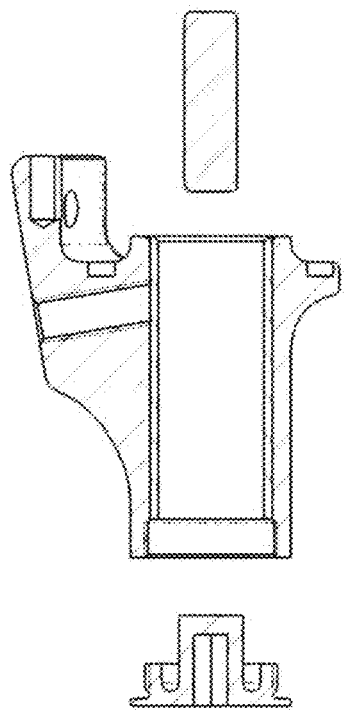
SECTION F-F

SECTION K-K

SECTION J-J

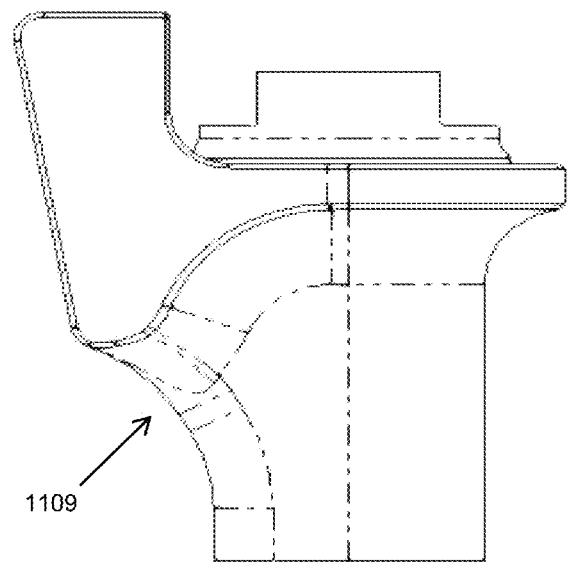
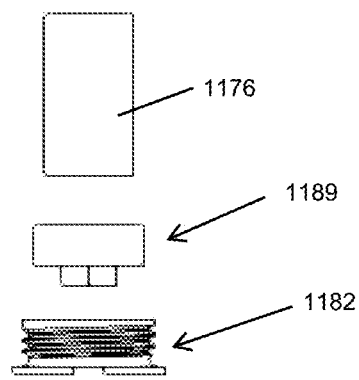
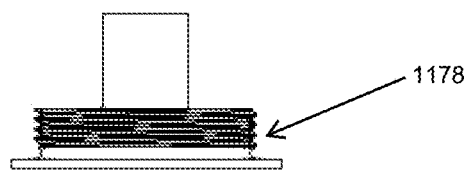
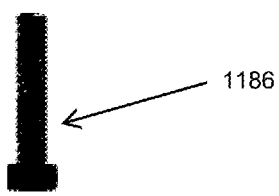
Figure 77

MOUNTING BRACKET FOR CONNECTING A PROSTHETIC LIMB TO A PROSTHETIC FOOT

CROSS-REFERENCES TO RELATED APPLICATIONS

The present application claims the benefit of U.S. Provisional Application Ser. No. 63/078,748, filed Sep. 15, 2020 and U.S. Provisional Application Ser. No. 63/137,970, filed Jan. 15, 2021, and is a continuation in part of U.S. patent application Ser. No. 16/281,278, filed Feb. 21, 2019, which is a continuation in part of U.S. patent application Ser. No. 15/726,712, filed Oct. 6, 2017, now U.S. Pat. No. 10,405,998, which claims the benefit of U.S. Provisional Application Ser. No. 62/407,954, filed Oct. 13, 2016, U.S. Provisional Application Ser. No. 62/451,870, filed Jan. 30, 2017, and U.S. Provisional Application Ser. No. 62/539,743, filed Aug. 1, 2017; and is a continuation in part of U.S. patent application Ser. No. 14/976,129, filed Dec. 21, 2015, which is a continuation of U.S. patent application Ser. No. 14/731,818, filed Jun. 5, 2015, which is a continuation of U.S. patent application Ser. No. 13/568,535, filed on Aug. 7, 2012; and this application is a continuation in part of U.S. patent application Ser. No. 15/726,712, filed Oct. 6, 2017, now U.S. Pat. No. 10,405,998, which is a continuation in part of U.S. patent application Ser. No. 14/976,129, filed Dec. 21, 2015, which is a continuation of U.S. patent application Ser. No. 14/731,818, filed Jun. 5, 2015, which is a continuation of U.S. patent application Ser. No. 13/568,535, filed on Aug. 7, 2012, which is a continuation-in-part of International Application No. PCT/US11/33319, filed on Apr. 20, 2011, which is a continuation-in-part of U.S. patent application Ser. No. 12/799,215, filed on Apr. 20, 2010, which is a continuation-in-part of U.S. patent application Ser. No. 11/901,845, filed on Sep. 19, 2007, now U.S. Pat. No. 8,048,173; and this application is a continuation in part of U.S. patent application Ser. No. 15/726,712, filed Oct. 6, 2017, now U.S. Pat. No. 10,405,998, which is a continuation in part of U.S. patent application Ser. No. 14/976,129, filed Dec. 21, 2015, which is a continuation of U.S. patent application Ser. No. 13/568,535, filed on Aug. 7, 2012, which is a continuation-in-part of International Application No. PCT/US11/33319, filed on Apr. 20, 2011, which is a continuation-in-part of U.S. patent application Ser. No. 12/799,215, filed on Apr. 20, 2010, which is a continuation-in-part of U.S. patent application Ser. No. 11/901,845, filed on Sep. 19, 2007, now U.S. Pat. No. 8,048,173; and this application is a continuation-in-part of U.S. patent application Ser. No. 14/731,771, filed Jun. 5, 2015, which is a continuation of U.S. patent application Ser. No. 13/642,501, filed on Nov. 27, 2012, now U.S. Pat. No. 9,078,773, which is a 371 national phase application of International Application No. PCT/US11/33319, filed on Apr. 20, 2011, which is a continuation-in-part of U.S. patent application Ser. No. 12/799,215, filed on Apr. 20, 2010, which is a continuation-in-part of U.S. patent application Ser. No. 11/901,845, filed on Sep. 19, 2007, now U.S. Pat. No. 8,048,173 and incorporates the disclosure of all such applications by reference, and this application incorporates the disclosure of all such applications by reference.

FIELD OF THE INVENTION

This invention pertains to prosthetic devices. More particularly, the invention pertains to a prosthetic foot and mounting bracket for a prosthetic foot that, when utilized by an amputee, better replicates the action of a real foot and reduces the risk of injury to the amputee.

BACKGROUND OF THE INVENTION

Prosthetic feet are well known in the art. In use, such prosthetic feet typically do not replicate the action of a real foot and can generate "kickback" or "kickforward" reactions that increase the risk of injury to an amputee utilizing the foot. Kickback is motion created by the prosthetic foot in a backward direction during the walking cycle. Kickforward is motion created by the prosthetic foot in a forward direction during the walking cycle. Either motion may create instability for the user if expanding or restricting the intended motion. Further, many prior art prosthetic feet generate vibrations that can travel through a user's leg and cause discomfort.

For an amputee, losing bipedality may produce an involuntary anterior lean or shift, forcing a constant imbalance or rebalance of posture. The amputee no longer possesses voluntary muscle control on his involved side due to the severance of the primary flexor and extensor muscles. The primary anterior muscle responsible for dorsiflexion (sagittal plane motion) is the anterior tibialis. Dorsiflexion is the voluntary ankle motion that elevates the foot upwards, or towards the midline of the body. The primary posterior muscle responsible for plantarflexion is the gastro-soleus complex. It is a combination of two muscles working in conjunction: the gastrocnemius and the soleus. Plantarflexion is the voluntary ankle motion that depresses the foot downwards, or away from the midline of the body. Therefore, it is desirable to have a prosthetic foot configured to promote increased muscle activity and promote increased stability for amputees, and it is desirable to provide an improved prosthetic foot which would better replicate the action of a true foot. Furthermore, it is desirable to provide an improved prosthetic foot which minimizes or eliminates "kickback" forces when the foot is utilized to walk over a door jamb or other raised profile object on a floor or on the ground, as well as reduce vibrations.

In use, such prosthetic feet are typically mounted to either an above knee amputation or a below knee amputation and are designed to mimic the natural gait of a user. Depending on the type of amputation, different types of mounting systems may be utilized. For example, if the amputation is above the knee, various suspension systems may be utilized in conjunction with the prosthetic foot to enhance the feel, fit, and function. An above the knee amputation allows for multiple options as there is significant space between the residual limb and the prosthetic foot. With a below the knee amputation, depending on the location, there may be less space between the user's residual limb and the prosthetic foot thereby allowing for different attachment configurations for the prosthetic foot.

SUMMARY OF THE INVENTION

An exemplary mounting bracket for a prosthetic foot may comprise an upper member, a lower member, and a compression torsion joint connecting the upper member to the lower member. The upper member may be configured for attachment to a user's residual limb. The lower member may be configured to attach to the prosthetic foot.

Furthermore, in another embodiment, a prosthetic foot may comprise a resilient bottom member having a first bottom end and a second bottom end, a resilient top member having a first top end and a second top end, wherein the first top end is connected to the first bottom end of the resilient bottom member, and wherein the resilient top member is connected to a mounting bracket and positioned over the resilient bottom member and directed towards the back of the prosthetic foot, and a toe pad. The toe pad can comprise at least one spacer coupled to, and creating space between, the first bottom end of the bottom member and the first top end of the top member, and an adhesive bonding the first bottom end of the bottom member and the first top end of the top member, wherein the adhesive is commingled with the at least one spacer between the first bottom end and the first top end.

BRIEF DESCRIPTION OF THE DRAWINGS

These and other features, aspects and advantages of the present invention will become better understood with reference to the following description, appending claims, and accompanying drawings where:

FIG. 5A-5C are side views illustrating various embodiments of a damper bar configuration;

FIG. 23A is a perspective view representatively illustrating a bumper of the mounting bracket in accordance with exemplary embodiments of the present technology;

FIG. 23B is a top view representatively illustrating the bumper of the mounting bracket in accordance with exemplary embodiments of the present technology;

FIG. 23C is a top view representatively illustrating the bumper of the mounting bracket in accordance with exemplary embodiments of the present technology;

FIG. 55 is a side, exploded, cross-section view taken along the line G-G in FIG. 54A representatively illustrating portions of the mounting bracket in accordance with exemplary embodiments of the present technology;

FIG. 77 is an exploded, side view of the retention system and the lower member in accordance with exemplary embodiments of the present technology;

Figure 1A:
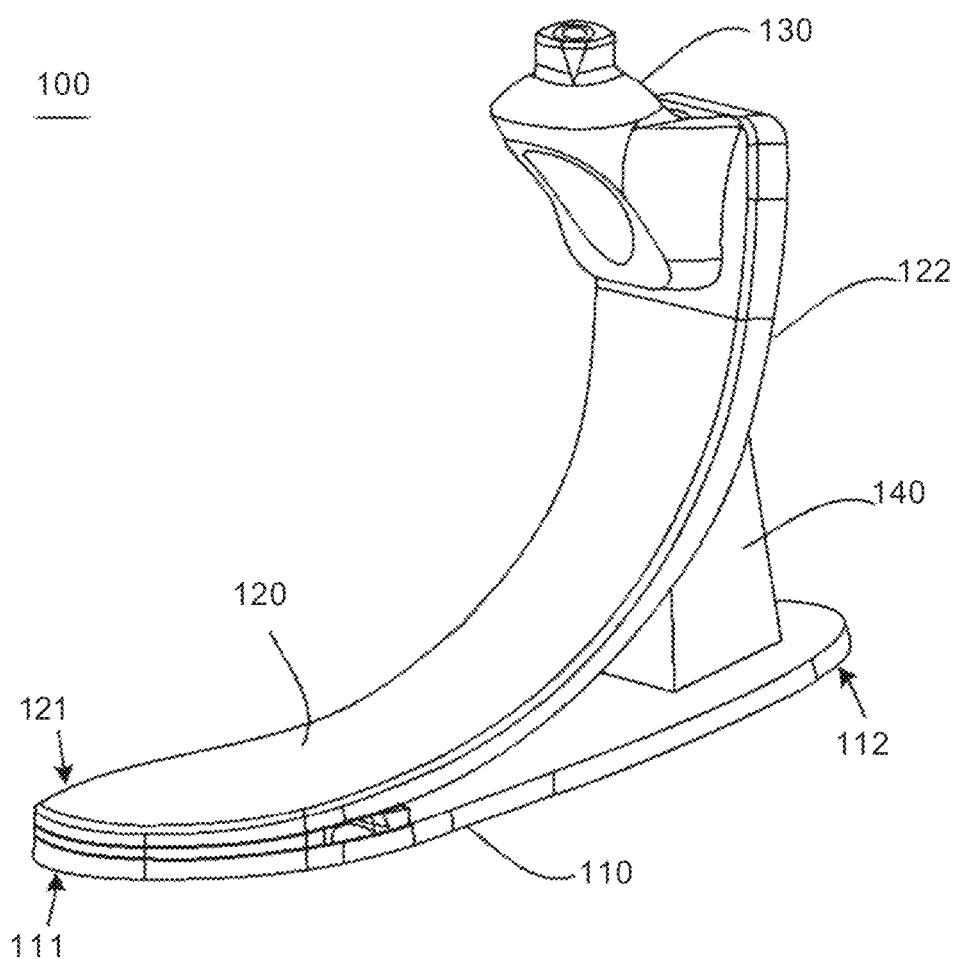
FIGS. 1A and 1B are perspective views illustrating a prosthetic foot constructed in accordance with various embodiments.

Elements and steps in the figures are illustrated for simplicity and clarity and have not necessarily been rendered according to any particular sequence. For example, steps that may be performed concurrently or in a different order are illustrated in the figures to help to improve understanding of embodiments of the present technology.

DETAILED DESCRIPTION OF EXEMPLARY EMBODIMENTS

The present technology may be described in terms of functional block components and various processing steps. Such functional blocks may be realized by any number of components configured to perform the specified functions and achieve the various results. For example, the present technology may be used with a prosthetic foot for various amputation types (above knee, below knee, etc.). In addition, the present technology may be practiced in conjunction with any number of materials and methods of manufacture and the system described is merely one exemplary application for the technology.

While exemplary embodiments are described herein in sufficient detail to enable those skilled in the art to practice the invention, it should be understood that other embodiments may be realized and that logical structural, material, and mechanical changes may be made without departing from the spirit and scope of the invention. Thus, the following descriptions are not intended as a limitation on the use or applicability of the invention, but instead, are provided merely to enable a full and complete description of exemplary embodiments.

Briefly, in accordance with exemplary embodiments, a prosthetic foot has improvements over a prior art prosthetic foot in that a more natural motion and response of the foot occurs during movement. In particular, the movement of the exemplary prosthetic foot replicates the natural flex of a foot and supplies continuous energy to a person when striding from heel to toe.

Briefly, in accordance with exemplary embodiments, a mounting bracket for a prosthetic foot is illustrated, which comprises a more natural motion and response during movement. In particular, the movement of the mounting bracket may replicate the natural movement of a foot, provide vertical shock absorption and allow for torsional rotation.

A typical prosthetic foot stores energy during the gait cycle and transfers the return potential energy in order to "put a spring in your step." The roll through of a prosthetic foot is defined in the gait cycle as the process from the heel-strike phase to the mid-stance phase to the toe-off phase. The heel-strike phase begins when the heel of the foot touches the ground, and includes the loading response on the foot. The mid-stance phase is when the foot is flat on the ground and the body's center of gravity is over the foot. The toe-off phase is the finish of the stance phase and ends when the tip of the foot is the only portion in contact with the ground, and the load is entirely on the toe. This is just prior to the swing phase, which constitutes the other half of the gait cycle.

As the user moves through the stance phase portion of the gait cycle the tibia portion of the leg, or that section of the leg defined below the knee, rotates through in relation to the ground. If the mid-stance phase is defined as the lower leg at 90 degrees to the ground, then looking at the side view of an individual, the angle of the lower leg at the heel-strike phase may occur at approximately 65 degrees and the angle of the lower leg at the toe-off phase may occur at approximately 110 degrees. The rotation of the lower leg on the theoretical ankle is notated as tibial progression or lower leg progression during the stance phase. The mounting bracket provides vertical shock absorption though the gait cycle and while standing and further allows for torsional rotation.

Figure 1B:
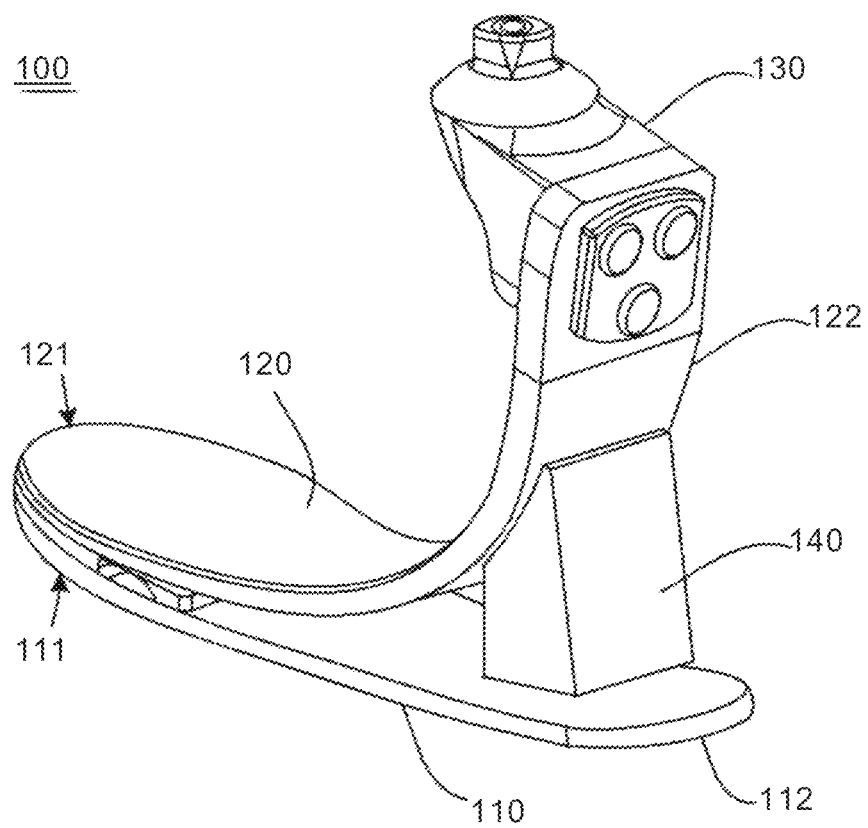

In accordance with various embodiments and with reference to FIGS. 1A and 1B, a prosthetic foot 100 comprises a resilient bottom member 110, a resilient top member 120, a connection point 130 attached to the top member 120 and configured for attachment to a user, and a bumper member 140. The resilient bottom member 110 may have an anterior bottom end 111 and a posterior bottom end 112. The resilient top member 120 may have an anterior top end 121 and a posterior top end 122. Further, the anterior top end 121 of the resilient top member 120 can be connected to the anterior bottom end 111 of the resilient bottom member 110, while the resilient top member 120 can be positioned over the resilient bottom member 120 and directed towards the posterior of the prosthetic foot 100.

Further, in various embodiments, prosthetic foot 100 also comprises an elastomeric bumper member 140 having a tapered surface configured to contact the resilient bottom member 110 and attached to an underside of the posterior top end 122 of the resilient top member 120. The bumper member 140 can be vertically oriented with respect to the prosthetic foot 100. The bumper member 140 can act as a heel shock for absorbing force on the downward strike during the user's stride.

In various embodiments, the bumper member 140 can be made from an elastomeric material. In one embodiment, the elastomeric material has about 80% or greater energy return. In another embodiment, the elastomeric material has about 90% or greater energy return. The bumper member 140 can be designed to behave similar to a non-linear spring, thereby allowing larger deflection of the posterior toe and 122 during the heel strike. The progressive "spring rate" may lead to a soft heel strike but does not deflect too far as the bumper member 140 compresses. One benefit of the bumper 140 is being relatively lightweight in comparison to a prosthetic foot with coiled springs.

Figure 2:
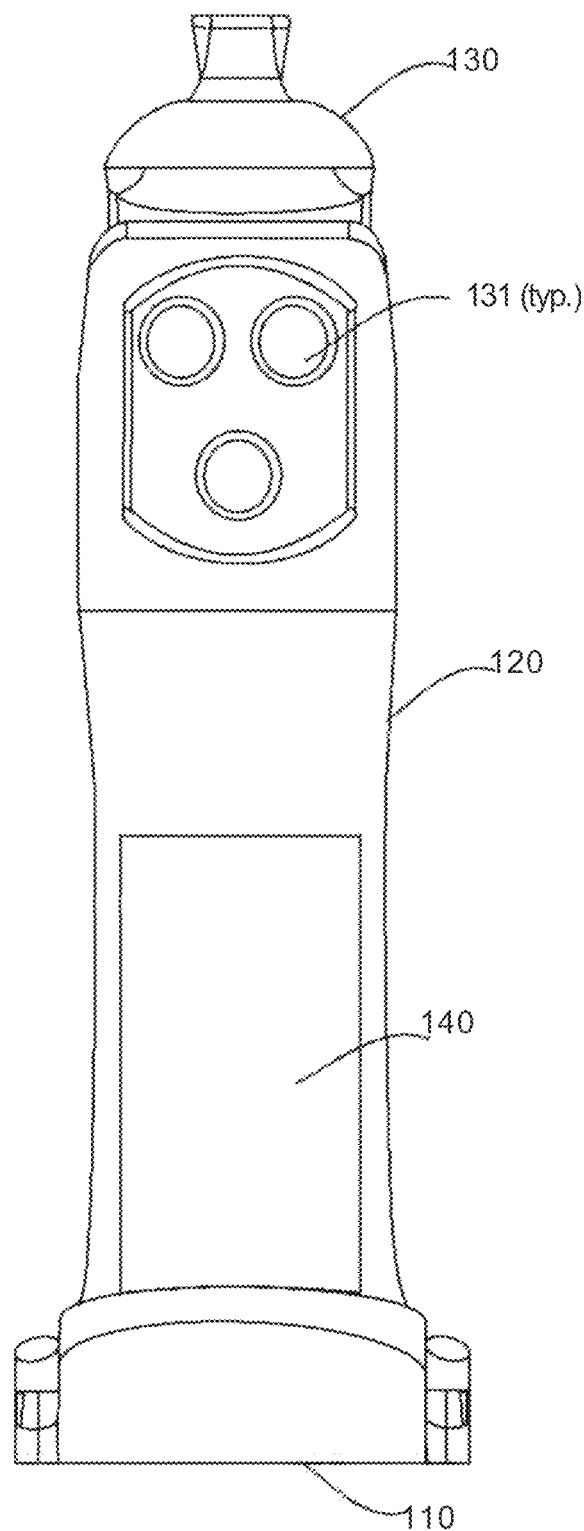
FIG. 2 is a rear view further illustrating the prosthetic foot of FIGS. 1A and 1B.

The bumper member 140 can be located posterior to vertical axis of the connection point 130. The bumper member 140 can be attached to the underside of the top member 120 in various manners. For example and with reference to FIG. 2, the bumper member 140 can be fixedly attached using adhesive or fasteners, such as screws. In another example, the bumper member 140 may be detachable using fasteners for replacement purposes. Moreover, in other embodiments, the bumper member 140 can be attached to various locations on the underside of the top member 120 or topside of the bottom member 110. In various embodiments, the prosthetic foot 100 in a static mode has a gap between the bumper member 140 and the bottom member 110. For example, a gap of about 1/10 inch may be present between the bumper member 140 and the bottom member 110. In other various methods, the bumper member 140 can be in contact with both the top member 120 and the bottom member 110 when the prosthetic foot 100 is in a static position. The lack of a gap results in the bumper member 140 being continuously compressed during the gait cycle, though the bumper member 140 is a compression member and not a tension member since the bumper member 140 is only attached to either the top member 120 or the bottom member 110. The bumper member 140 not being attached to the other of the top member 120 or the bottom member 110 provides flexibility during the gait cycle of the prosthetic foot 100 to more closely mimic a natural foot/ankle system. Connecting the bumper member 140 to both the resilient top and bottom members 120, 110 creates almost a triangle structure, which is very stiff.

The bumper member 140 can be in many shapes. In various embodiments, the detached portion of the bumper member 140 may have a conical, rectangular, or pyramid shape. The tapered surface of the bumper member 140 can terminate in an apex or hemispherical shape, and the apex can be configured to contact the bottom member 110 in response to deflection of the prosthetic foot 100. Moreover, in various embodiments, the bumper member 140 can terminate in multiple points. The tapered bumper member 140 facilitates a damping of vibration and sound generated during heel strike or release. Furthermore, in various embodiments the extruding portion of the bumper member 140 may be any shape that is non-flat surface. Further, a non-flat surface enhances lateral flexibility if the heel strike is not vertical.

The prosthetic foot 100 can be adjusted to accommodate a user in part by adjusting characteristics of the bumper member 140. For example, in various embodiments, the durometer of the bumper member 140 can be increased for users with more heel strike force, which may be caused by additional weight or dynamic activity. A heavier user may be better-suited using a bumper member with a large cross-sectional area compared to a lighter user using a bumper member with a small cross-sectional area.

Figure 3:
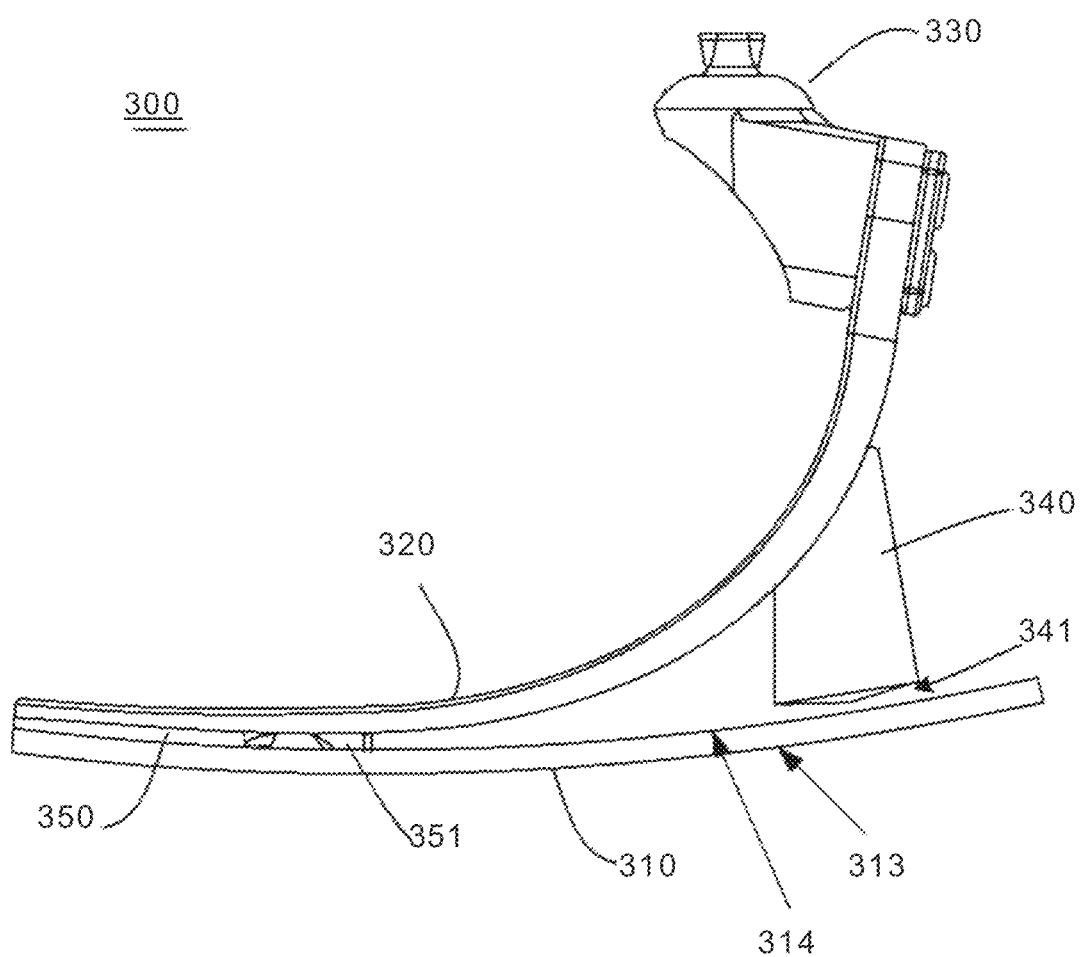
FIG. 3 is a side view further illustrating the prosthetic foot of FIGS. 1A and 1B.

In accordance with various embodiments and with reference to FIG. 3, a prosthetic foot 300 comprises a resilient bottom member 310, a resilient top member 320, a connection point 330 attached to the top member and configured for attachment to a user, and a toe pad 350 coupled to the top surface of the bottom member 310 at a first bottom end and coupled to the bottom surface of the top member 320 at a first top end. Also, in various embodiments, prosthetic foot 300 may further comprise a bumper member 340. In various embodiments, the toe pad 350 comprises at least one spacer and an adhesive bonding the top surface of the bottom member 310 and the bottom surface of the top member 320. For example, the anterior quarter of the bottom member 310 can be adhesively connected to the top member 320. In various embodiments, adhesive can be used to connect 23-27% of the top surface area of the bottom member 310 to the top member 320. Further, in various embodiments, adhesive can be used to connect approximately 1/3 of the top surface area of the bottom member 310 to the top member 320.

In various embodiments, the toe pad 350 has approximately constant thickness. In other various embodiments, the toe pad 350 can have a thickness that tapers towards the front edge of the prosthetic foot 300. In other words, the toe pad 350 closer to the heel can be thicker than the toe pad 350 closer to the toe. Further, the adhesive bonding of the toe pad 350 can produce distributed stresses. In accordance with various embodiments, the adhesive can have a higher modulus of elasticity in contrast to the elastomer of the toe pad. Though other modulus values are contemplated, and various moduli may be used as well, a stiffer adhesive is preferred compared to a flexible adhesive.

The spacer of the toe pad 350 creates a space between the top surface of the bottom member 310 and the bottom surface of the top member 320. The adhesive can be commingled with the spacer between the top surface of the bottom member 310 and the toe pad 350 and also between the bottom surface of the top member 320 and the toe pad 350. In various embodiments, the space created by the spacer can be non-compressed space for the placement of the adhesive. In other words, the spacer can create a void between the top member 320 and the bottom member 310 and the void can be filled with the adhesive for bonding. The inclusion of the toe pad 350 may reduce the stress applied to the adhesive bond during the gait cycle. In various embodiments, the spacer can be elastomeric stand-offs, such as dots, ribs, or other patterns to create the desired spacing. Moreover, in various embodiments, the spacer is a single piece of connected stand-offs. The single piece spacer facilitates easier alignment during the manufacturing process and can provide a more uniform stand-off pattern compared to multiple stand-off spacers.

The toe pad 350 can also comprise an adhesive composite with spacers. In various embodiments of the prosthetic foot 300, the spacer is an aggregate material combined with the adhesive to form the adhesive composite. In various embodiments, the adhesive composite includes adhesive and microspheres. The microspheres can create the spacing between the top and bottom members 320, 310.

Figure 4A:
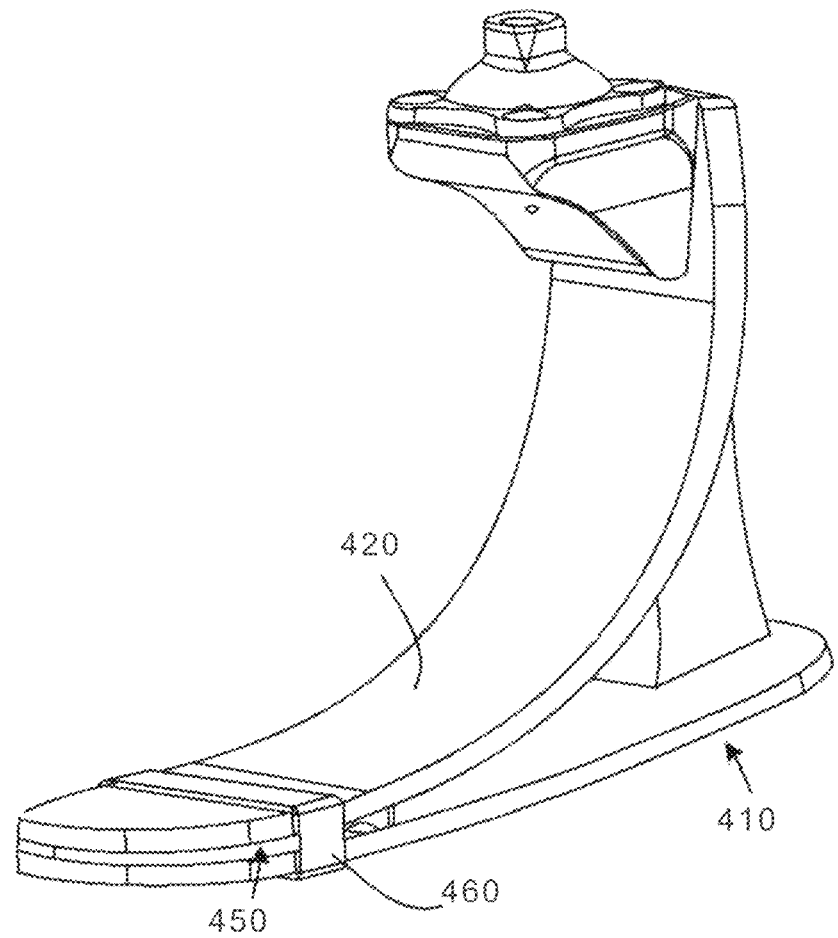
FIGS. 4A and 4B are perspective views illustrating a prosthetic foot comprising a toe wrap.
Figure 4B:
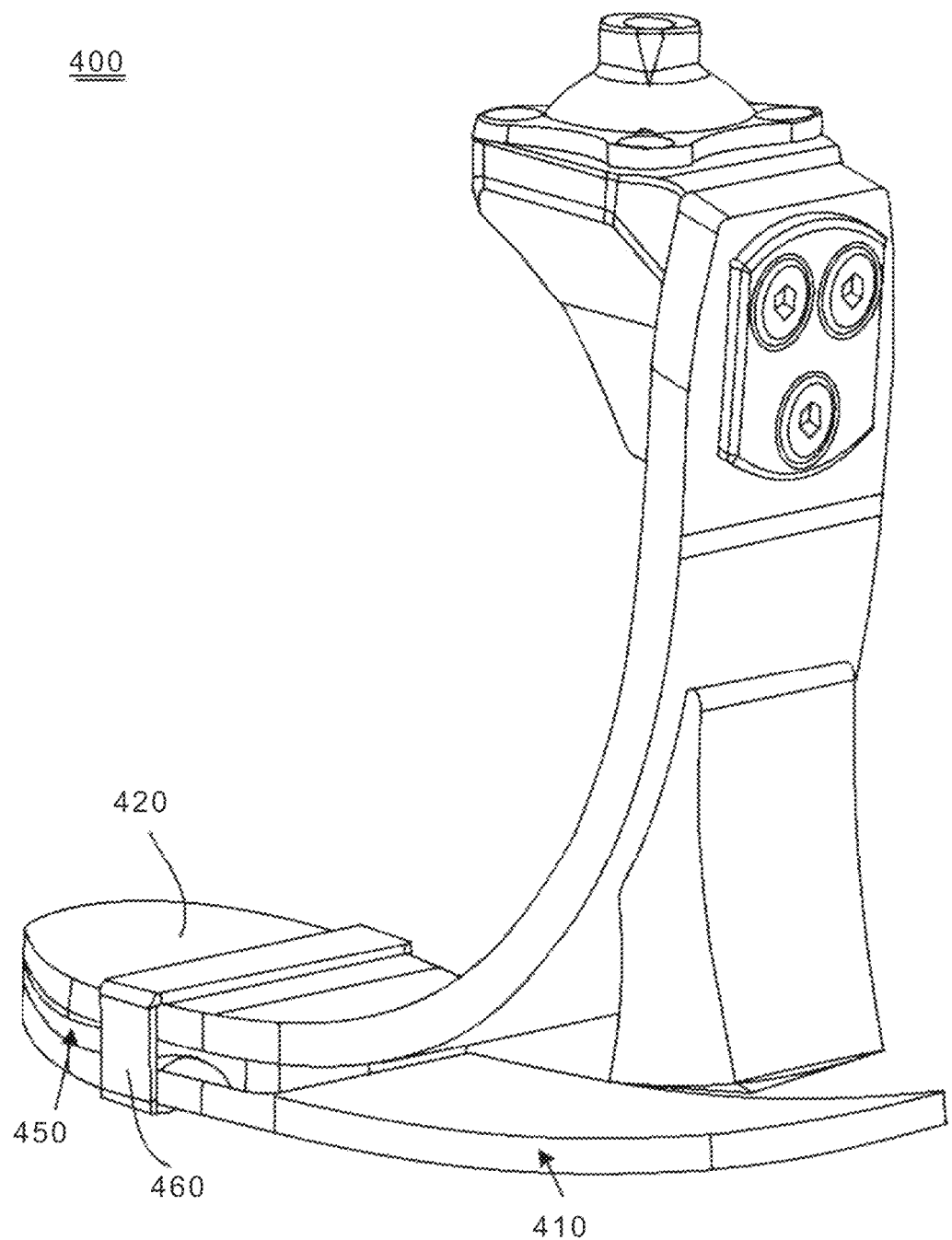

Additionally, in various embodiments and with reference to FIGS. 4A and 4B, a prosthetic foot 400 can comprise a bottom member 410, a top member 420, a toe pad 450, and a toe wrap 460 bonded around the top and bottom of the bonded bottom and top members 410, 420. The toe wrap 460 can be made out of a fiber material. The toe wrap material can also be a fiber weave with an elastomeric material. For example, the toe wrap can be a Kevlar or nylon material belt that is approximately less than a $1/10^{th}$ of an inch in thickness. The toe wrap 460 can be configured to provide a secondary hold in case the adhesive bond of the toe pad 450 between the top and bottom members breaks. Also, the toe wrap 460 can strengthen the attachment between the bottom and top members 410, 420 during tension.

Moreover, in various embodiments and with renewed reference to FIG. 3, the prosthetic foot 300 can further comprise a damper bar 351 configured to attach to an underside of the resilient top member 320 and contact the resilient bottom member 310. The damper bar 351 can be configured to arrest the upward motion of bottom member 310 after toe off and also arrest the rotational energy during the gait cycle. The arrested motion creates a slower velocity and less motion at the point of contact of the damper bar 351. Without the damper bar, the bottom member 310 may slap against the bumper member 340 during the stride, resulting in vibration traveling up the leg of the user.

In various embodiments, the damper bar 351 can be located near the posterior edge of the toe pad 350. As an example, the damper bar 351 can be spaced ½ inch away from the posterior edge of the toe pad 350. In another example, the damper bar 351 can be located in the anterior portion of the bottom member 310. Further, the damper bar 351 can be approximately a ½ inch long, with the length measured from anterior to posterior of the bottom member 310. In various embodiments, the width of the damper bar 351 can be as wide as the attached top member 320. However, the damper bar 351 may also be less than the full width of the attached top member 320. Furthermore, in various embodiments, the contacting surface of the damper bar 351 can be flat. In alternative embodiments, the contacting surface of the damper bar 351 can be tapered to an apex. The contacting surface can be configured to reduce vibration and sounds caused from the contact of the non-connected bottom member 310 with the damper bar 351 during the gait cycle. Furthermore, in various embodiments, the contacting surface of the damper bar 351 can be various shapes other than flat, such as a preloaded taper.

In various embodiments, the damper bar 351 is connected to the toe pad 350, or is formed as part of the toe pad 350. One advantage of having the toe pad 350 and damper bar 351 as a single piece is for easier alignment during manufacturing of the prosthetic foot 300.

The damper bar 351 can be minimally load-bearing, whereas the bumper member 340 can be the primary load-bearing component. In various embodiments, the bumper member 340 can be located about four to five times farther back from the fulcrum point of the toe pad 350 in comparison to the damper bar 351. Furthermore, in various embodiments and with reference to FIGS. 5A-5C, a damper bar can be attached to the prosthetic foot in various configurations. For example, FIG. 5A illustrates a damper bar 551 attached to a top member 520, whereas FIG. 5B illustrates a damper bar 551 attached to a bottom member 510. In another example, FIG. 5C illustrates a damper bar 551 attached to both the bottom member 510 and the top member 520, where the damper bar 551 is divided such that the top and bottom member may separate and still arrest motion of the prosthetic foot.

Moreover and with renewed reference to FIGS. 1A and 1B, the top member 120, bottom member 110, and bumper member 140 transfer energy between themselves in a natural, true foot manner. The loading response during the heel strike phase compresses bumper member 140 and top member 120, which in turn passes energy into, and causes a deflection of, a rear portion of bottom member 110. Energy is transferred towards the front of prosthetic foot 100 during the mid-stance phase. Furthermore, an upward deflection of at least one of bottom member 110 and top member 120 stores energy during the transition from the mid-stance phase to the toe-off phase of the gait cycle. In an exemplary embodiment, about 90% or more of the heel strike loading energy is stored and transferred to top member 120 for assisting the toe-off phase. In another exemplary embodiment, about 95% or more of the heel strike loading energy is stored and transferred to top member 120 for assisting the toe-off phase. In yet another exemplary embodiment, about 98% or more of the heel strike loading energy is stored and transferred to top member 120 for assisting the toe-off phase. Prosthetic foot 100 may be designed to release the stored energy during the toe-off phase and assist in propelling the user in a forward direction.

In an exemplary embodiment and with renewed reference to FIG. 3, resilient bottom member 310 includes a bottom surface 313 and an upper surface 314. Resilient bumper member 340 includes a contact surface 341. When prosthetic foot 300 is compressed, resilient top member 320 and bumper member 340 are compressed and displaced downwardly toward resilient bottom member 310.

With respect to the walking motion, the prosthetic foot is configured to increase the surface-to-foot contact through the gait cycle. The increased surface contact allows for a smoother gait cycle, and increases stability in comparison to the typical prior art prosthetics. In exemplary embodiments, the underside of bottom member has different contours that provide increased surface contact for different types of uses.

Figure 6:
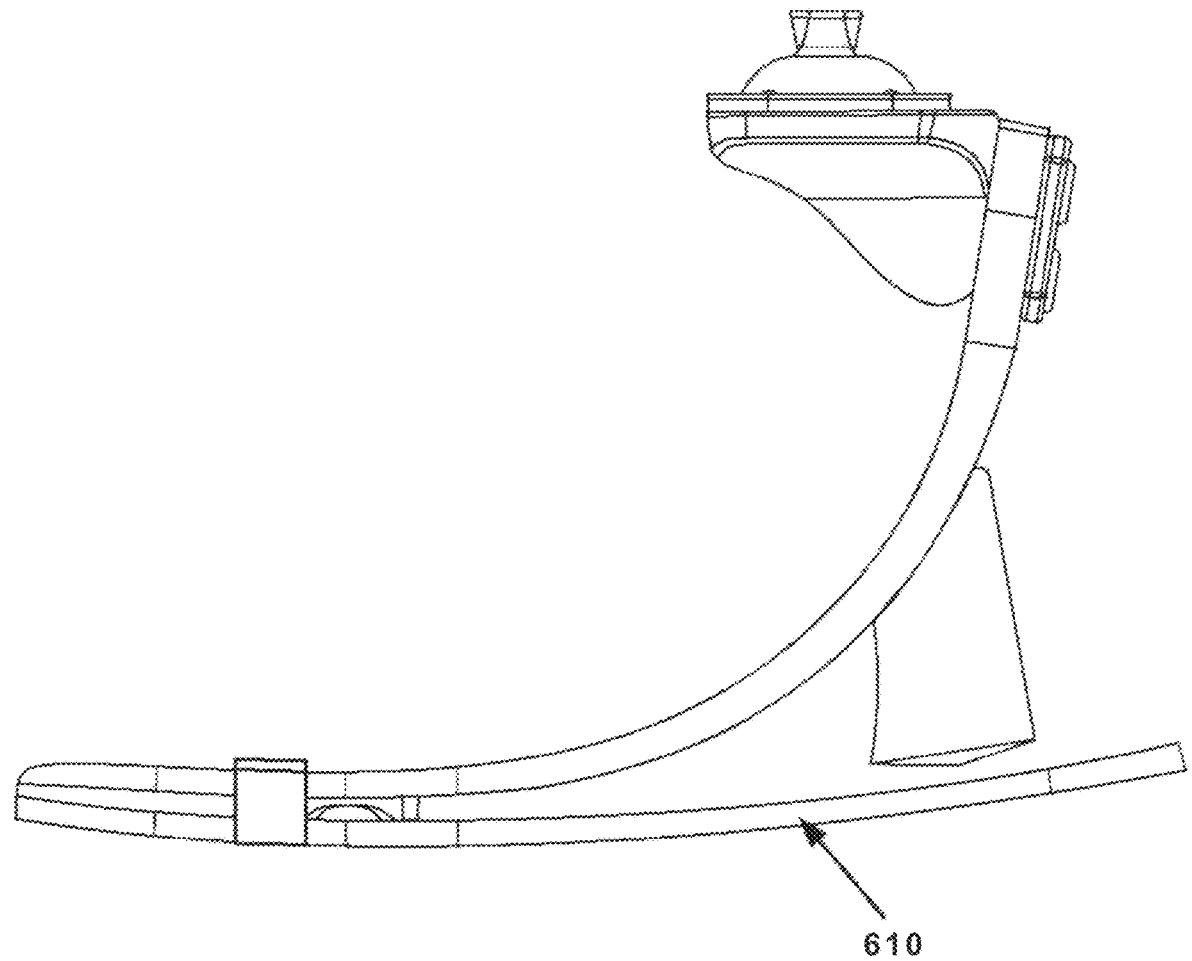
FIG. 6 is a side view illustrating an exemplary prosthetic foot for use by an above-knee amputee.

The bottom member of the prosthetic foot can have various shapes depending on desired use. The desired use may include prosthetic feet for above-knee amputees or prosthetic feet for below-knee amputees. In various embodiments and with reference to FIG. 6, a prosthetic foot 600 for above-knee amputees comprises a bottom member 610 having a curved bottom with no inflection point. In various embodiments, the bottom member 610 has a constant arc due to single radius forming the partial curve of the bottom member. In other various embodiments, the curve of the bottom member 610 can be designed as a spline of variable radii. The curve of bottom member 610 in above-knee prosthetic foot 600 facilitates keeping an artificial knee stable because the forces substantially restrict the knee from bending. The curved bottom member 610 enables a rocking motion even if the artificial knee is hyper-extended.

Figure 7:
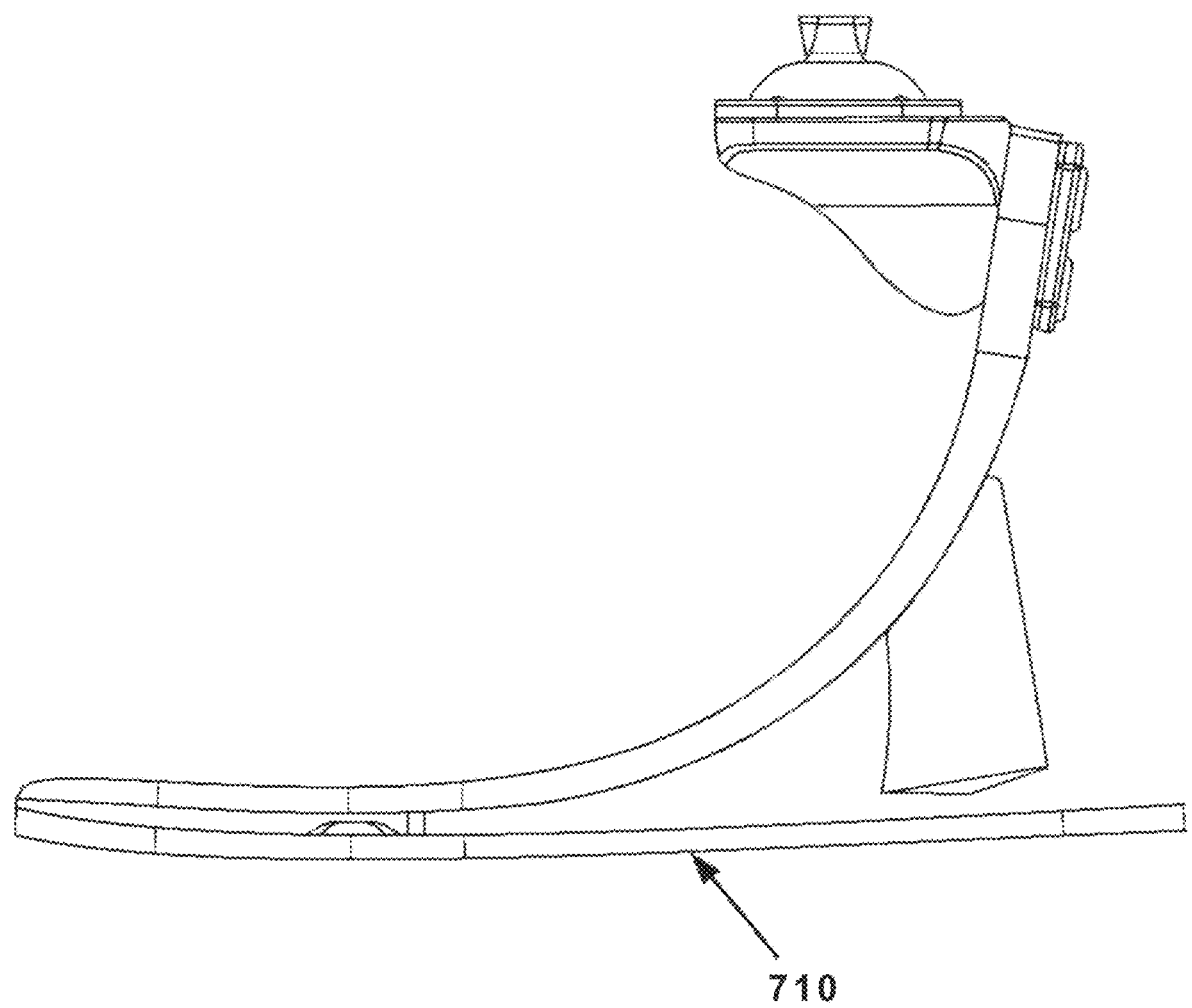
FIG. 7 is a side view illustrating an exemplary prosthetic foot for use by a below-knee amputee.

Similarly, in various embodiments and with reference to FIG. 7, a prosthetic foot 700 for below-knee amputees comprises a bottom member 710 having a partially curved portion in the anterior of the bottom member 710 and a substantially linear portion in the posterior portion of the bottom member 710. Similar to above-knee prosthetic foot 600, the anterior portion of bottom member 710 can have a constant arc due to single radius forming the partial curve. In various embodiments, the anterior portion of bottom member 710 can have a curve designed as a spline of variable radii. In accordance with various embodiments, the posterior portion of bottom member 710 can be substantially straight and tangent to the anterior portion such that bottom member 710 does not have an inflection point. A straight posterior portion and a curved anterior portion of bottom member 710 in below-knee prosthetic foot 700 facilitates rotation of the tibia progressing the natural rotation of the knee forward and preventing hyper-extension of the knee.

In accordance with an exemplary embodiment, resilient members 110, 120 are made of glass fiber composite. The glass fiber composite may be a glass reinforced unidirectional fiber composite. In one embodiment, the fiber composite material is made of multiple layers of unidirectional fibers and resin to produce a strong and flexible material. The fibers may be glass fibers or carbon fibers. Specifically, layers of fiber are impregnated with the resin, and a glass reinforcement layer can be positioned between at least two fiber weave layers. Typically, several layers of the unidirectional fibers or tape are layered together to achieve the desired strength and flexibility. Further, in various embodiments the layers of unidirectional fibers or tape can be oriented at various angles.

Mounting Bracket 800

Figure 8:
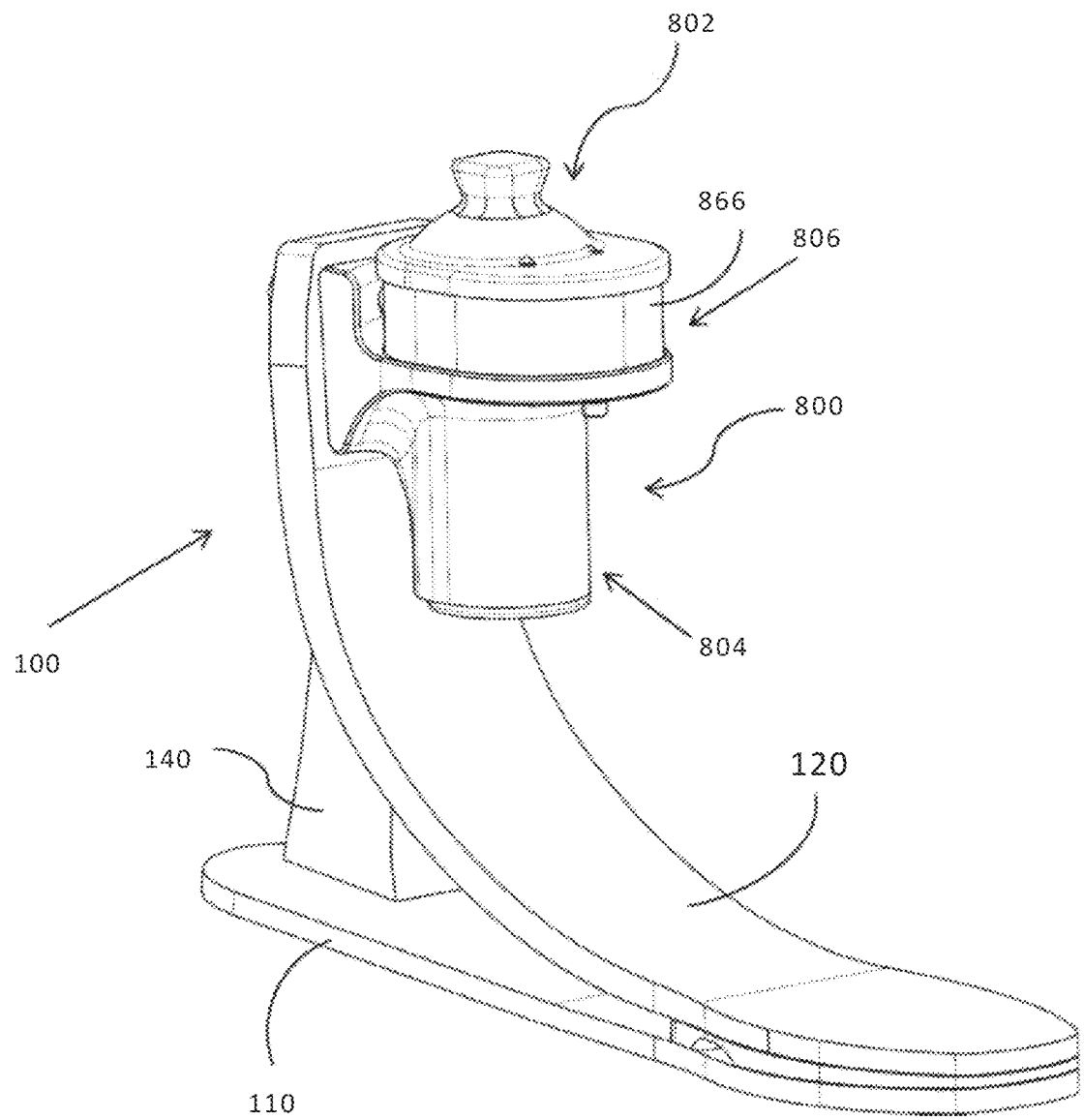
FIG. 8 is a perspective view representatively illustrating a mounting bracket on a prosthetic foot in accordance with exemplary embodiments of the present technology.
Figure 9:
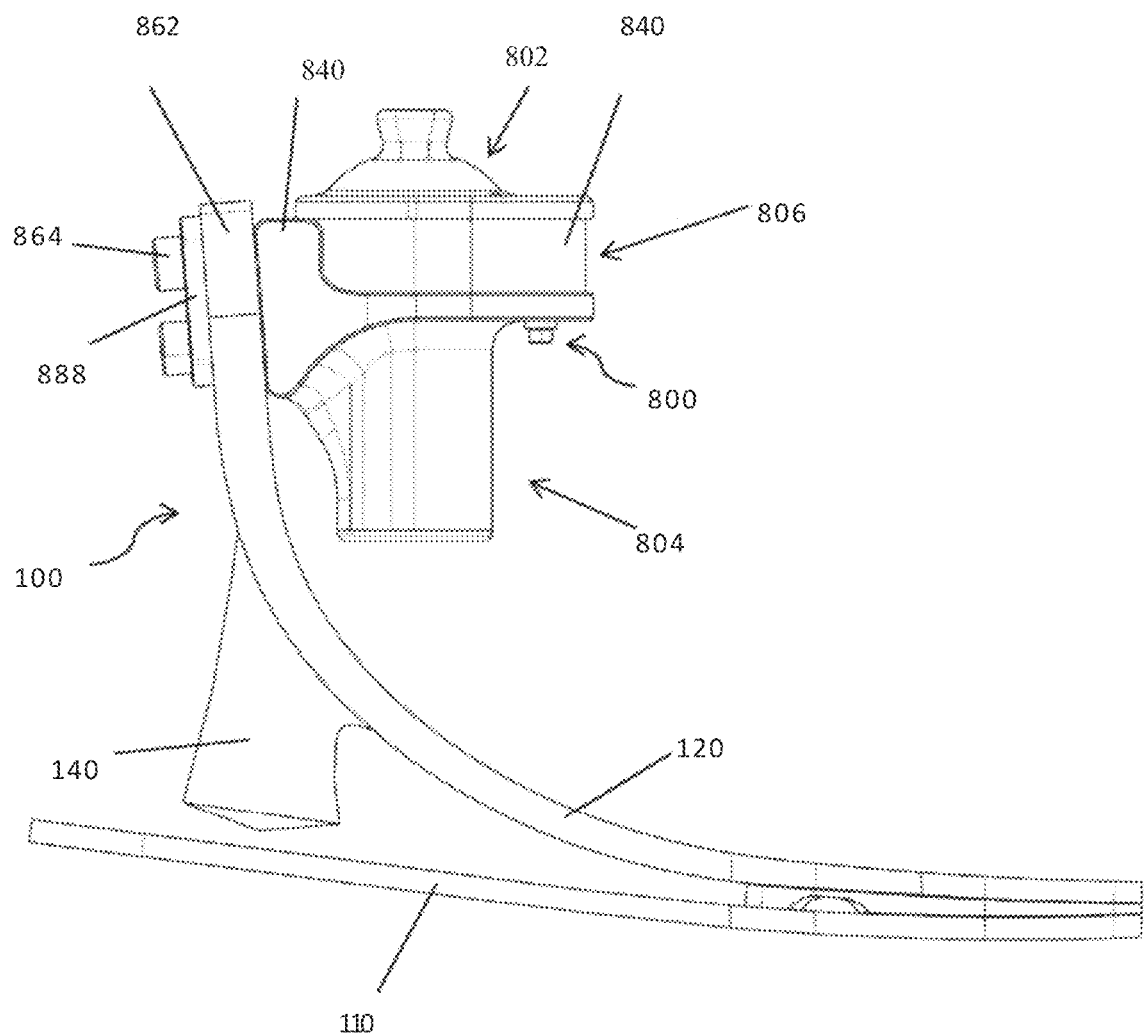
FIG. 9 is a side view representatively illustrating the mounting bracket on a prosthetic foot in accordance with exemplary embodiments of the present technology.
Figure 10:
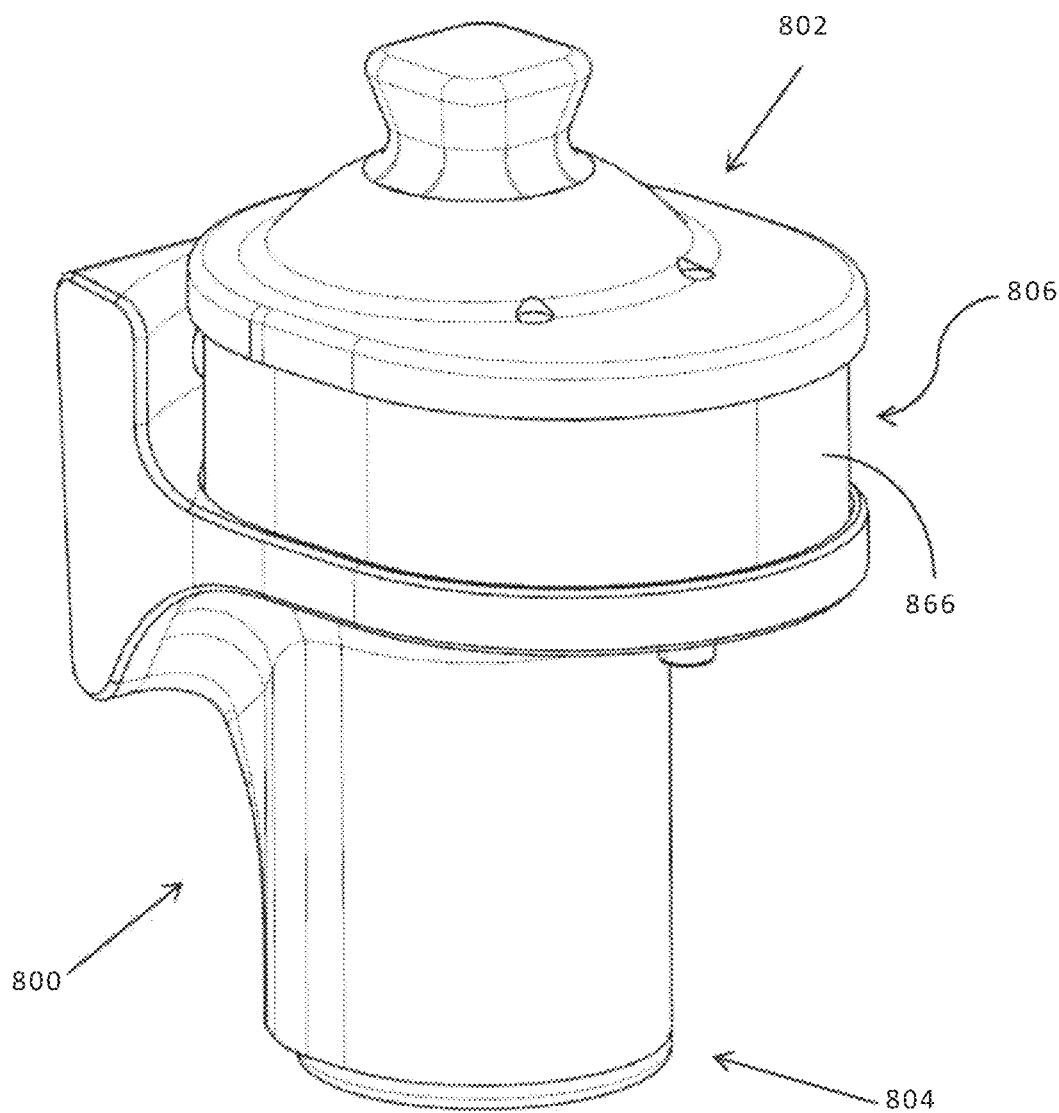
FIG. 10 is a perspective view representatively illustrating the mounting bracket in accordance with exemplary embodiments of the present technology.

In accordance with various embodiments and with reference to FIGS. 8-10, the connection point 130 may comprise a mounting bracket 800. The mounting bracket 800 may be attached to the top member 120 and configured for attachment to a user. In various embodiments, the mounting bracket 800 may comprise an upper member 802, a lower member 804, and a compression torsion joint 806. The upper member 802 may be configured for attachment to a user's residual limb. The lower member 804 may be configured to attach to a prosthetic foot. In one embodiment the lower member 804 is coupled to the prosthetic foot 100.

Figure 11A:
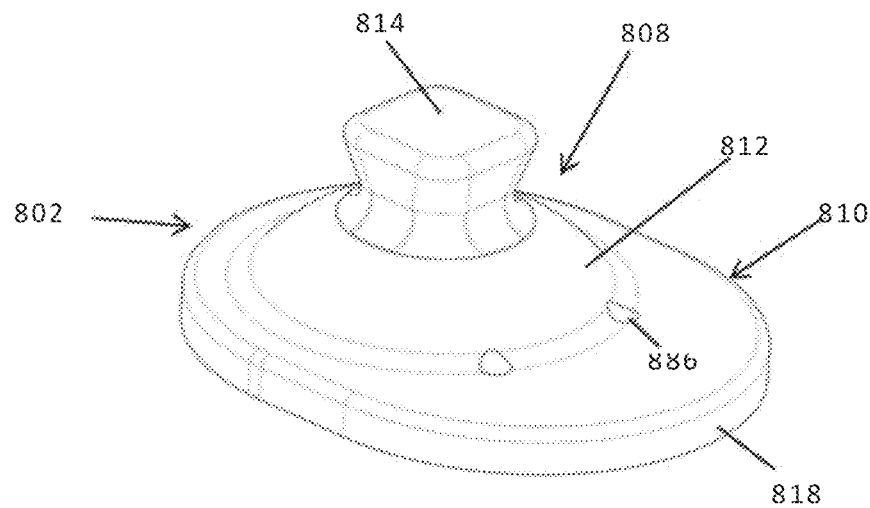
FIG. 11A is a perspective view representatively illustrating an upper member of the mounting bracket in accordance with exemplary embodiments of the present technology.
Figure 11B:
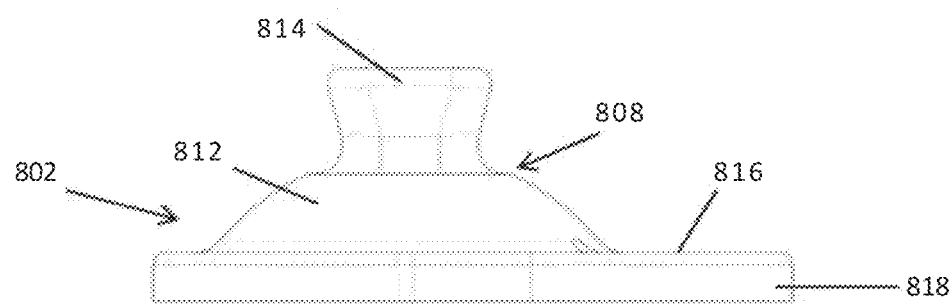
FIG. 11B is a side view representatively illustrating the upper member of the mounting bracket in accordance with exemplary embodiments of the present technology.
Figure 11C:
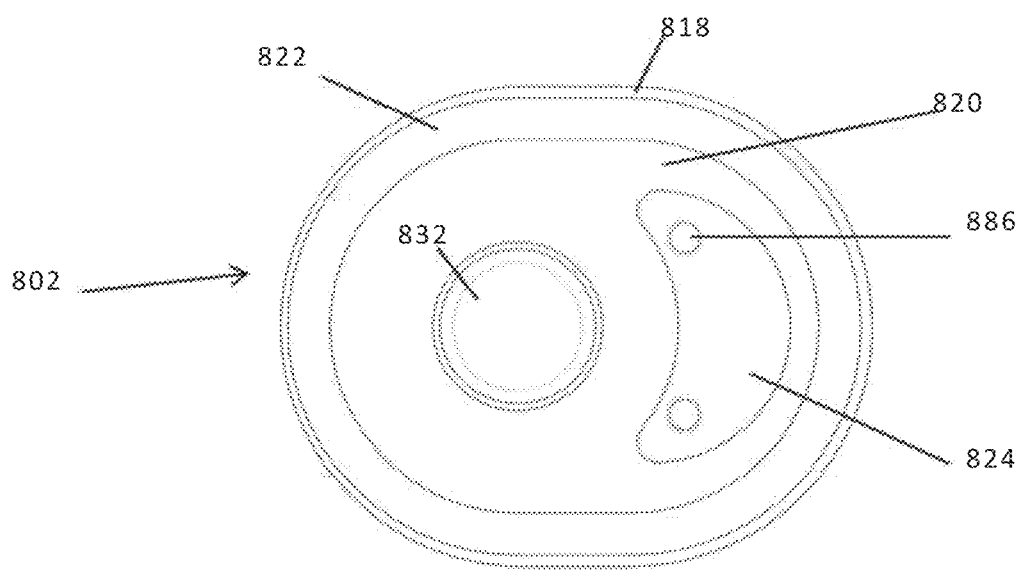
FIG. 11C is a bottom view representatively illustrating the upper member of the mounting bracket in accordance with exemplary embodiments of the present technology.

Referring now to FIG. 11A-C, in various embodiments, the upper member 802 may comprise mounting portion 808 and an upper flange 810. The mounting portion 808 may be configured to attach to a user's residual limb. The mounting portion 808 may comprise a spherical dome 812 and an attachment portion 814, which is a standard male pyramid adapter used in the prosthetic industry. The pyramid adapter may be coupled with a standard receiver used in the practice of prosthetics, for example, a Staats style attachment, which is commonly known in the prosthetic industry. The attachment portion 814 may use a standard receiver adapter, as understood by one of ordinary skill in the art. According to various embodiments the attachment portion 814 may facilitate attachment to the residual limb of the user. The attachment portion 814 may comprise a centerline that is aligned with the weight line of the user.

The spherical dome 812 may be located on an upper surface 816 of the upper flange 810. In various embodiments, the upper flange 810 may comprise a downwardly depending lip 818 around its perimeter and a lower surface 820 with a channel 822 contained therein. In various embodiments, the lower surface 820 of the upper flange 810 may comprise a recess 824. In one embodiment, the recess 824 may comprise a crescent-shaped recess 824.

In various embodiments, as shown in FIGS. 14B, 16, 19, 27A, and 27B the upper member 802 may also comprise a mating post 826. The mating post 826 may comprise a cylindrical collar 828 depending downwardly from the lower surface 820 of the upper flange 810. In various embodiments the mating post 826 may be removable. An upper portion 830 of the mating post 826 may be coupled to the upper member 802 within a recess 832 by any known method, such as screw fit, pressed, and the like. In one embodiment the mating post 826 may be coupled to the upper member 802 by a threaded connection. The mating post 826 may comprise threads (not shown) on the upper portion 830 of the cylindrical collar 828 that are received by threads (not shown) within the recess 832 in the upper member 802. The mating post 826 may further comprise at least one recess 834 on the perimeter of the cylindrical collar 828 that may receive O-rings (not shown). The O-rings serve to fill the clearance between the outer diameter of mating post 826 and the inner diameter of sleeve 902 to provide smooth, and silent action between relatively moving components. In one embodiment, the mating post 826 comprises at least one recess 836 on the perimeter of the cylindrical collar 828 that may receive grease or another lubricant during assembly.

Figure 12A:
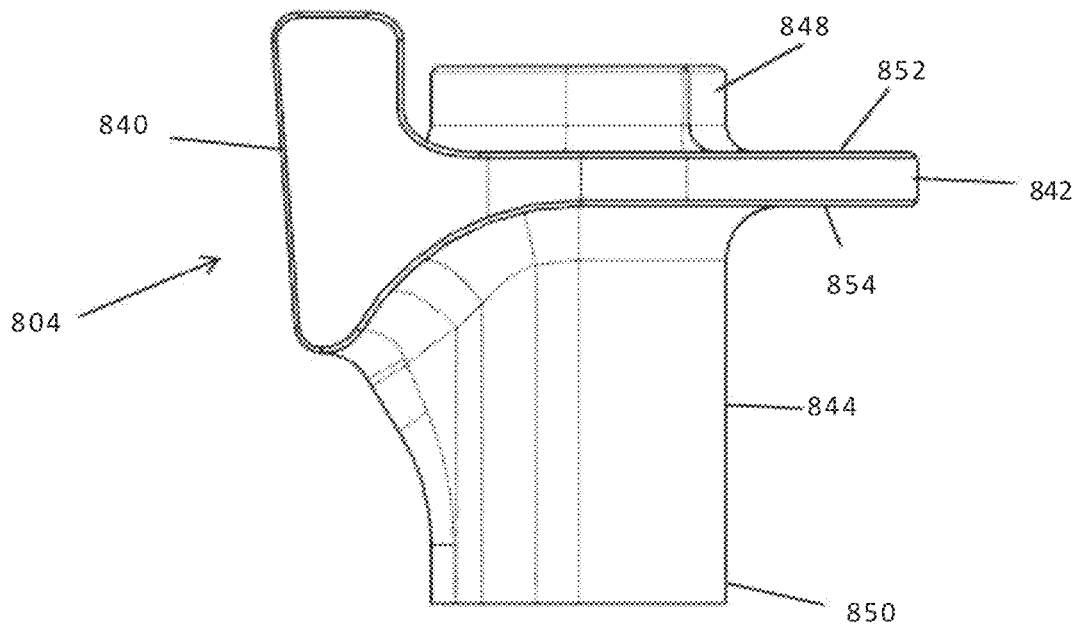
FIG. 12A is a side view representatively illustrating a lower member of the mounting bracket in accordance with exemplary embodiments of the present technology.
Figure 12B:
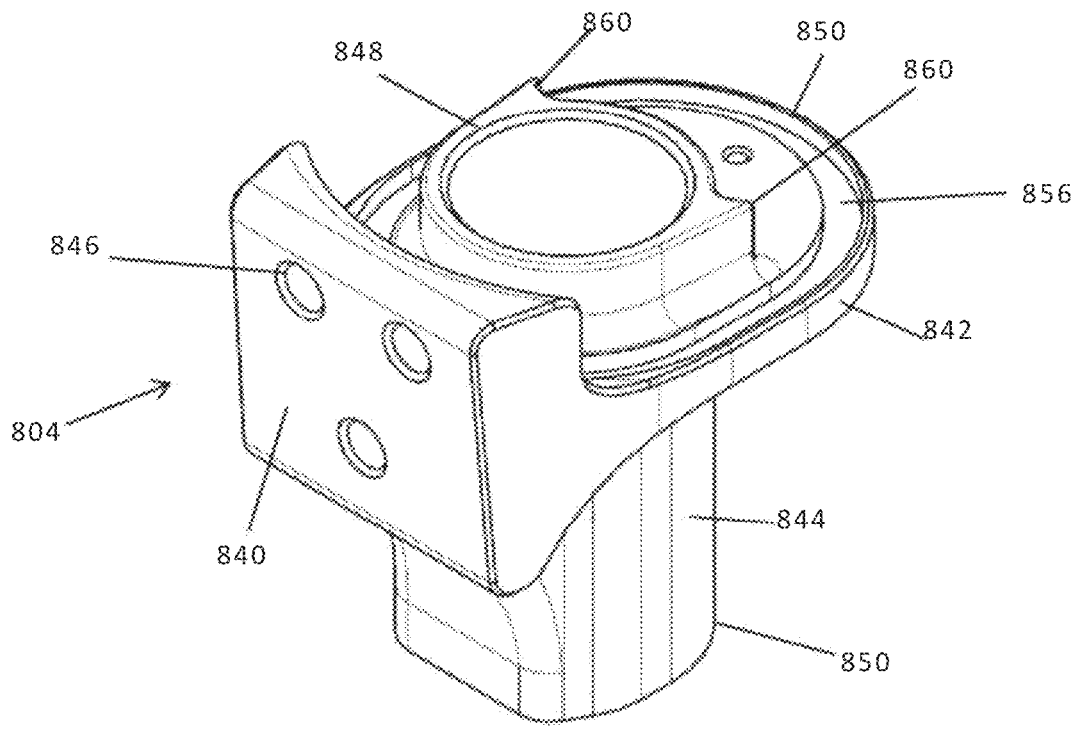
FIG. 12B is a perspective view representatively illustrating the lower member of the mounting bracket in accordance with exemplary embodiments of the present technology.
Figure 13:
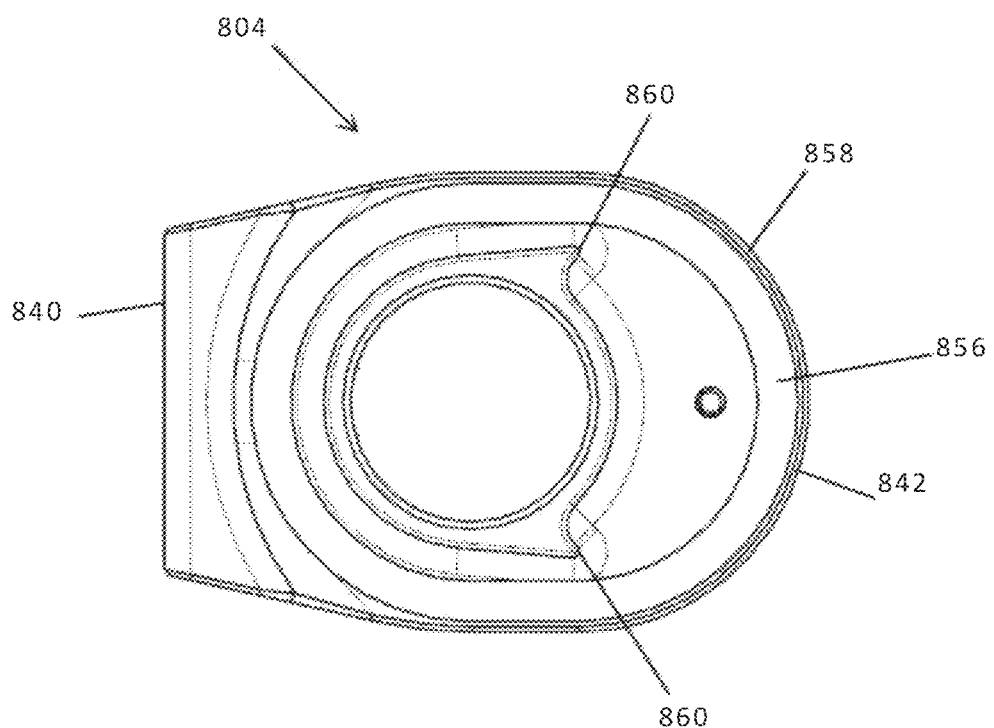
FIG. 13 is a top view representatively illustrating the lower member of the mounting bracket in accordance with exemplary embodiments of the present technology.

Referring now to FIGS. 12-13, in various embodiments, the lower member 804 may comprise a mounting portion 840, a lower flange 842, and a mating portion 844. The mounting portion 840 may be located at a rear edge of the lower flange 842. The mounting portion 840 may comprise at least one threaded aperture 846 used to couple the mounting bracket 800 to the prosthetic foot 100. (See FIGS. 8 and 9) In one embodiment, the mounting portion 840 comprises 3 threaded apertures 846 which receive bolts 864 to couple the mounting bracket 800 to the prosthetic foot 100.

In various embodiments, as shown in FIG. 9, an upper end 862 of the prosthetic foot 100 may be connected to the mounting portion 840 of the lower member 804 via mechanical connection whereby fasteners 864 are received within apertures (not shown) residing in the upper end 862 of the prosthetic foot 100 and the mounting portion 840 of lower member 804. While a bolted connection is shown any mechanical connection may be contemplated, such as screws, rivets, and the like. The bolted connection materials may comprise Titanium or any other suitable material. Other types of material may comprise mild steel, alloy steel, high strength stainless steel such as 13-8, and alloy aluminum such as the 2000 and 7000 series.

Figure 14A:
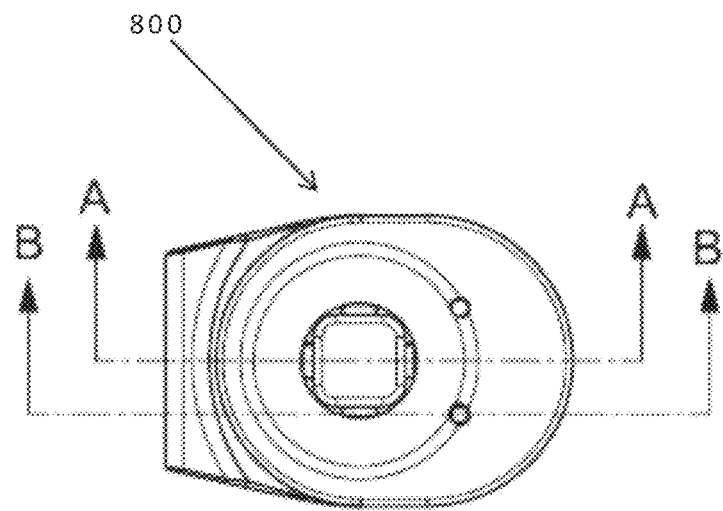
FIG. 14A is a top view representatively illustrating the mounting bracket in accordance with exemplary embodiments of the present technology.
Figure 14B:
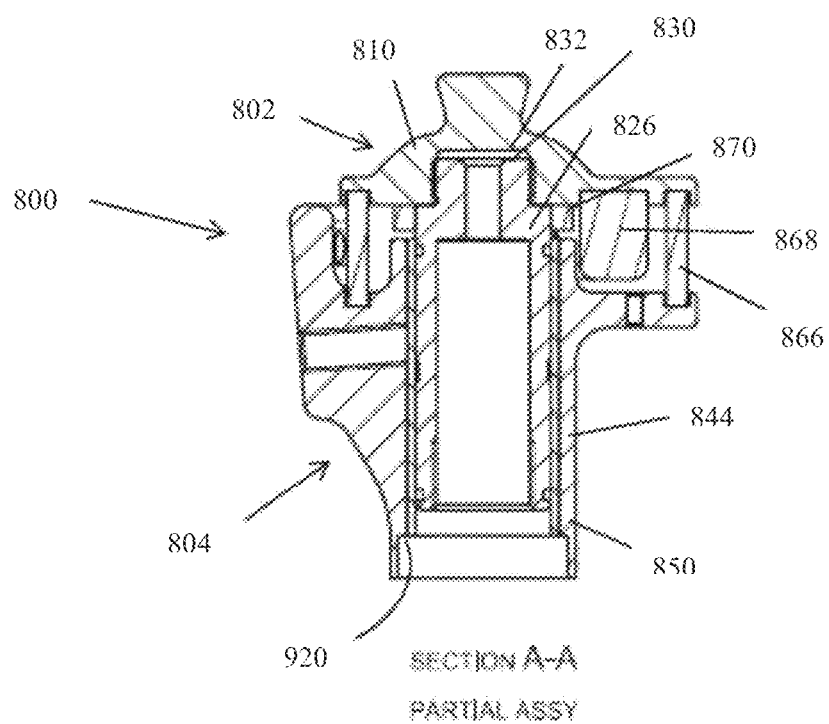
FIG. 14B is a partial, side, cross-section view taken along the line A-A in FIG. 14A representatively illustrating the mounting bracket in accordance with exemplary embodiments of the present technology.
Figure 15:
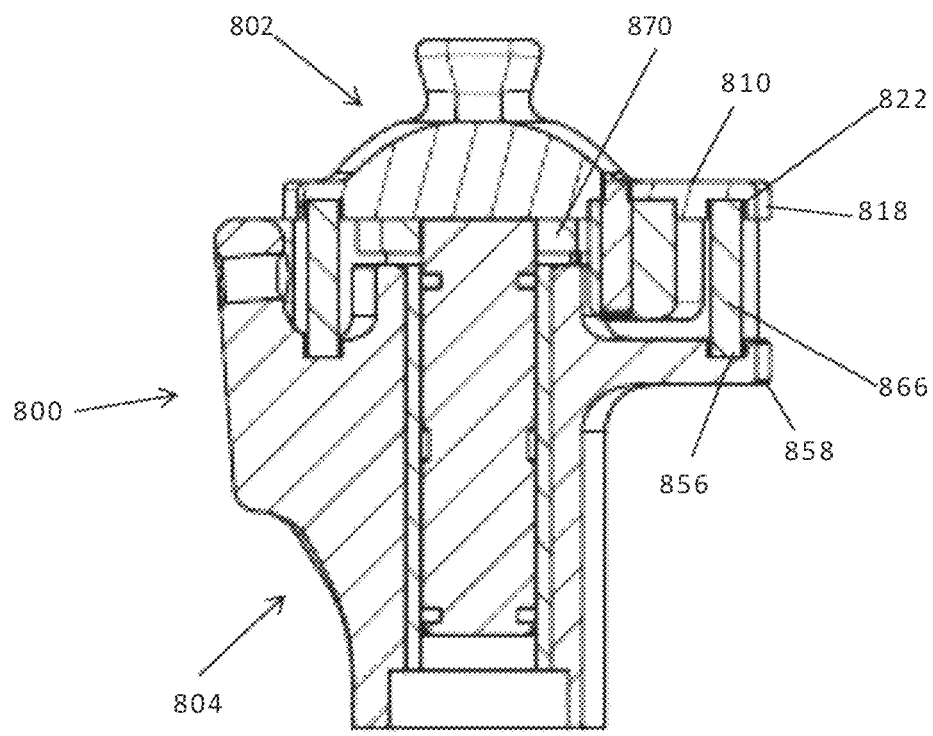
FIG. 15 is a partial, side, cross-section view taken along the line B-B in FIG. 14A representatively illustrating the mounting bracket in accordance with exemplary embodiments of the present technology.
Figure 16:
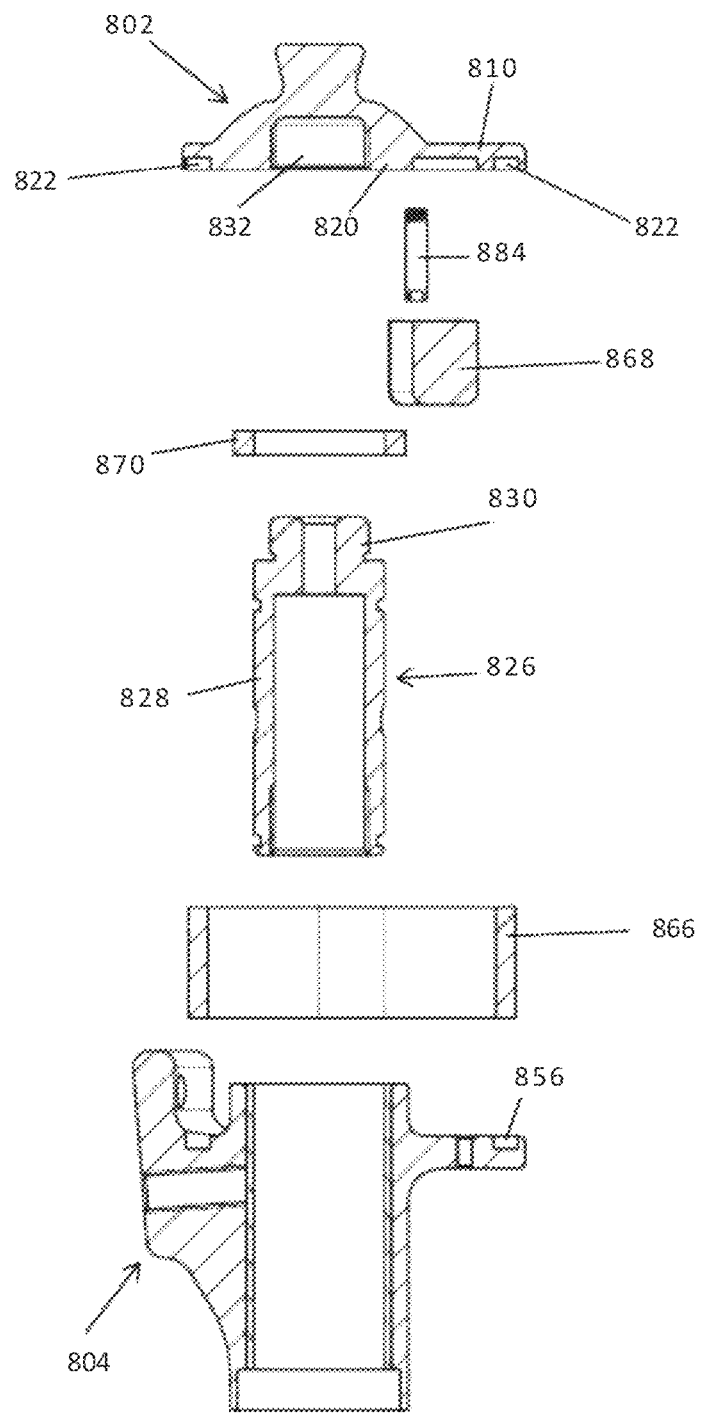
FIG. 16 is a partial, exploded, side, cross-section view taken along the line A-A in FIG. 14A representatively illustrating the mounting bracket in accordance with exemplary embodiments of the present technology.

The mating portion 844 of the lower member 804 may comprise an upper collar 848 and a lower collar 850. The upper collar 848 depends upwardly from an upper surface 852 of the lower flange 842 while the lower collar 850 depends downwardly from a lower surface 854 of the lower flange 842. As shown in FIGS. 12A-B and 14B, the upper and lower collars 848, 850 of the mating portion 844 combine to receive the cylindrical collar 828 of the mating post 826 of the upper member 802 when the upper and lower members 802, 804 are connected. As shown in FIGS. 12A, 12B, 13 and 15, the upper surface 852 of the lower flange 842 may comprise a recessed channel 856 and a lip 858 surrounding a portion of the perimeter.

In various embodiments, the lower member 804 may comprise a pair of stops 860. The stops 860 serve to limit rotation of the upper member 802 with respect to the lower member 804 during use as will be discussed in detail below.

Figure 32:
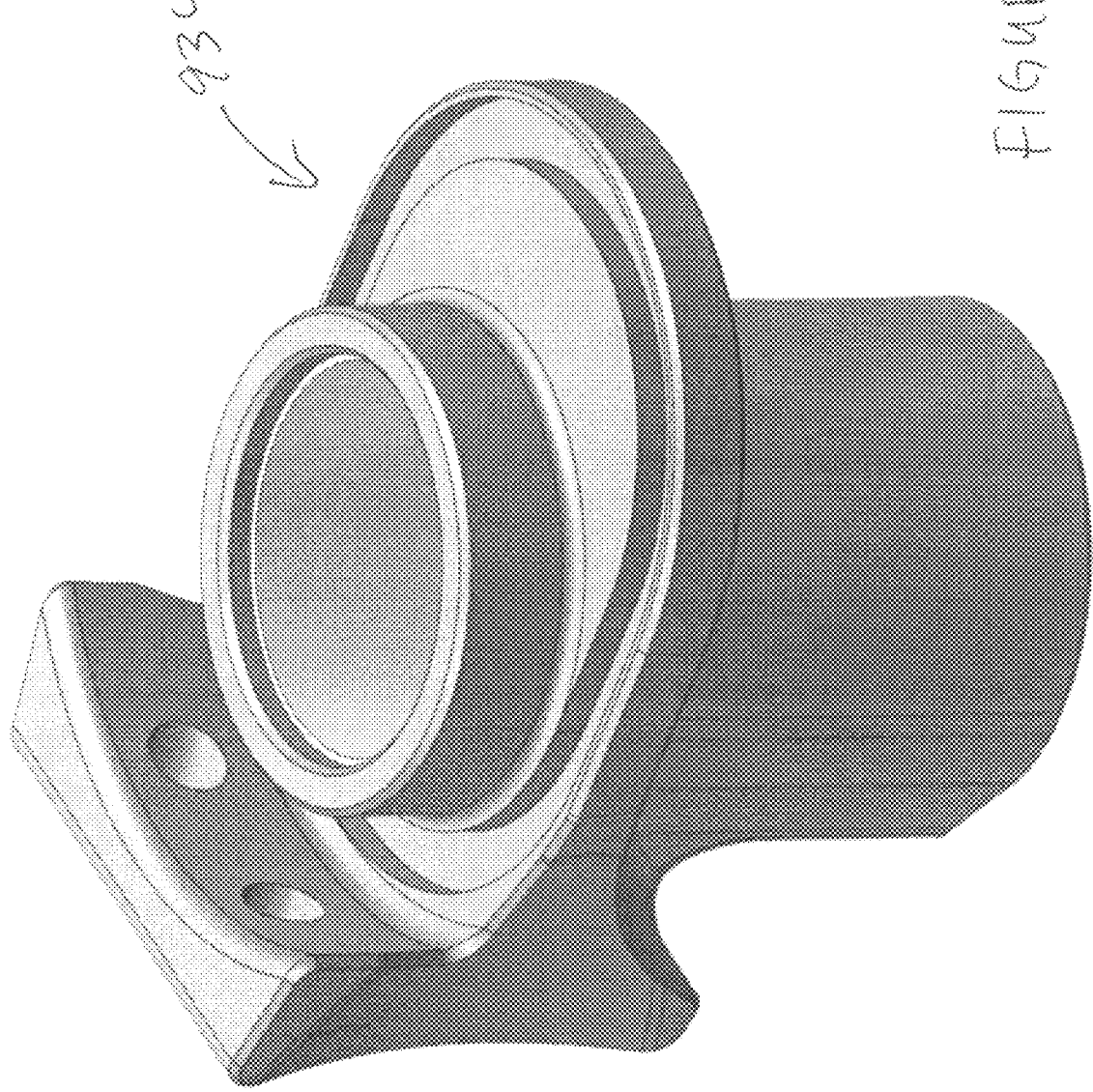
FIG. 32 is a perspective view representatively illustrating an additional embodiment of a lower member of the mounting bracket in accordance with exemplary embodiments of the present technology.

In another embodiment, shown in FIG. 32, a lower member 934 is provided without any stops. In this embodiment, the bumper 868 may function as a compression bumper and not a torsion bumper. The remainder of the lower member 934 is similar to lower member 804.

Referring now to FIGS. 9, 10, 16 and 19 in various embodiments, the compression torsion joint 806 may comprise an elastomeric ring 866. In various embodiments, the compression torsion joint 806 may comprise a bumper 868. In various embodiments, the compression torsion joint 806 may comprise a compression collar 870. In one embodiment, the compression torsion joint 806 may comprise a combination of the elastomeric ring 866, the bumper 868, and the compression collar 870.

Figure 19:
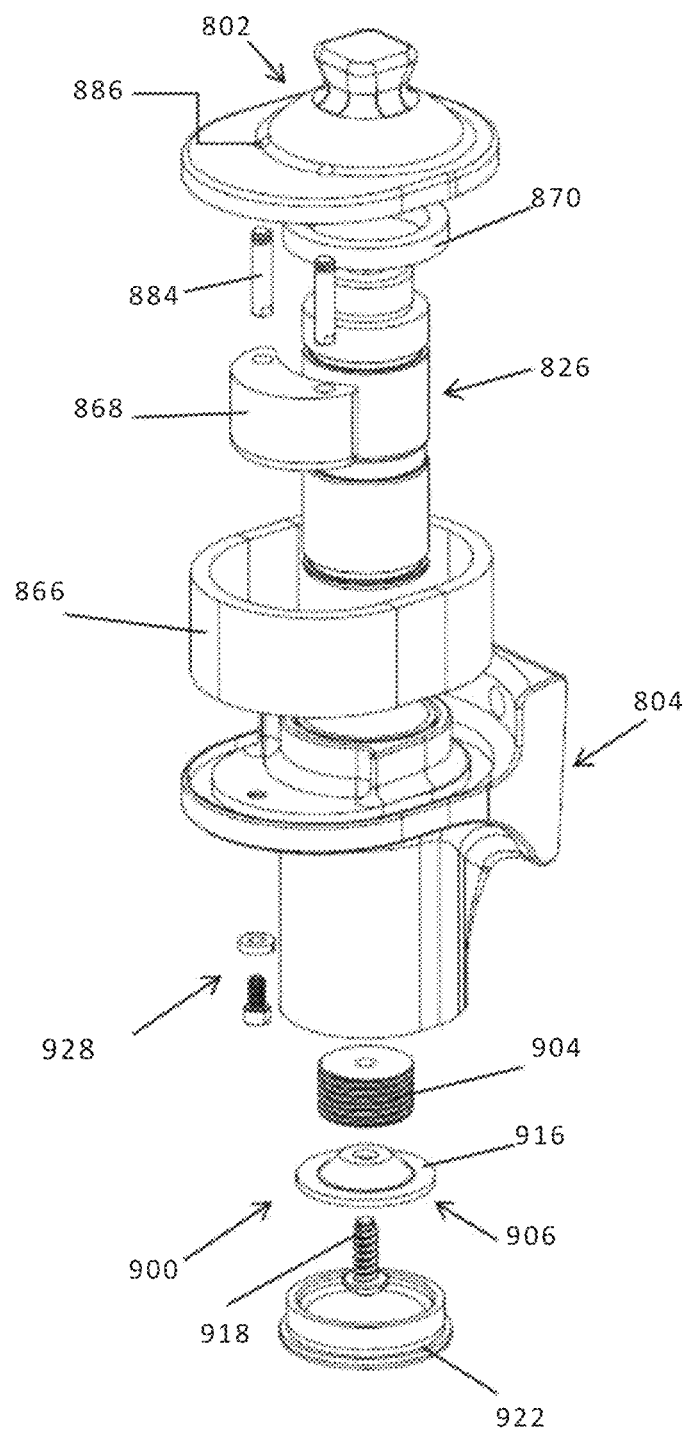
FIG. 19 is an exploded, perspective view representatively illustrating the mounting bracket of FIG. 10 in accordance with exemplary embodiments of the present technology.
Figure 22A:
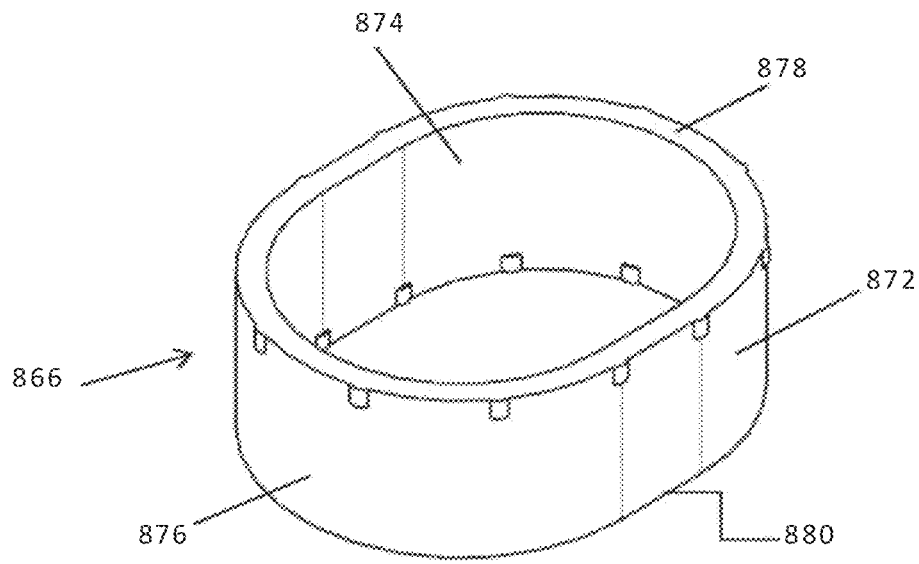
FIG. 22A is a perspective view representatively illustrating an elastomeric ring of the mounting bracket in accordance with exemplary embodiments of the present technology.
Figure 22B:
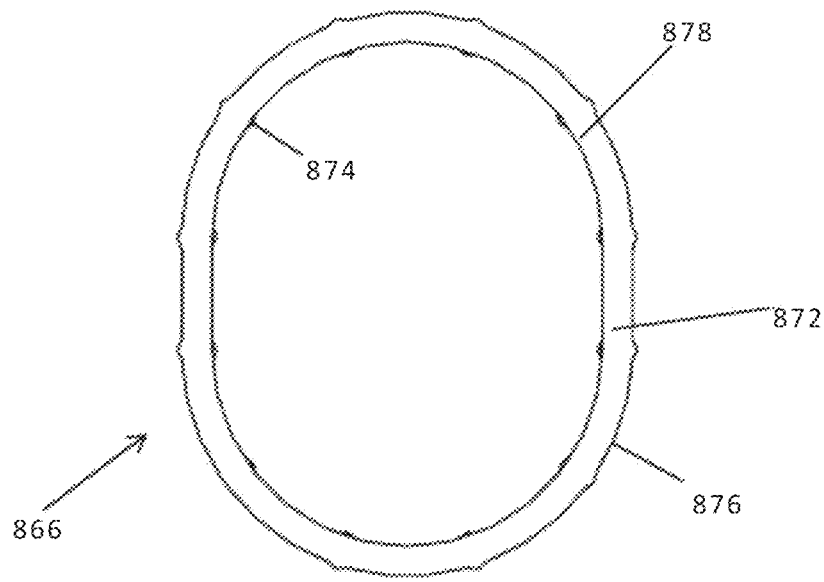
FIG. 22B is a top view representatively illustrating the elastomeric ring of the mounting bracket in accordance with exemplary embodiments of the present technology.

Referring to FIGS. 19, 22A and 22B, the elastomeric ring 866 may comprise a wall 872 with inner 874, outer 876, upper 878, and lower 880 surfaces. In one embodiment, shown in FIGS. 22A and 22B, the inner surface 874 of the wall 872 comprises a substantially smooth surface. In one embodiment, the inner surface 874 may comprise a ridged surface, a surface with raised portions, and or a wall with varying thickness. In one embodiment, the inner and outer surfaces 874, 876 may be curved from the upper 878 to lower surface 880, and/or convex with respect to the center of the elastomeric ring 866. In one embodiment, the outer surface 876 may be curved, and/or convex with respect to the center of the elastomeric ring 866. Referring now to FIGS. 11C, 13, 15, and 22A the upper surface 878 of the elastomeric ring 866 may be received in the channel 822 in the upper flange 810 in the upper member 802. The outer surface 876 generally abuts the lip 818 of the upper flange 810 of the upper member 802. The lower surface 880 of the elastomeric ring 866 may be received in the channel 856 in the lower flange 842 in the lower member 804. The outer surface 876 generally abuts the lip 858 of the lower flange 842 of the lower member 804.

Figure 28A:
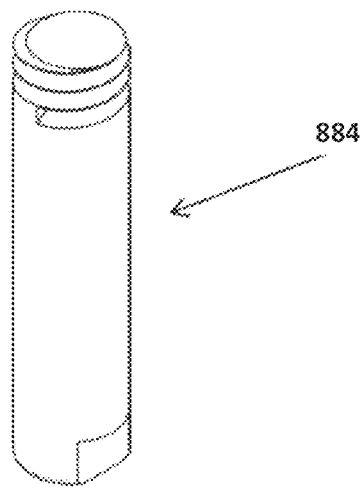
FIG. 28A is a perspective view representatively illustrating a pin of the mounting bracket in accordance with exemplary embodiments of the present technology.
Figure 28B:
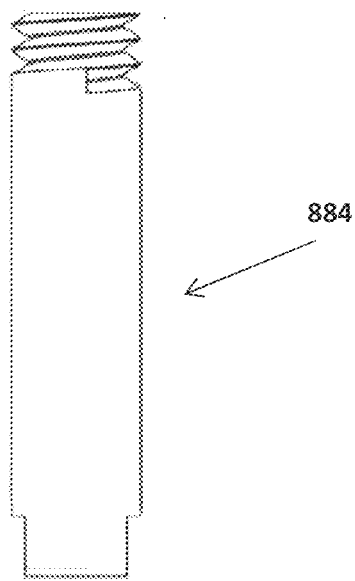
FIG. 28B is a side view representatively illustrating the pin of the mounting bracket in accordance with exemplary embodiments of the present technology.

In one embodiment, shown in FIGS. 17, 19, and 23A-C, the compression torsion joint 806 may comprise a bumper 868. In one embodiment, the bumper 868 may comprise a compression/torsion bumper. In another embodiment, the bumper 868 may comprise a compression bumper. The bumper 868 may be crescent shaped and received within the crescent-shaped recess 824 of the upper flange 810 of the lower member 804 (See FIG. 11C). An upper surface 881 of the bumper 868 may be received in and bonded within the crescent-shaped recess 824 in the manner described below with respect to the elastomeric ring 866. In use, a lower surface 882 of the bumper 868 will contact the upper surface 852 of the lower flange 842 thereby only allowing a limited amount of vertical movement of the upper member 802 with respect to the lower member 804 (See FIGS. 12A-B). The bumper 868 limits the vertical movement while the elastomeric ring 866 provides vertical shock absorption during the gate cycle and while standing. In one embodiment, the 868 may comprise a pair of holes 883 that receive pins 884 (See FIGS. 28A-B). The pins 884 may comprise at least partially threaded shafts that are received in a pair of threaded holes 886 within the upper member 802. In one embodiment, the stops 860 in conjunction with the bumper 868 and the pins 884 serve to limit the torsional rotation of the upper member 802 with respect to the lower member 804 during use. When used in combination with the stops 860, the bumper 868 is a compression/torsion bumper. In the embodiment discussed above, where the stops are absent from the lower member, the bumper 868 may function as a compression bumper and not a torsion bumper.

Figure 17:
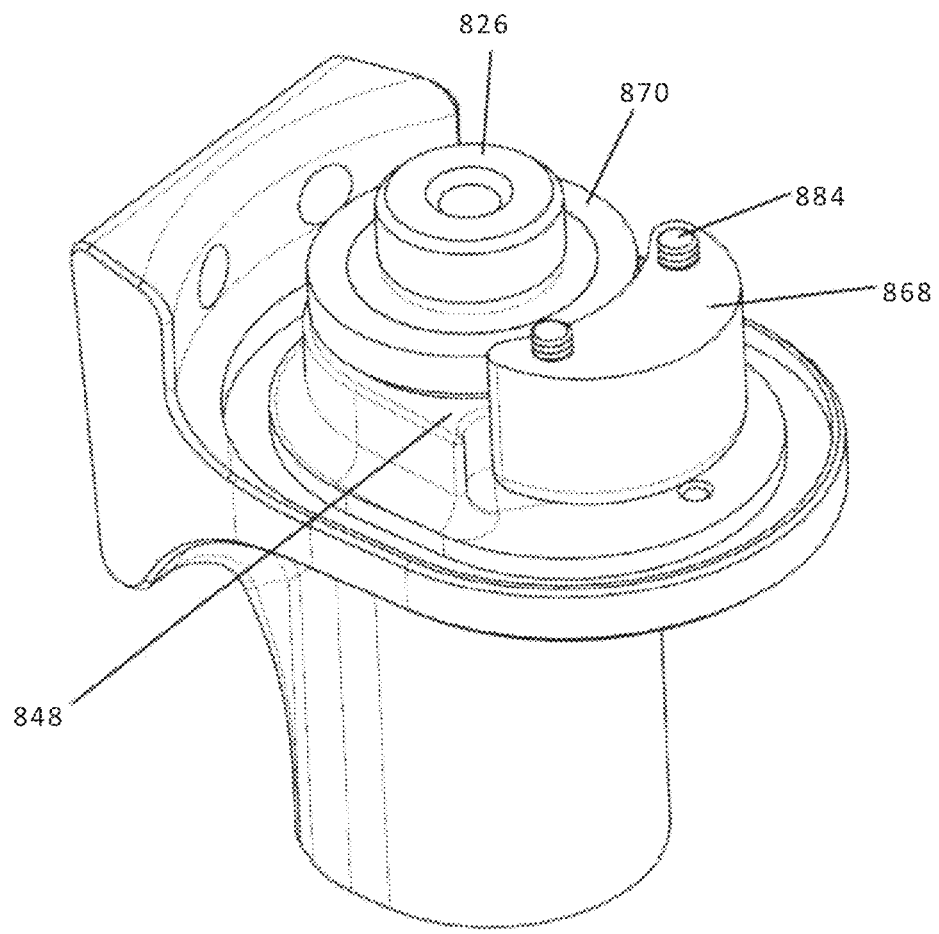
FIG. 17 is a perspective view representatively illustrating the lower member of the mounting bracket with a compression collar and a compression/torsion bumper in accordance with exemplary embodiments of the present technology.
Figure 18:
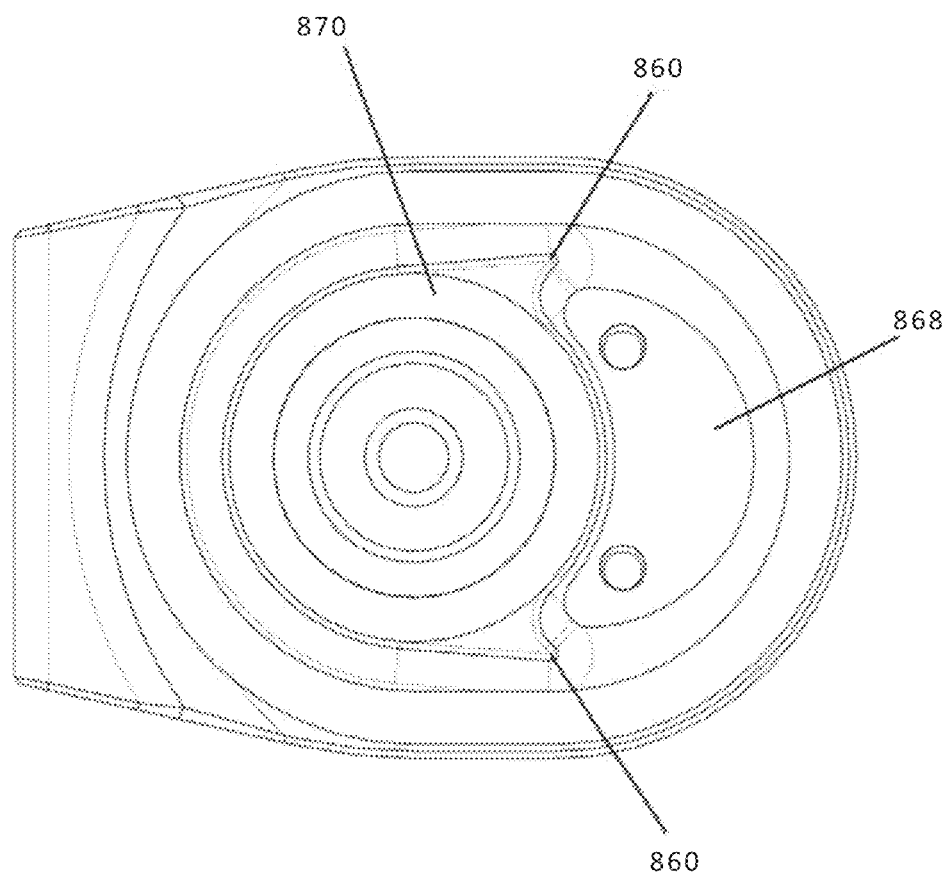
FIG. 18 is a top view representatively illustrating lower member of the mounting bracket with a compression collar and a compression/torsion bumper in accordance with exemplary embodiments of the present technology.
Figure 24A:
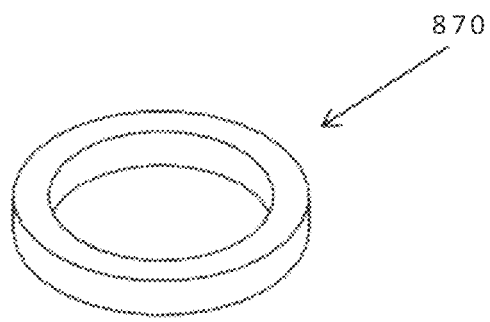
FIG. 24A is a perspective view representatively illustrating a compression collar of the mounting bracket in accordance with exemplary embodiments of the present technology.
Figure 24B:
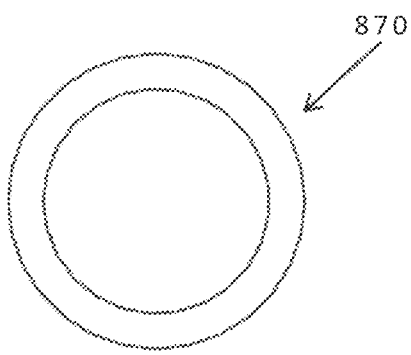
FIG. 24B is a top view representatively illustrating the compression collar of the mounting bracket in accordance with exemplary embodiments of the present technology.
Figure 25:
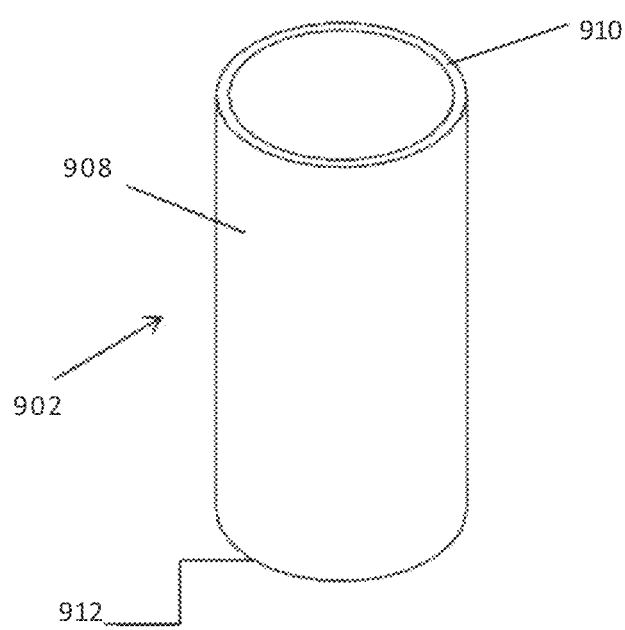
FIG. 25 is a perspective view a sleeve of the mounting bracket in accordance with exemplary embodiments of the present technology
Figure 26A:
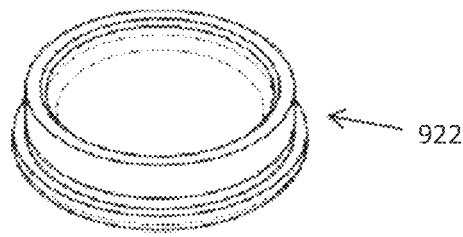
FIG. 26A is a perspective view representatively illustrating a cap of the mounting bracket in accordance with exemplary embodiments of the present technology.
Figure 26B:
FIG. 26B is a side view representatively illustrating the cap of the mounting bracket in accordance with exemplary embodiments of the present technology.
Figure 26C:
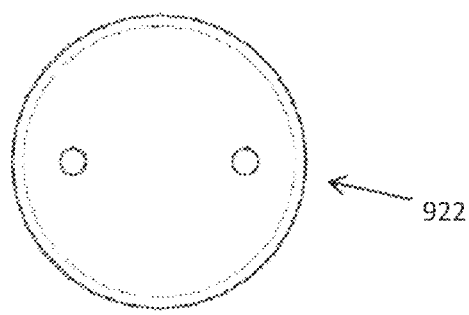
FIG. 26C is a bottom view representatively illustrating the cap of the mounting bracket in accordance with exemplary embodiments of the present technology.

In various embodiments, as shown in FIGS. 17, 19, and 24 and a compression collar 870 may be received on the cylindrical collar 826 and abut the lower surface 820 of the upper flange 810. In one embodiment, when assembled, a gap may exist between the lower surface of the compression collar 870 and an upper surface of the upper collar 848. A gap may also exist between a lower surface of bumper 868 and the upper surface of the lower flange 842. In another embodiment, when assembled, the lower surface of the compression collar 870 may abut an upper surface of the upper collar 848.

Figure 29:
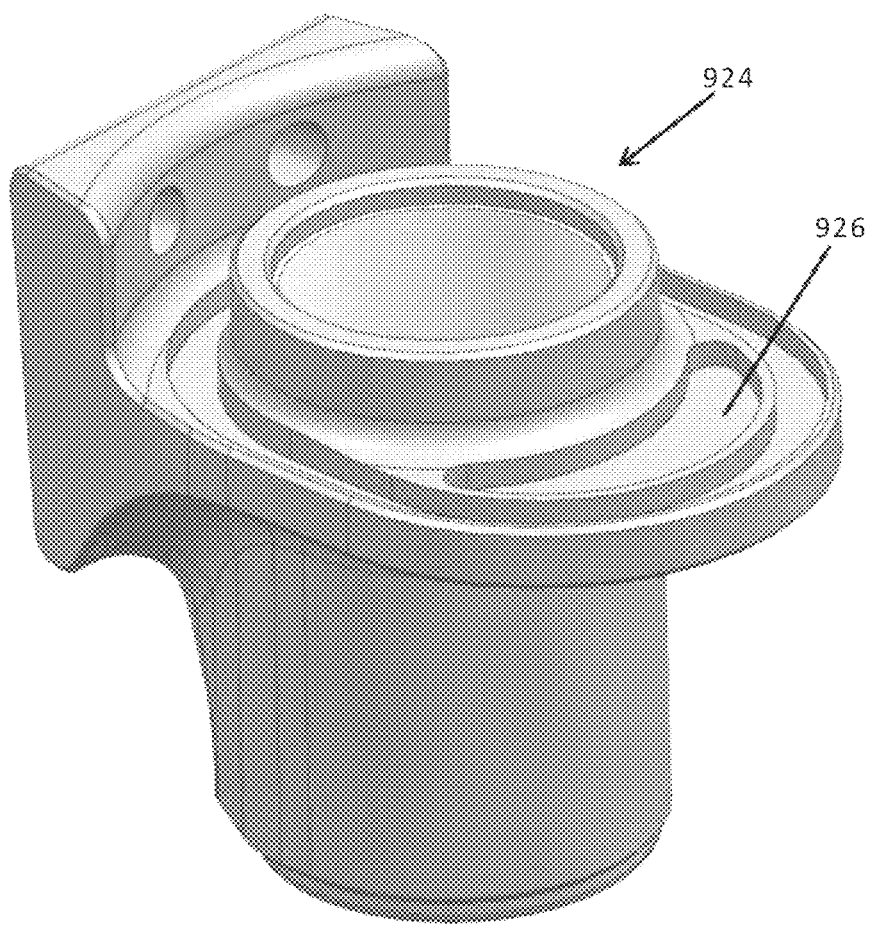
FIG. 29 is a perspective view representatively illustrating an additional embodiment of a lower member of the mounting bracket in accordance with exemplary embodiments of the present technology.
Figure 30:
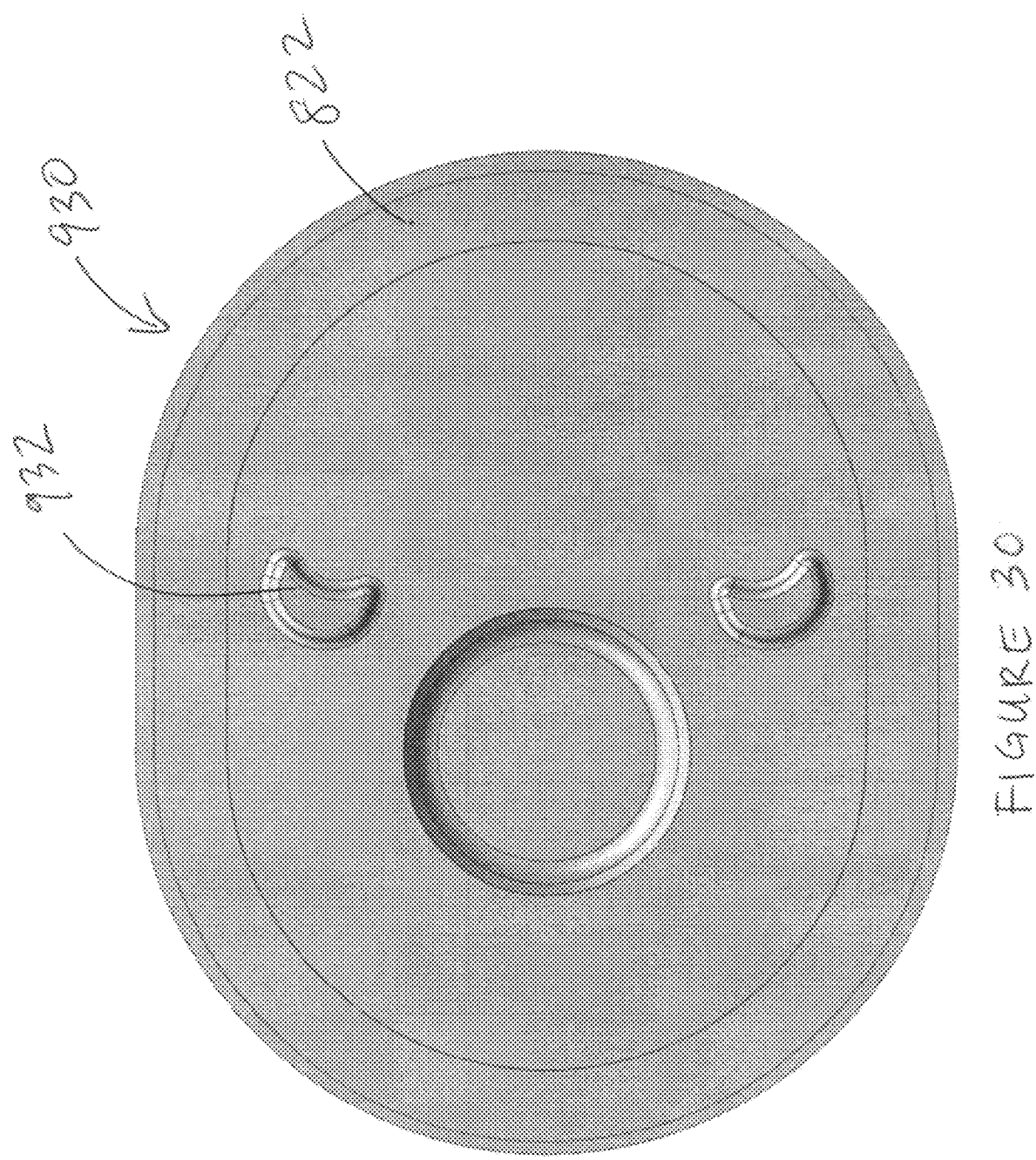
FIG. 30 is a bottom view representatively illustrating an additional embodiment of an upper member of the mounting bracket in accordance with exemplary embodiments of the present technology.
Figure 31:
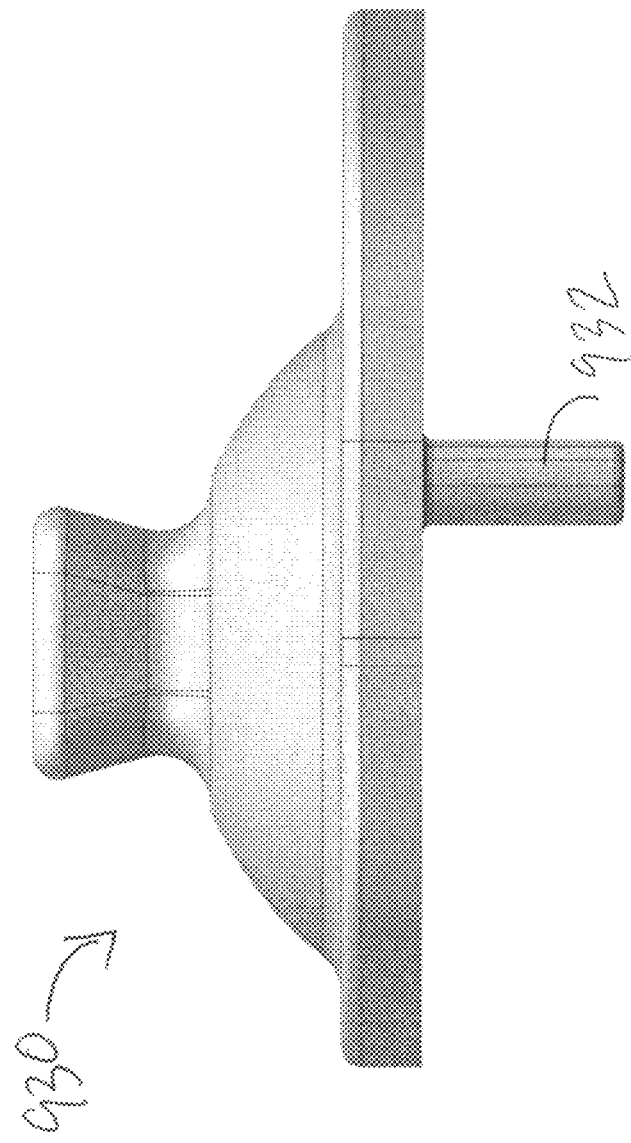
FIG. 31 is a side view representatively illustrating an additional embodiment of the upper member of the mounting bracket in accordance with exemplary embodiments of the present technology.

In another embodiment, referring to FIG. 29, a lower member 924 is shown having a crescent-shaped recess 926. The lower surface 882 of the bumper 868 may be received in and bonded within the crescent-shaped recess 926 in the manner described below with respect to the bonding of the elastomeric ring 866. Referring to FIGS. 30 and 31, in one embodiment, an upper member 930 is shown comprising a pair of stops 932 and channel 822. In this embodiment, the bumper 868 is a compression/torsion bumper. The remainder of upper member 930 is similar to the upper member 802 but without a crescent-shaped recess. This embodiment, shown in FIGS. 29-31, operates similarly to the embodiment discussed above of the lower member 804 having the stops 860 and the upper member 802 having the crescent-shaped recess 824.

Referring now to FIGS. 9 and 12A-B, in various embodiments, the mounting bracket 800 may comprise a washer plate 888. The washer plate 888 may be used when coupling the mounting bracket 800 to the upper end 862 of the prosthetic foot 100. The washer plate 888 may comprise the same number of apertures as the upper end 862 of the prosthetic foot 102 and the mounting portion 840 of the lower member 804. The washer plate 888 is designed to spread the load and reduce the stress concentration across the surface of the upper end 862 of the prosthetic foot 100. In another embodiment, the prosthetic foot 100 may also utilize standard washer configurations.

Referring now to FIGS. 19-21 and 25, in various embodiments, the mounting bracket 800 may comprise a retention system 900. The retention system 900 is utilized as a failsafe to ensure that the upper member 802 does not disconnect from the lower member 804 in the situation where the bond on the elastomeric ring 866 that connects the upper and lower members 802, 804 fails. In various embodiments, the retention system 900 may comprise a sleeve 902, a plug 904, and a connector 906.

In various embodiments, the sleeve 902 may comprise a cylindrical wall 908 and first and second ends 910, 912. The sleeve 902 fits within the mating portion 844 of the lower member 804. The sleeve 902 may be inserted at a lower end of the lower member 804 and may extend along the length of the mating portion 844. The first end 910 of the sleeve 902 may abut a lip formed in the interior of the upper collar 848 of the lower member 804. The lip is configured to retain the first end 910 within the mating portion 884.

In various embodiments, the plug 904 contains threads which are received within internal threads located in the internal wall 914 in the cylindrical collar 828 of the mating post 826. The connector 906 may be used in conjunction with the mating post 826, which is received within the sleeve 902, to couple the upper member 802 to the lower member 804. The sleeve 902 may comprise a low-friction material that facilitates smooth movement between the upper and lower members 802, 804. The connector 906 may comprise a retention washer 916 and a retention connector 918. The retention connector 918 is used in conjunction with the retention washer 916 and is received within a threaded aperture in the plug 904. When tightened, the retention connector 918 seats the retention washer 916 against an internal shelf 920 in the lower member 804 (See FIGS. 14B, 20B, and 21). In one embodiment, the retention connector 918 is a screw.

Figure 20A:
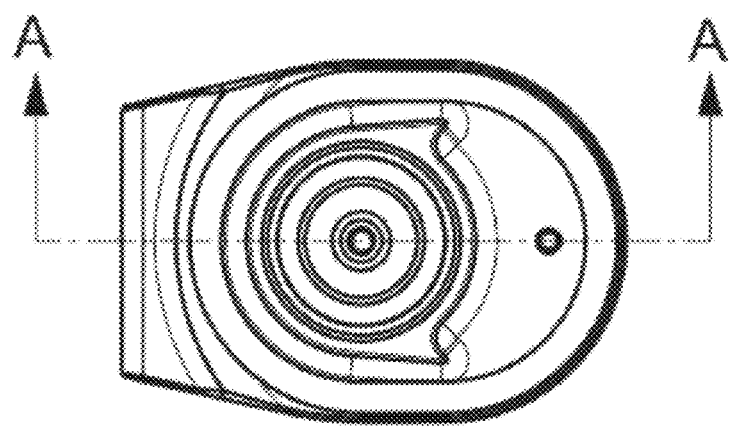
FIG. 20A is a top, partially assembled, lower member view representatively illustrating portions of the mounting bracket in accordance with exemplary embodiments of the present technology.
Figure 20B:
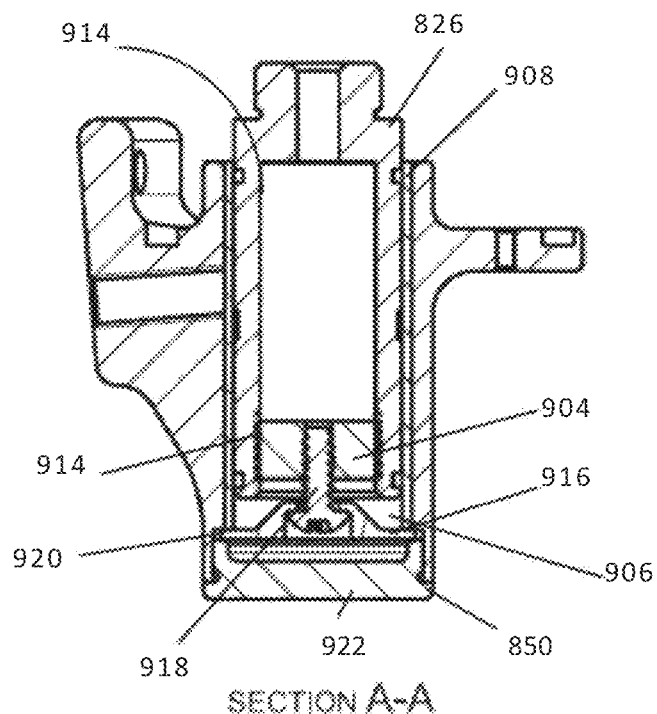
FIG. 20B is a partial, side, cross-section view taken along the line A-A in FIG. 20A representatively illustrating portions of the mounting bracket in accordance with exemplary embodiments of the present technology.
Figure 21:
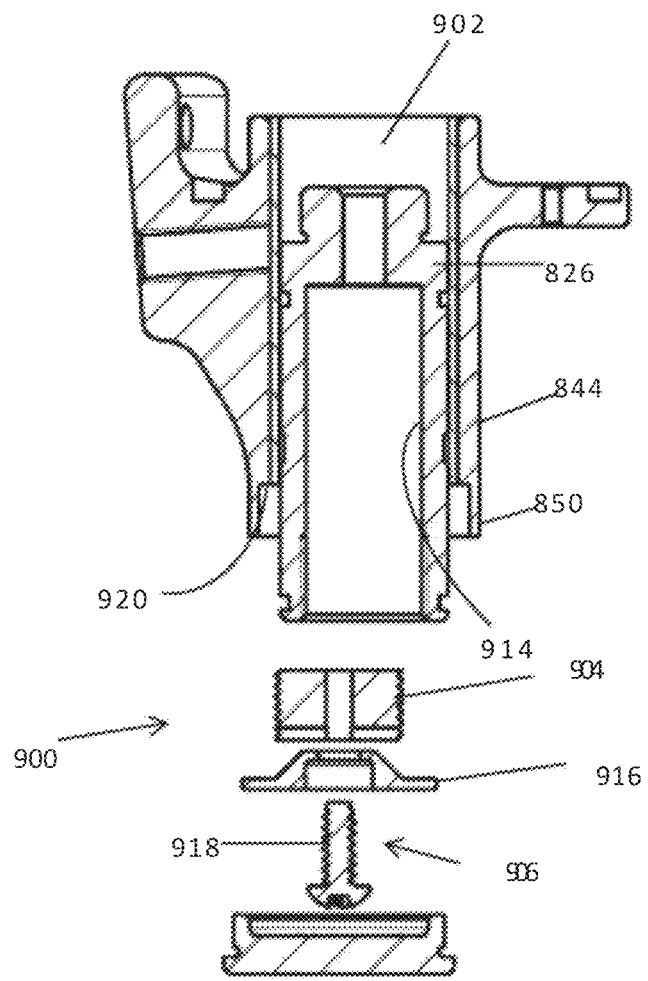
FIG. 21 is a partial, exploded side, cross-section view taken along the line A-A in FIG. 20A representatively illustrating portions of the mounting bracket in accordance with exemplary embodiments of the present technology

In various embodiments, referring now to FIGS. 19, 20B, and 21 the retention system 900 may comprise a cap 922. The cap 922 retains the second end 912 of the sleeve 902 within the lower collar 850 of the mating portion 844. The cap 922 may be press fit or may contain threads that mate with internal threads (not shown) in the lower collar 850 of the mating portion 844. In use, the cylindrical collar 828 of the mating post 826 is received within the sleeve 902, which is received in the upper and lower collars 848, 850 of the mating portion 844 when the upper and lower members 802, 804 are connected.

The cap 922 may butt up against the retention washer 916 pressing it against the second end 912 of the sleeve 902. The cap 922 also seats the spacer within the mating portion 844 and keeps dirt, sand, or small objects from entering the mating portion 844 of the lower member 804. Objects such as small rocks or sand could wear away the moving internal members eventually causing damage or failure.

The sleeve 902 may be made from any suitable low-friction material. In one embodiment the low friction sleeve is made from plastic to allow for smooth movement between the components of the prosthetic foot. In one embodiment a low coefficient plastic bushing material may be used.

In various embodiments, the mounting bracket 800 may comprise a vent assembly 928. In one embodiment the vent assembly 928 may comprise a screw, a washer and an aperture in the lower member 804. The screw is received within the aperture in the lower member 804. Removal of the screw from the aperture in the vent assembly 928 may be used to equalize pressure (during adhesive bond cure) inside the mounting bracket 800 with the ambient surrounding pressure. Without this vent assembly 928, pressure builds up inside the cavity in mounting bracket 800 and forces the metal components to partially separate from the elastomeric ring 866.

In use under load, a lower surface of the bumper 868 will contact the upper surface of the lower flange 842 in conjunction with compression collar 870 thereby only allowing a limited amount of vertical movement of the upper member 802 with respect to the lower member 804. The compression collar 870 limits vertical movement. The bumper 868 limits the vertical and torsional movement when used with an upper or lower member having stops. The bumper 868 limits the vertical movement when used with an upper or lower member without stops. The elastomeric ring 866 provides vertical shock absorption and torsional stability during the gate cycle and while standing.

The mounting bracket 800 provides a multi-phase system. When the initial load is applied to the prosthetic foot 100, the elastomeric ring 866 provides both a soft resistance for vertical compression and torsional rotation. Once a larger load is applied, the lower surface 882 of the bumper 868 will contact an upper surface 852 of the lower flange 842 and the lower surface of the compression collar 870 will contact an upper surface of the upper collar 848, thereby only allowing a limited amount of vertical movement of the upper member 802 with respect to the lower member 804. The bumper 868 and compression collar 870 limit the vertical movement while the elastomeric ring 866 provides vertical shock absorption during the gate cycle and while standing.

When a greater torsional load is applied, the elastomeric ring 866 gives increasingly stiff torsional stability until the bumper 868 contacts the stops 860 to limit the amount of torsional rotation. In one embodiment, the bumper 868 and the stops 860 serve to restrict the torsional rotation approximately 5-10 degrees. In one embodiment, the bumper 868 and the stops 860 serve to restrict the torsional rotation approximately plus or minus 8 degrees.

In various embodiments, the elastomeric ring 866 may comprise a lower durometer than the bumper 868 and compression collar 870 thereby providing an initial soft resistance to vertical load and torsional rotation. The higher durometer compression collar 870 provides a greater resistance during high vertical loads. The compression collar 870 can comprise different heights that affect the sensation of the mounting bracket 800 during vertical compression. If the compression collar 870 is taller, it can make contact before the bumper 868. The higher durometer bumper 868 provides a greater resistance during high loads both vertically and torsionally. Thus, the system described above may provide multi-phase resistance to vertical loading and torsional rotation based on the user's needs.

According to various embodiments the upper and lower members 802, 804 may be made from Titanium (any type) or any other suitable material. In one embodiment the upper member 802 may comprise titanium. In one embodiment the lower member 804 may comprise alloy aluminum. Some other types of material that may be used for the upper and lower members 802, 804 comprise mild steel, alloy steel, steel, high strength stainless steel such as 13-8, alloy aluminum such as the 2000 and 7000 series, and any suitable composite material.

In various embodiments, the upper and lower members 802, 804 described above can be an integral piece or multiple pieces joined together by any suitable method. In some embodiments, depending on the type of material, the upper and lower members 802, 804 may be fabricated by milling, casting, forging, powdered metal, and the like. In one embodiment, the upper and lower members 802, 804 may be fabricated on a titanium CNC milling machine. More specifically, in one embodiment the upper and lower members 802, 804 may be unitary made from alloy aluminum fabricated using a CNC milling machine. In other embodiments, the aluminum, titanium, magnesium or other suitable material for the upper and lower members 802, 804 may be fabricated using a CNC milling machine. In other embodiments, the aluminum, titanium, magnesium or other suitable for the upper and lower members 802, 804 may be fabricated by casting, forging, powdered metal, and the like. In other embodiments, a chrome moly, steel, or other suitable material for the upper and lower members 802, 804 can be made from multiple pieces and coupled together by welding or any other suitable method According to various embodiments and referring to FIGS. 10-12, and 22 the upper and lower members 802, 804 may be coupled by the elastomeric ring 866. The elastomeric ring 866 may comprise any rubber, polyurethane, and/or elastomeric materials. The elastomeric ring 866 may be bonded to the upper and lower members 802, 804 using an adhesive. The upper surface 878 of the elastomeric ring 866 may be received in and bonded within the channel 822 in the upper flange 810 in the upper member 802. The lower surface 880 of the elastomeric ring 866 may be received in and bonded the channel 856 in the lower flange 842 in the lower member 804. The elastomeric ring 866 may act as a shock for absorbing force on the downward strike during the user's stride.

In various embodiments, the elastomeric ring 866 may comprise an adhesive bonding and thus coupling the lower member to the upper member. Further, the adhesive bonding of the elastomeric ring 866 may produce distributed stresses. Though other modulus values are contemplated, and various moduli may be used as well, a stiffer adhesive is preferred compared to a flexible adhesive. The elastomeric ring 866 creates a space between the upper flange 810 of the upper member 802 and the lower flange 842 of the lower member 106. The adhesive may be commingled with the elastomeric ring 866.

The prosthetic foot 100 can be adjusted to accommodate a user in part by adjusting characteristics of the elastomeric ring 866 between the upper member 802 and lower member 804. For example, in various embodiments, the durometer of the elastomeric ring 866 can be increased for users with more heel strike force, which may be caused by additional weight or dynamic activity.

In various embodiments and as shown the elastomeric ring 866 and bumper 868 may comprise an elastomeric material. The elastomeric material may comprise a general elastomeric material, polyurethane, natural rubber, a synthetic rubber, or various combinations of natural and synthetic rubber. The durometer of the elastomeric material of both the elastomeric ring 866 and bumper 868 may be varied to provide additional adjustment of the prosthetic foot. The elastomeric material of the elastomeric ring 866 and bumper 868 supports load. Further, since the elastomeric ring 866 couples the upper and lower members 802, 804, the members are capable of torsional rotation during use of the prosthetic foot 100. The adjustable durometer of the elastomeric material allows the adjustment of the spring rate of the elastomeric ring based on user needs such as activity level, compliance level, weight changes, and the like. For example, in various embodiments, the durometer of the elastomeric material can be increased for users with more heel strike force, which may be caused by additional weight of the user or dynamic activity of the user. Increased heel strike force also provides greater compression of the heel member. As stated above the elastomeric ring 866 may comprise a lower durometer than the bumper 868 thereby providing an initial soft resistance to vertical load and torsional rotation. The higher durometer bumper 868 provides a greater resistance during high loads both vertically and torsionally.

In another embodiment, referring to FIG. 29, a lower member 924 is shown having a crescent-shaped recess 926. The lower surface 882 of the bumper 868 may be received in and bonded within the crescent-shaped recess 926 in the manner described below with respect to the bonding of the elastomeric ring 866. Referring to FIGS. 30 and 31, in one embodiment, an upper member 930 is shown comprising a pair of stops 932 and channel 822. In this embodiment, the bumper 868 is a compression/torsion bumper. The remainder of upper member 930 is similar to the upper member 802 but without a crescent-shaped recess. This embodiment, shown in FIGS. 29-31, operates similarly to the embodiment discussed above of the lower member 804 having the stops 860 and the upper member 802 having the crescent-shaped recess 824.

In accordance with various embodiments and with reference to FIGS. 8-10, the connection point 130 may comprise a mounting bracket 800. The mounting bracket 800 may be attached to the top member 120 and configured for attachment to a user. In various embodiments, the mounting bracket 800 may comprise an upper member 802, a lower member 804, and a compression torsion joint 806. The upper member 802 may be configured for attachment to a user's residual limb. The lower member 804 may be configured to attach to a prosthetic foot. In one embodiment the lower member 804 is coupled to the prosthetic foot 100.

Figure 33:
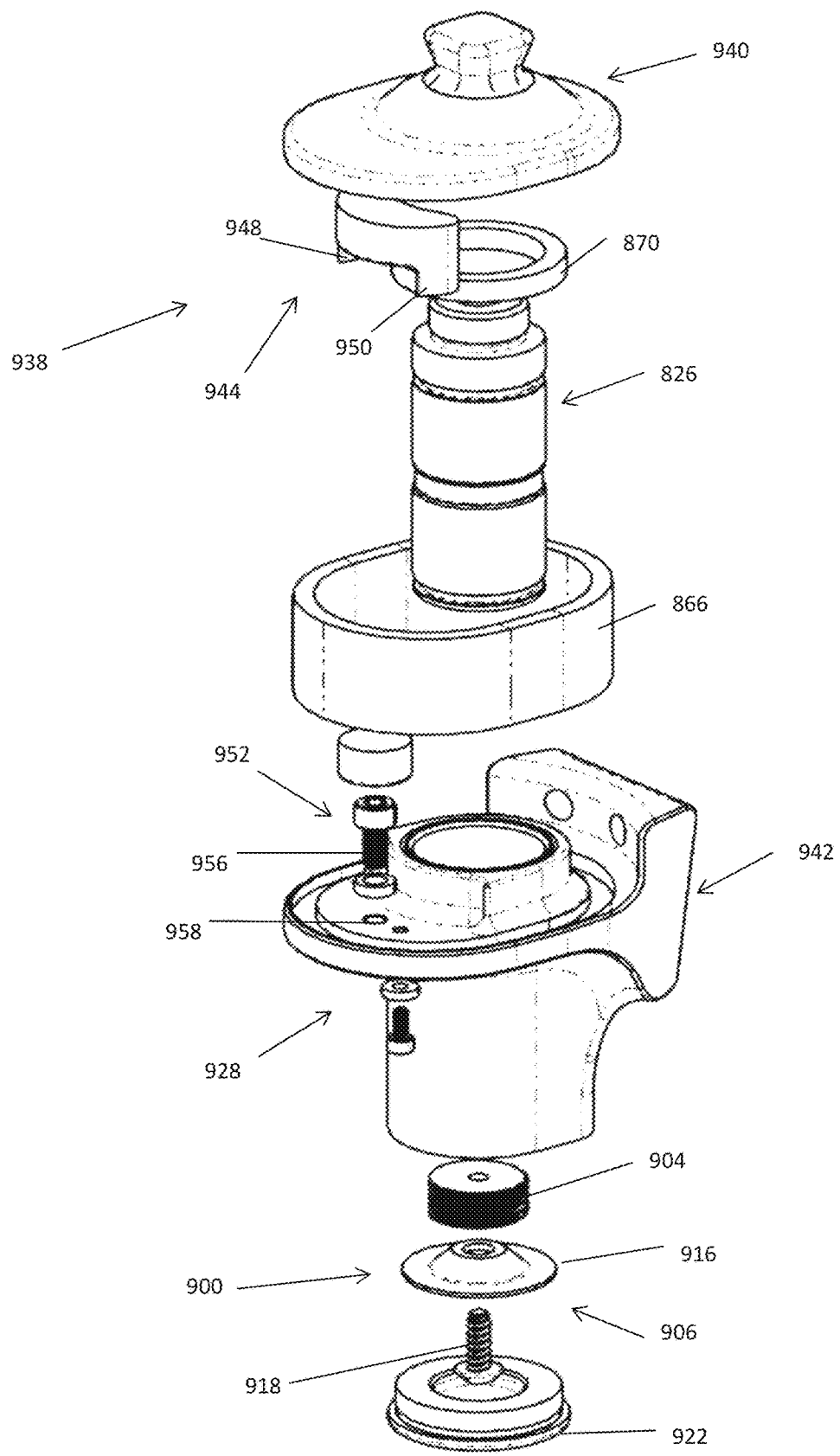
FIG. 33 is an exploded, perspective view representatively illustrating an additional embodiment of the mounting bracket with an additional embodiment of a compression torsion joint in accordance with exemplary embodiments of the present technology.
Figure 34:
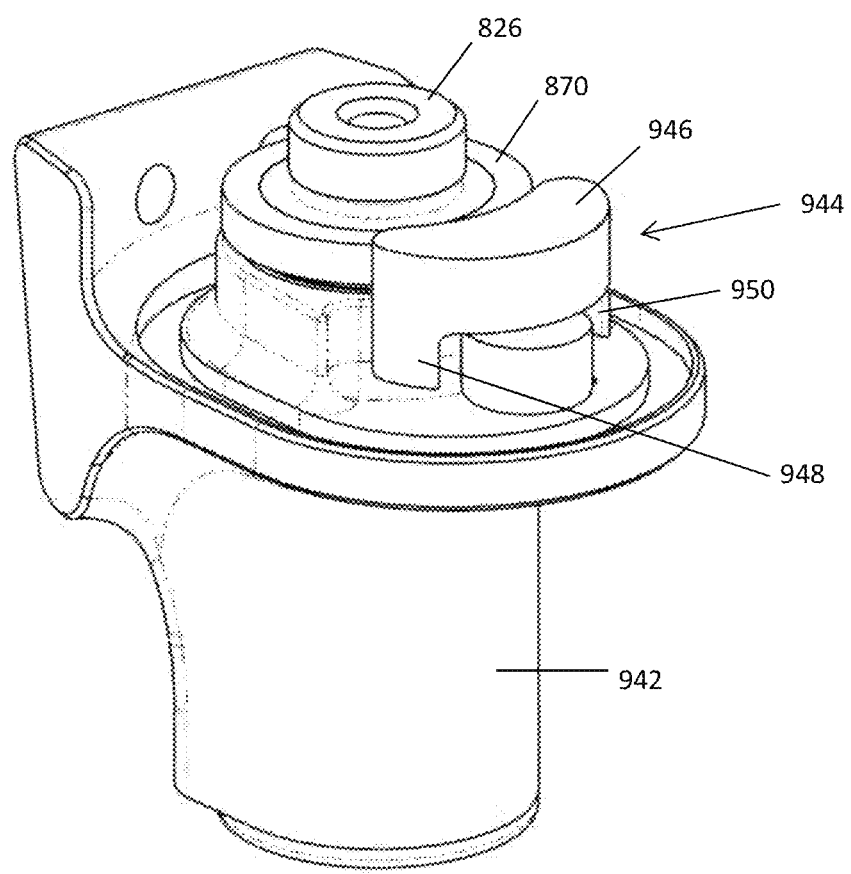
FIG. 34 is a perspective view of the lower member of the mounting bracket with new components for the compression torsion joint of FIG. 33 in accordance with exemplary embodiments of the present technology.
Figure 35:
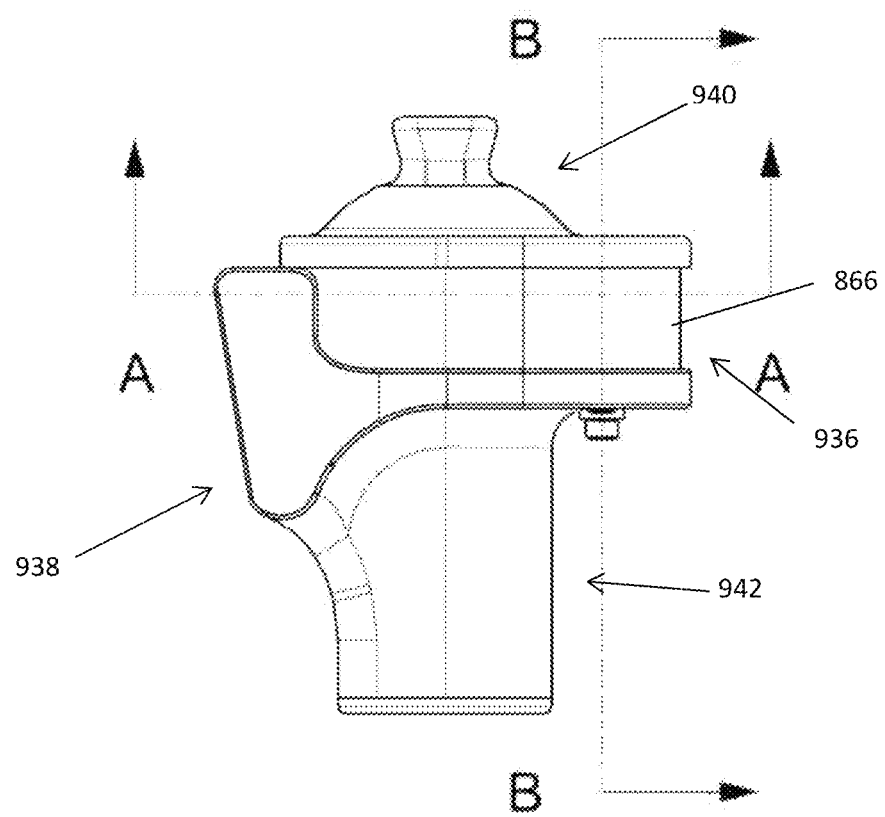
FIG. 35 is a side view of the mounting bracket of FIG. 33.
Figure 36:
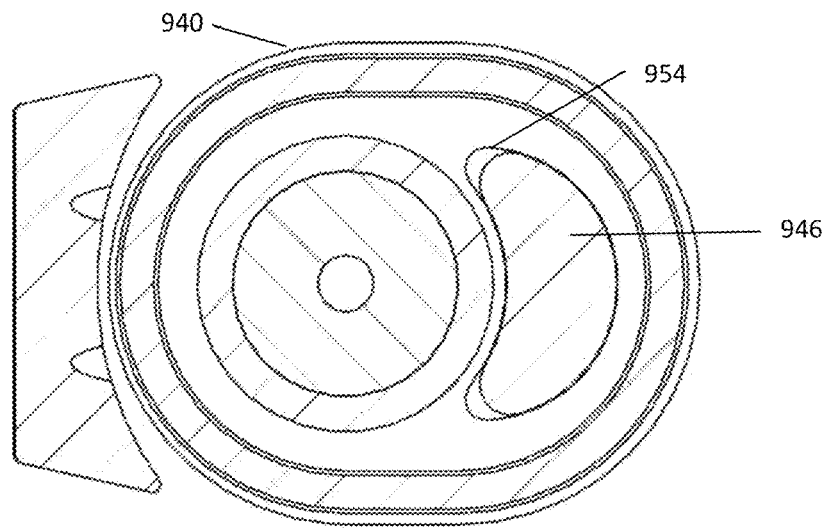
FIG. 36 is a top, cross-section view taken along the line A-A in FIG. 35 representatively illustrating portions of the mounting bracket in accordance with exemplary embodiments of the present technology.

Referring now to FIGS. 33-35, an additional embodiment of a compression torsion joint 936 for a mounting bracket 938 is shown. The mounting bracket may be attached to the prosthetic foot 100. Many of the components of the compression torsion joint 936 and the mounting bracket 938 are the same as the embodiment described above in FIGS. 10 and 19. The mounting bracket comprises an upper member 940 and a lower member 942, similar to those described above. The bumper 868, pins 884 and threaded holes 886 within the upper member 802 shown in the embodiment described in FIGS. 10 and 19 have been removed from the upper member 940 and compression torsion joint 936 described in FIGS. 33-35. The remainder of the configuration of the upper member 940 is similar to the upper member 802 described above.

In various embodiments, the compression torsion joint 936 may comprise the elastomeric ring 866. In various embodiments, the compression torsion joint 936 may comprise a rotation inhibitor 944. In various embodiments, the compression torsion joint 936 may comprise a compression collar 870. In one embodiment, the compression torsion joint 936 may comprise a combination of the elastomeric ring 866, rotation inhibitor 944, and the compression collar 870.

In various embodiments shown in FIGS. 33, 34, 40A and 40B, the rotation inhibitor 994 may comprise a crescent-shaped member 946 with a pair of downwardly protruding stops 948, 950 and a central stop 952. The crescent-shaped member 946 is received within a crescent-shaped recess 954 in the upper member 940, similar to the crescent-shaped recess 824 described above with respect to the upper member 802.

Figure 37:
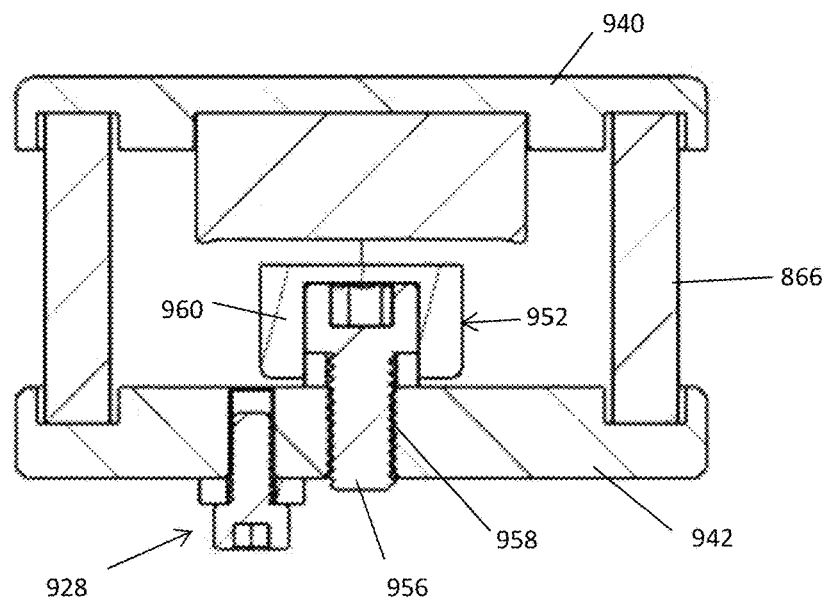
FIG. 37 is a partial, side, cross-section view taken along the line B-B in FIG. 35 representatively illustrating portions of the mounting bracket in accordance with exemplary embodiments of the present technology.
Figure 38:
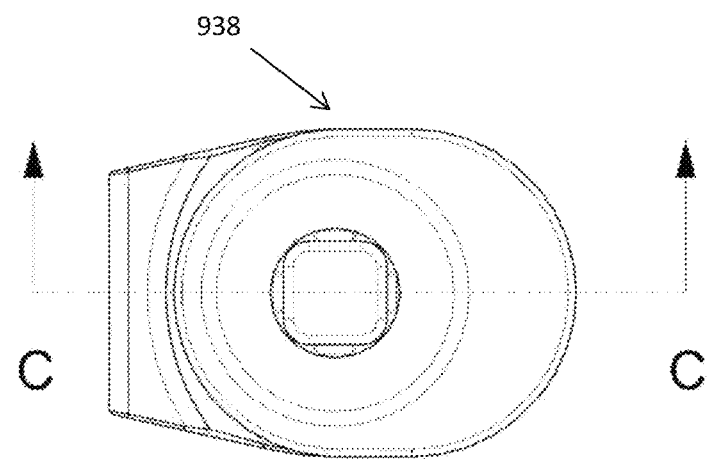
FIG. 38 is a top view of the mounting bracket of FIG. 33 in accordance with exemplary embodiments of the present technology.
Figure 39:
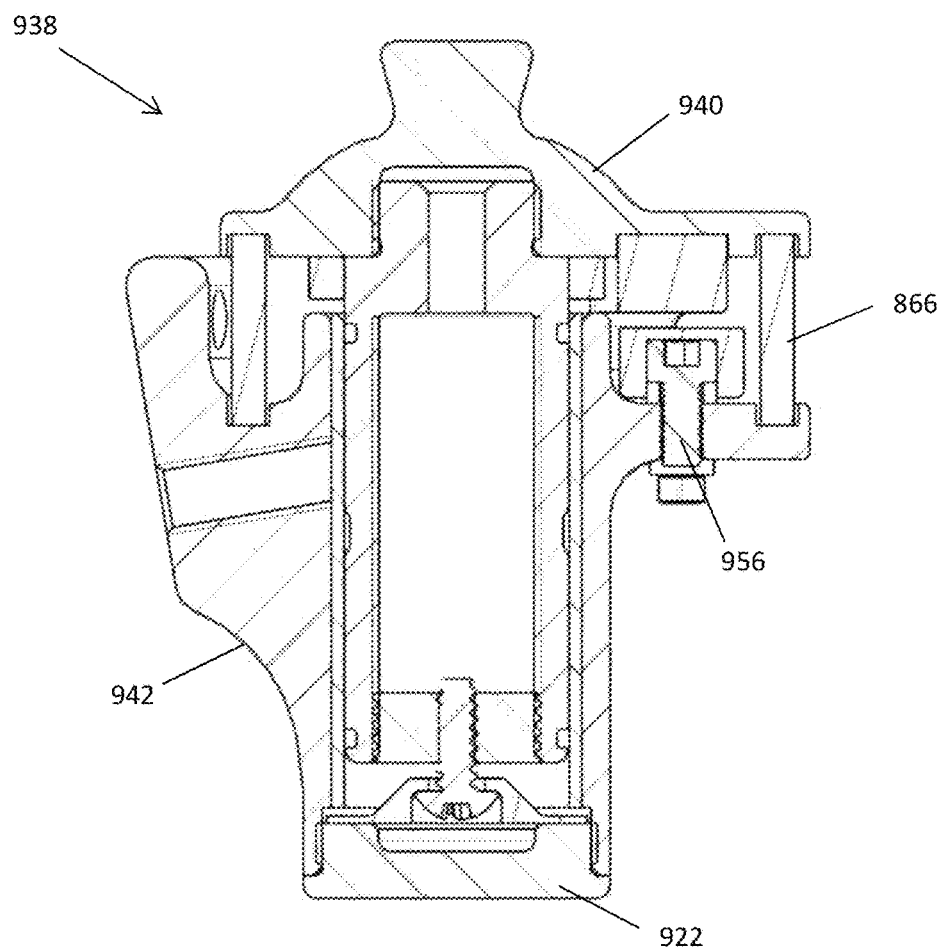
FIG. 39 is a side, cross-section view taken along the line C-C in FIG. 38 representatively illustrating portions of the mounting bracket in accordance with exemplary embodiments of the present technology.
Figure 40A:
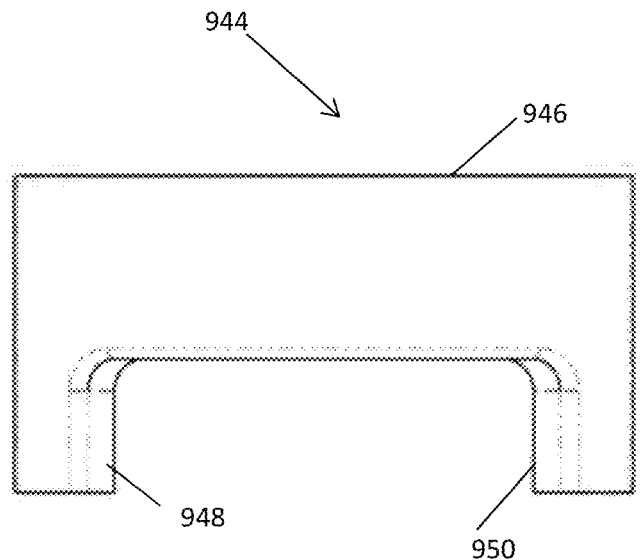
FIG. 40A is a front view of a crescent rotation inhibitor in accordance with exemplary embodiments of the present technology.
Figure 40B:
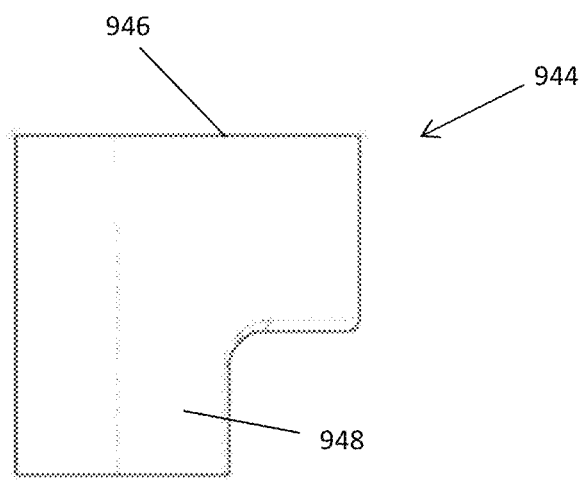
FIG. 40B is a side view of the rotation inhibitor in accordance with exemplary embodiments of the present technology.

In one embodiment, shown in FIGS. 33, 37, and 39 the central stop 952 may comprise a fastener 956 that is received within a hole 958 in the lower member 942. The fastener 956 and hole 958 configuration can both be threaded or the fastener may be threaded, received within the hole 958, and coupled to the lower member 942 via a nut (not shown). In one embodiment, a rubber bumper 960 may be coupled to the fastener 956. The hole 958 is located centrally in the lower member 942. The vent assembly 928 has been moved to the side of the centrally located hole 958. The remainder of the configuration of the lower member 942 is similar to the lower member 804 described above.

The stops 948, 950 on the crescent-shaped member 946 and the central stop 952 along with the elastomeric ring 866 are configured to limit torsional rotation of the upper member 940 with respect to the lower member 942 similar to the manner described above.

The mounting bracket 938 provides a multi-phase system. When the initial load is applied to the prosthetic foot 100, the elastomeric ring 866 provides both a soft resistance for vertical compression and torsional rotation. Once a larger load is applied, the lower surface of the compression collar 870 will contact an upper surface of the upper collar 848, thereby only allowing a limited amount of vertical movement of the upper member 940 with respect to the lower member 942. The elastomeric ring 866 and compression collar 870 limit the vertical movement while the elastomeric ring 866 provides vertical shock absorption during the gate cycle and while standing.

When a greater torsional load is applied, the elastomeric ring 866 gives increasingly stiff torsional stability until the stops 948, 950 on the crescent-shaped member 946 contact the central stop 952 to limit the amount of torsional rotation. In one embodiment, stops 948, 950 on the crescent-shaped member 946 contact the central stop 952 serve to restrict the torsional rotation approximately 5-10 degrees. In one embodiment, stops 948, 950 on the crescent-shaped member 946 contact the central stop 952 serve to restrict the torsional rotation approximately plus or minus 8 degrees.

In various embodiments the crescent shaped member may comprise materials similar to those discussed above with respect to the upper and lower members 802, 804 on the mounting bracket 800.

Referring now to FIGS. 41-44, in various embodiments, an additional embodiment of a mounting bracket 1000 is shown. Like the previous mounting brackets discussed above, the mounting bracket 1000 may be attached to the top member 120 of the prosthetic foot 100 and configured for attachment to a user. In various embodiments, the mounting bracket 1000 may comprise an upper member 1002, a lower member 1004, and a compression torsion joint 1006. The upper member 1002 may be configured for attachment to a user's residual limb. The lower member 1004 may be configured to attach to a prosthetic foot 100. In one embodiment the lower member 1004 is coupled to the prosthetic foot 100.

Figure 45A:
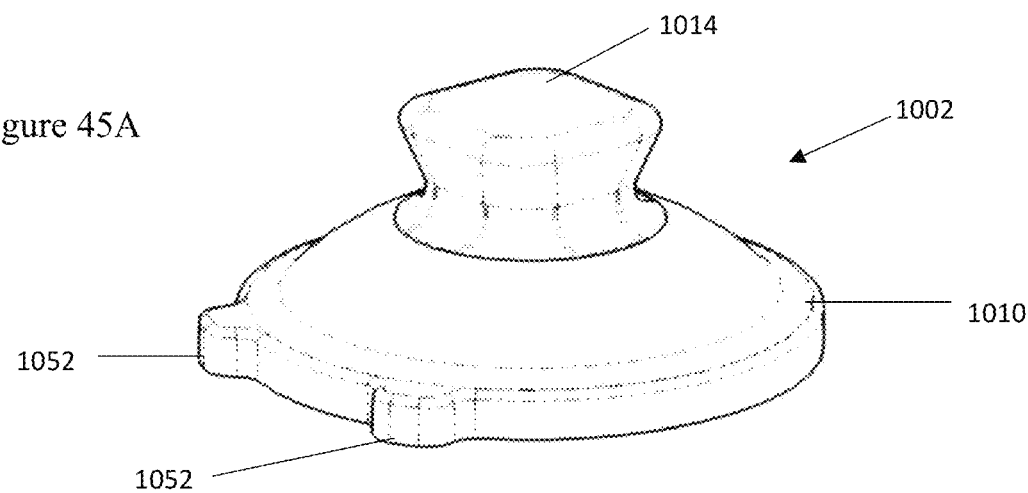
FIG. 45A is a perspective view of an additional embodiment of an upper member of the mounting bracket of FIG. 41, in accordance with exemplary embodiments of the present technology.
Figure 45B:
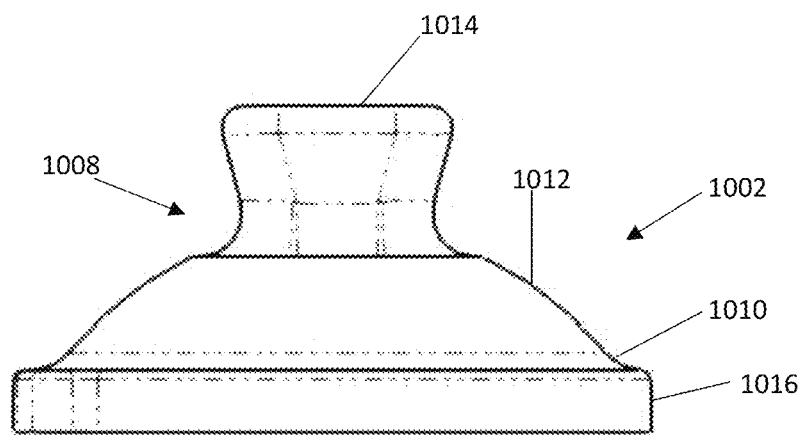
FIG. 45B is a side view of the additional embodiment of the upper member of the mounting bracket of FIG. 45A, in accordance with exemplary embodiments of the present technology.
Figure 45C:
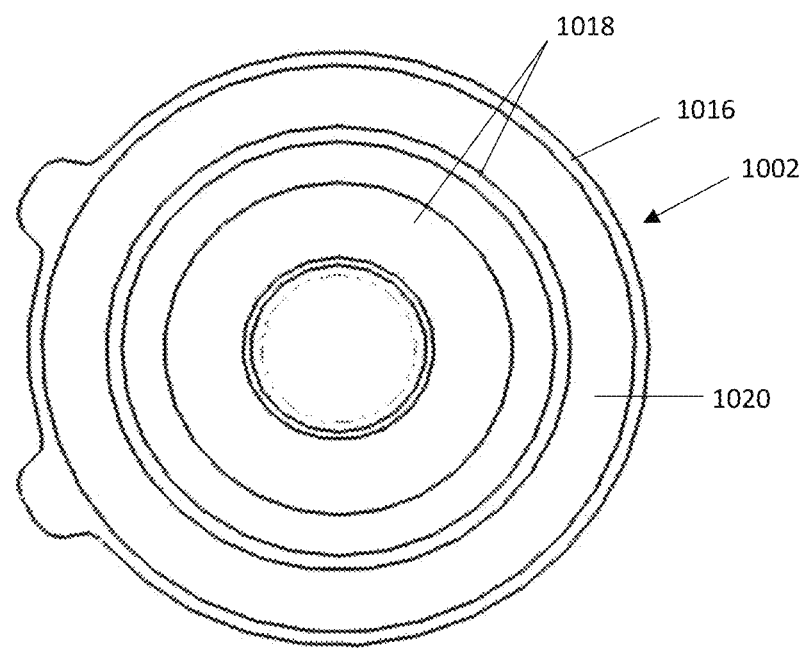
FIG. 45C is a bottom view of the additional embodiment of the upper member of the mounting bracket of FIG. 45A, in accordance with exemplary embodiments of the present technology.

Referring now to FIGS. 45A-C, the upper member 1002 may comprise mounting portion 1008 and an upper flange 1010. The mounting portion 1008 may be configured to attach to a user's residual limb. The mounting portion 1008 may comprise a spherical dome 1012 and an attachment portion 1014, which is a standard male pyramid adapter used in the prosthetic industry. The pyramid adapter may be coupled with a standard receiver used in the practice of prosthetics, for example, a Staats style attachment, which is commonly known in the prosthetic industry. The attachment portion 1014 may use a standard receiver adapter, as understood by one of ordinary skill in the art. According to various embodiments the attachment portion 1014 may facilitate attachment to the residual limb of the user. The attachment portion 1014 may comprise a centerline that is aligned with the weight line of the user.

The spherical dome 1012 may be located on the upper flange 1010. In various embodiments, the upper flange 1010 may comprise a downwardly depending lip 1016 around its perimeter and a lower surface 1018 with a channel 1020 contained therein.

Figure 27A:
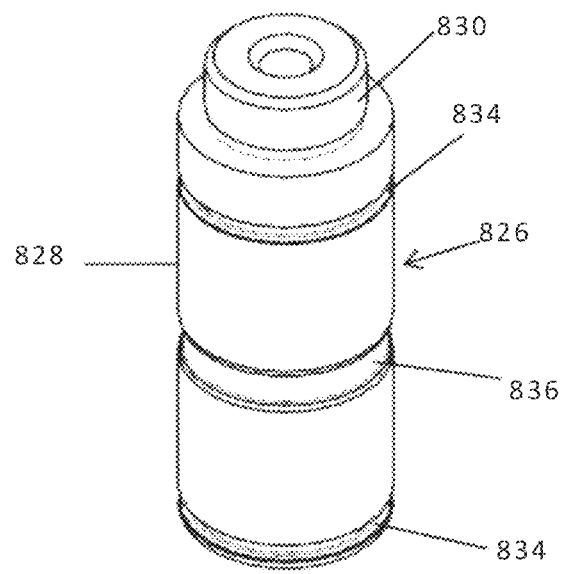
FIG. 27A is a perspective view representatively illustrating a mating post of the mounting bracket in accordance with exemplary embodiments of the present technology.
Figure 27B:
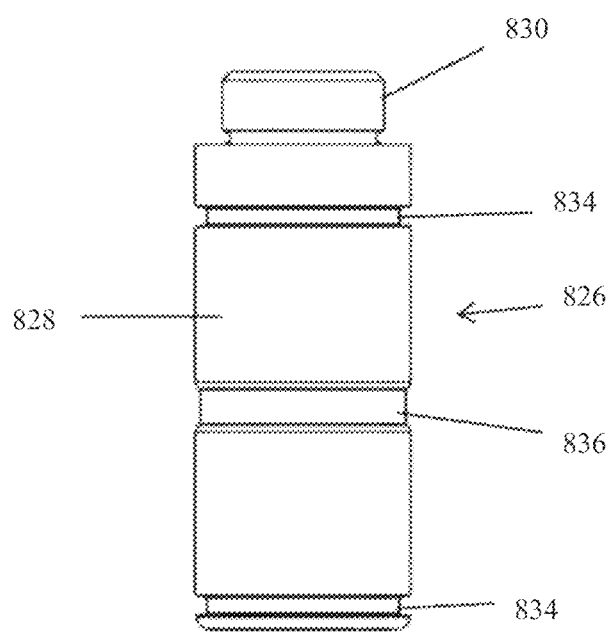
FIG. 27B is a side view representatively illustrating the mating post of the mounting bracket in accordance with exemplary embodiments of the present technology.
Figure 44:
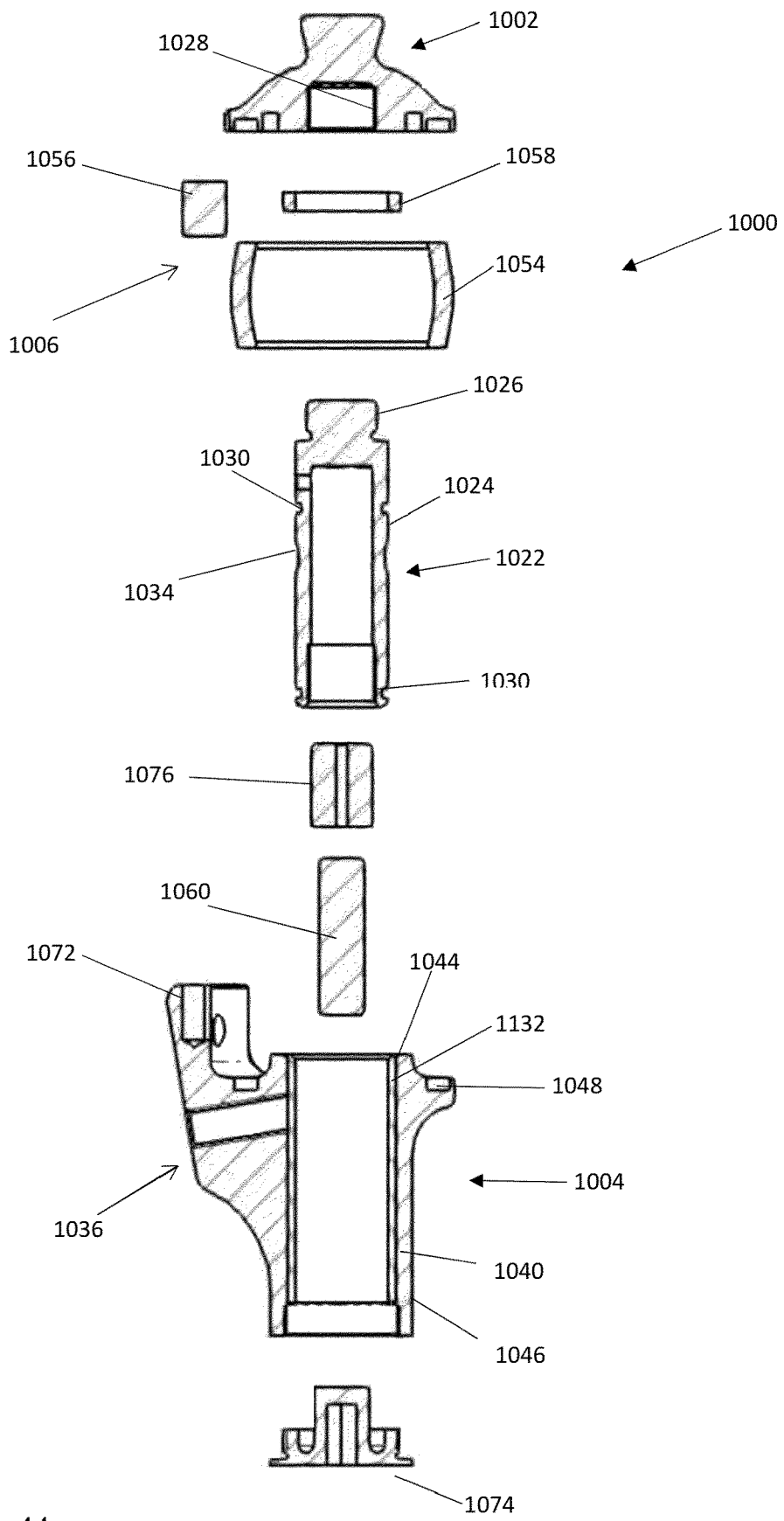
FIG. 44 is a side, exploded, cross-section view taken along the line A-A in FIG. 42 representatively illustrating portions of the mounting bracket in accordance with exemplary embodiments of the present technology.
Figures 52A, 52B:
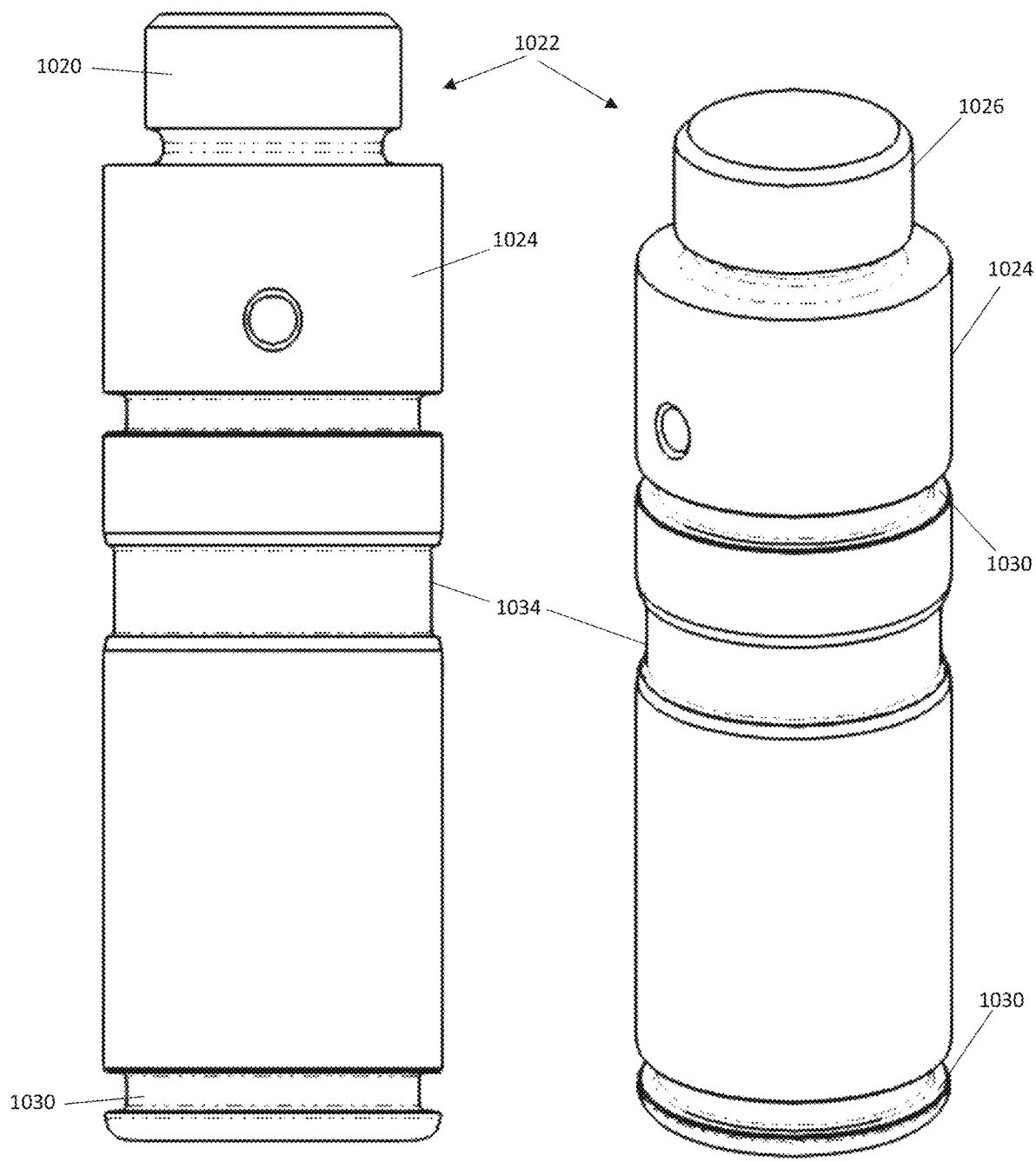
FIG. 52A is a side view representatively illustrating an additional embodiment of a mating post of the mounting bracket in accordance with exemplary embodiments of the present technology.
FIG. 52B is a perspective view representatively illustrating the mating post of the mounting bracket in accordance with exemplary embodiments of the present technology.

In various embodiments, as shown in FIGS. 44, 52A and 52B, the mounting bracket 1000 may also comprise a mating post 1022, similar to mating post 826 shown in FIGS. 27A and 27B above. The mating post 1022 may comprise a cylindrical collar 1024 depending downwardly from the lower surface 1018 of the upper flange 1010 once the mating post 1022 is coupled with the upper member 1002. In various embodiments the mating post 1022 may be a separate component that is removable or may be an integral piece. An upper portion 1026 of the mating post 1022 may be coupled to the upper member 1002 within a recess 1028 by any known method, such as screw fit, pressed, and the like. In one embodiment the mating post 1022 may be coupled to the upper member 1002 by a threaded connection. The mating post 1022 may comprise threads (not shown) on the upper portion 1026 of the cylindrical collar 1024 that are received by threads (not shown) within the recess 1028 in the upper member 1002. The mating post 1022 may further comprise at least one recess 1030 on the perimeter of the cylindrical collar 1024 that may receive O-rings (not shown). The O-rings serve to fill the clearance between the outer diameter of mating post 1022 and the inner diameter of a sleeve 1132 to provide smooth, and silent action between relatively moving components. In one embodiment, the mating post 1022 comprises at least one recess 1034 on the perimeter of the cylindrical collar 1024 that may receive grease or another lubricant during assembly.

Figures 53A, 53B:
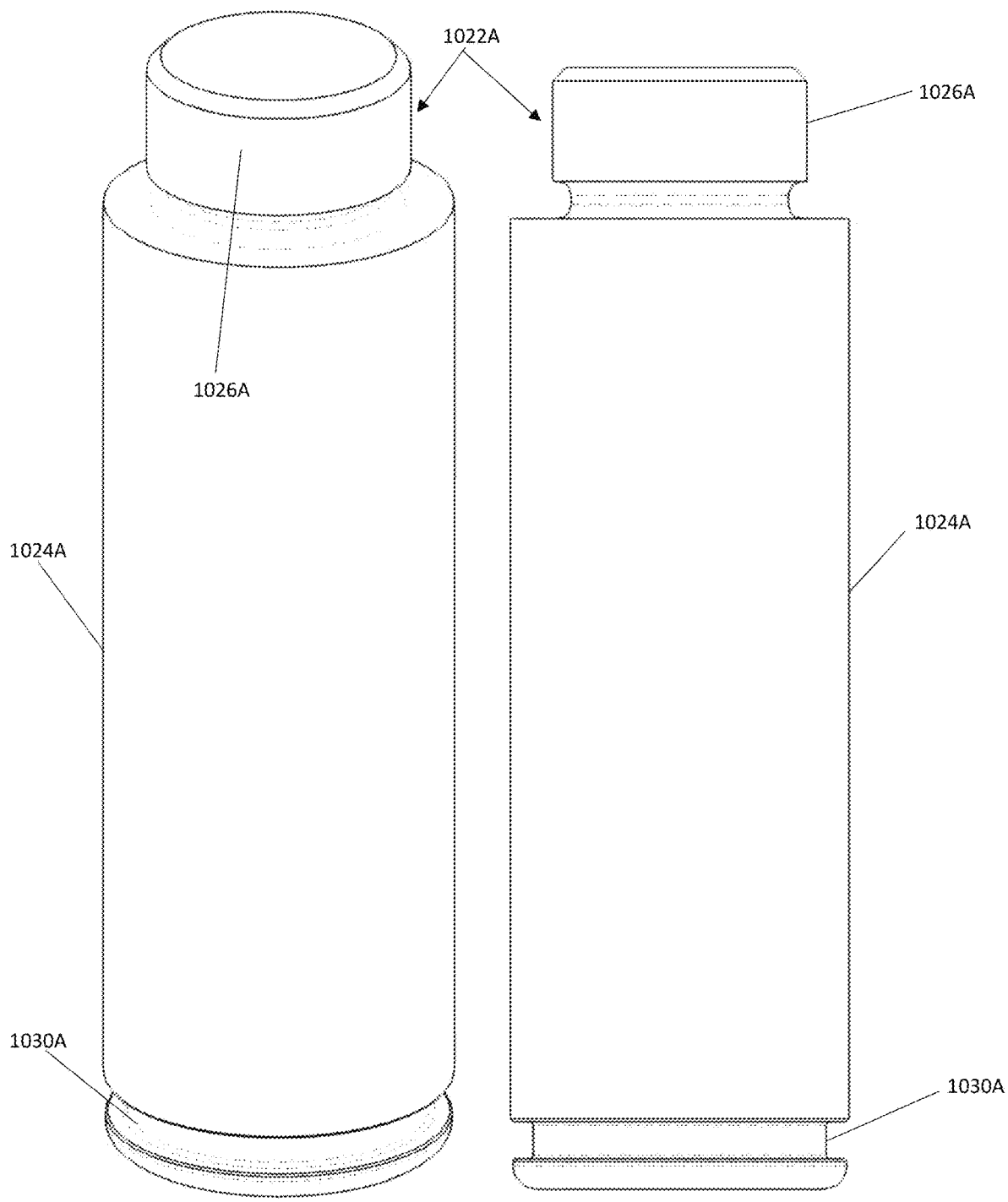
FIG. 53A is a perspective view representatively illustrating an additional embodiment of a mating post of the mounting bracket in accordance with exemplary embodiments of the present technology.
FIG. 53B is a side view representatively illustrating the mating post of the mounting bracket in accordance with exemplary embodiments of the present technology.
Figure 54A:
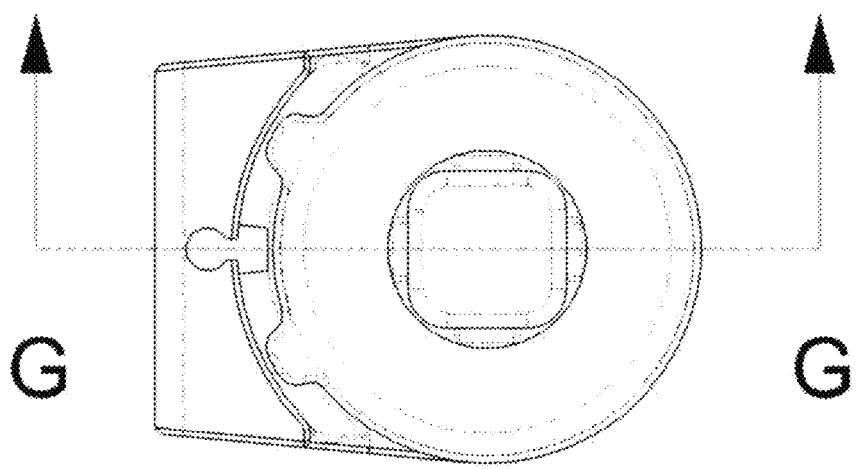
FIG. 54A is a top view representatively illustrating an additional embodiment of a mounting bracket, in accordance with exemplary embodiments of the present technology.
Figure 54B:
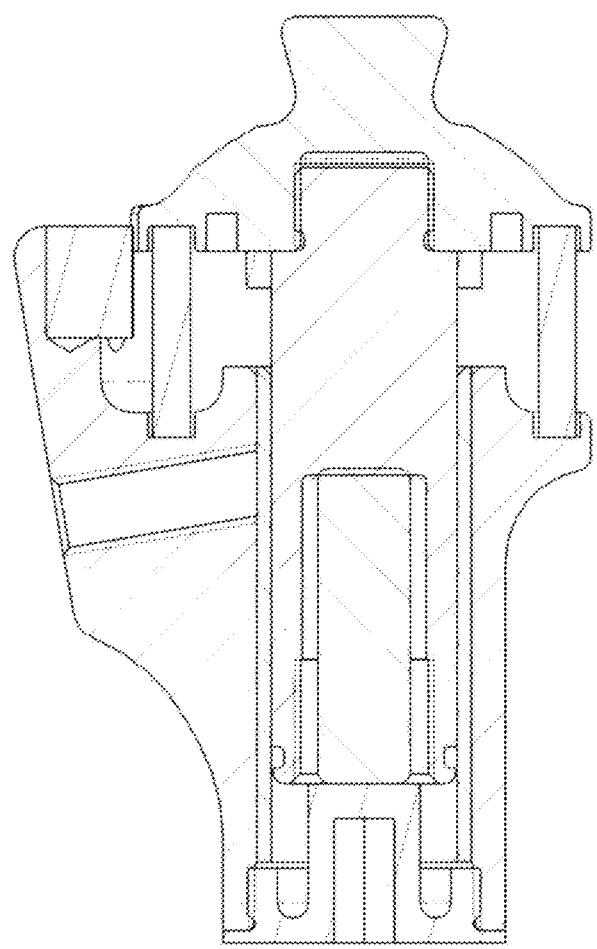
FIG. 54B is a side, cross-section view taken along the line G-G in FIG. 54A representatively illustrating portions of the mounting bracket in accordance with exemplary embodiments of the present technology.

FIGS. 53A and 53B show an alternate version of a mating post 1022A. Mating post 1022A contains many of the same features similar to mating past 1022. Specifically, mating post 1022A may comprise an upper portion 1026A, a cylindrical collar 1024A, and at least one recess 1030A on the perimeter of the cylindrical collar 1024A that may receive O-rings.

Referring now to FIGS. 43, 44, 46A and 46B, in various embodiments, the lower member 1004 may comprise a mounting portion 1036, a lower flange 1038, and a mating portion 1040. The mounting portion 1036 may be located at a rear edge of the lower flange 1038. The mounting portion 1036 may comprise at least one threaded aperture 1042 used to couple the mounting bracket 1000 to the prosthetic foot 100. In one embodiment, the mounting portion 1036 comprises 3 threaded apertures 1042 which receive fasteners to couple the mounting bracket 1000 to the prosthetic foot 100.

In various embodiments, as shown in FIG. 9, an upper end 862 of the prosthetic foot 100 may be connected to the mounting portion 1036 of the lower member 1004 via mechanical connection whereby fasteners 864 are received within apertures (not shown) residing in the upper end 862 of the prosthetic foot 100 and the mounting portion 1036 of lower member 1004. While the 1000 mounting bracket is not shown in FIG. 9, the mounting bracket 1000 may be coupled in the same manner as mounting bracket 800. While a bolted connection is shown any mechanical connection may be contemplated, such as screws, rivets, and the like. The bolted connection materials may comprise Titanium or any other suitable material. Other types of material may comprise mild steel, alloy steel, high strength stainless steel such as 13-8, and alloy aluminum such as the 2000 and 7000 series.

Figure 43:
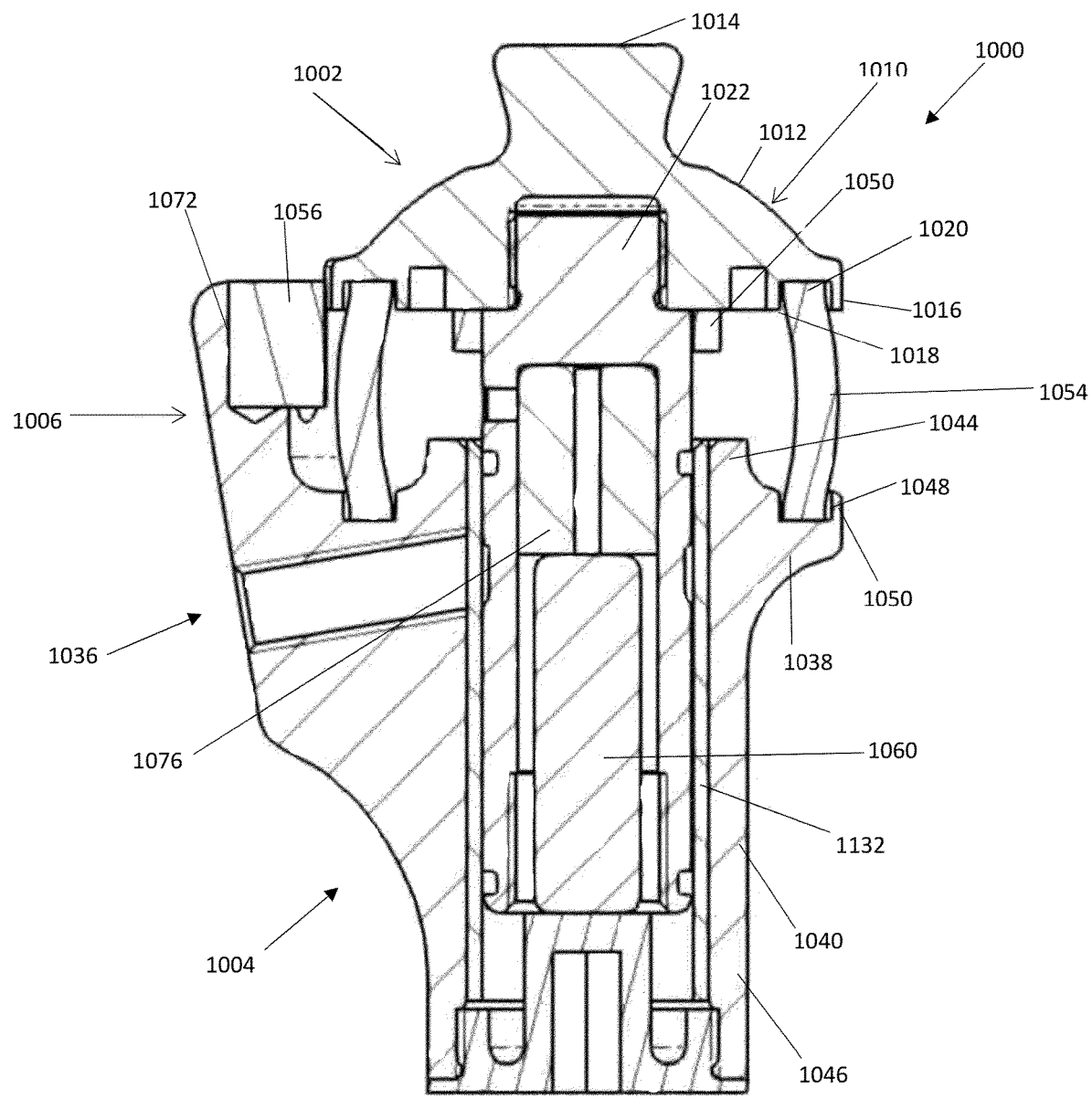
FIG. 43 is a side, cross-section view taken along the line A-A in FIG. 42 representatively illustrating portions of the mounting bracket in accordance with exemplary embodiments of the present technology.
Figure 46A:
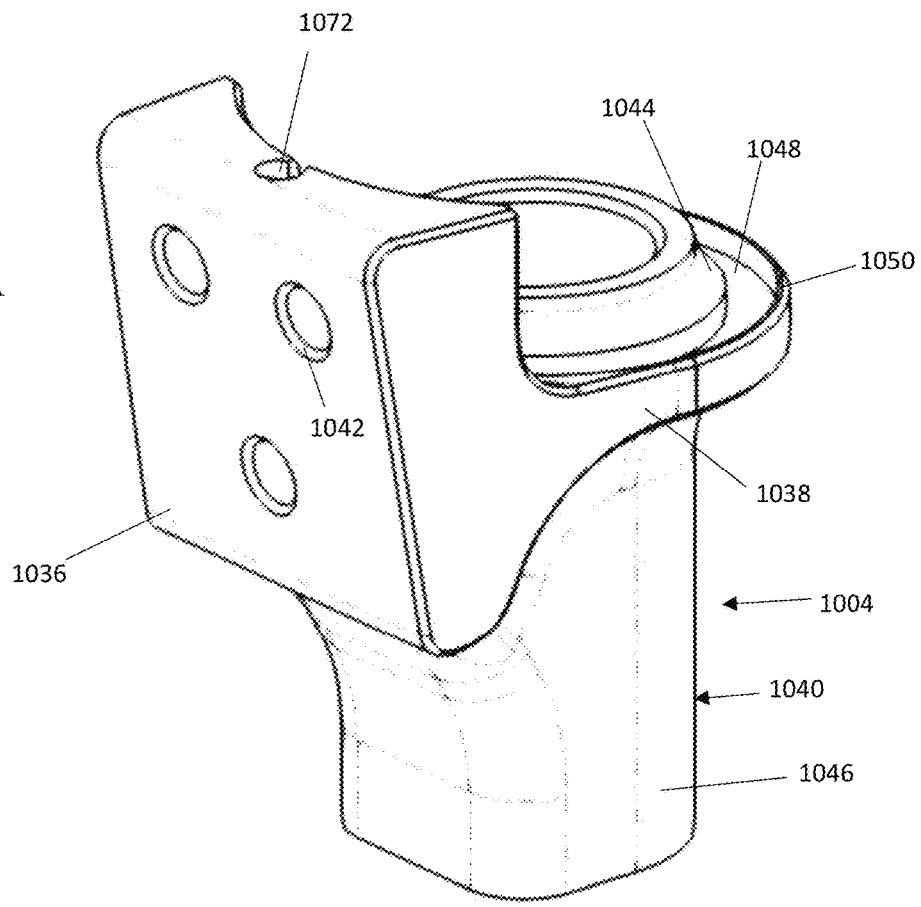
FIG. 46A is a perspective view of an additional embodiment of a lower member of the mounting bracket of FIG. 41, in accordance with exemplary embodiments of the present technology.
Figure 46B:
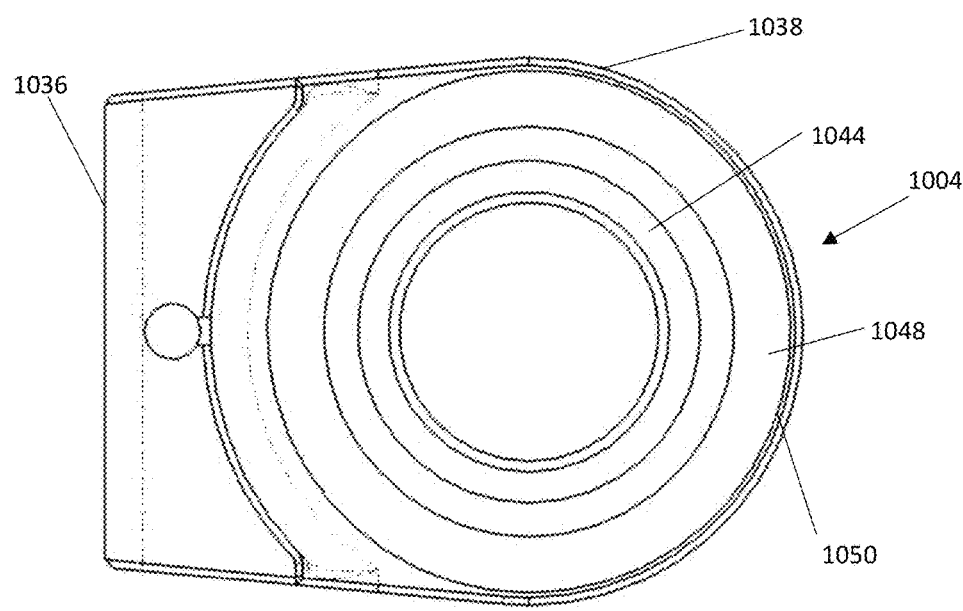
FIG. 46B is a top view of the additional embodiment of the upper member of the mounting bracket of FIG. 45A, in accordance with exemplary embodiments of the present technology.

The mating portion 1040 of the lower member 1004 may comprise an upper collar 1044 and a lower collar 1046. The upper collar 1044 depends upwardly from the lower flange 1038 while the lower collar 1046 depends downwardly from the lower flange 1038. As shown in FIGS. 43 and 44, the upper and lower collars 1044, 1046 of the mating portion 1040 combine to receive the cylindrical collar 1024 of the mating post 1022 when the upper and lower members 1002, 1004 are connected. As shown in FIGS. 46A and 46B, the lower flange 1038 may comprise a recessed channel 1048 and a lip 1050 surrounding at least a portion of the perimeter.

In various embodiments, referring now to FIGS. 45A-45C, the upper member 1002 may comprise a pair of stops 1052. The stops 1052 serve to limit rotation of the upper member 1002 with respect to the lower member 1004 during use as will be discussed in detail below. The stops 1052 reside on the upper member 1002 adjacent a perimeter of the upper flange 1010 and project outwardly therefrom. The stops 1052 are located on an exterior surface of the upper flange 1010. The location of the stops 1052 determine how much torsion needs to occur before the compression torsion joint 1006 is used. In various embodiments, the stops 1052 may be activated when the upper member 1002 of the mounting bracket 1000 rotates enough to overcome the torsional stiffness of the elastomeric ring 1054 and allow the stops 1052 to contact the torsion limiter 1056. The system of rotation stops 1052 and rotation limiter 1056 engage with each other at the same angle of rotation regardless of the amount of vertical compression experienced by the mounting bracket 1000.

Referring now to FIGS. 43 and 44 in various embodiments, the compression torsion joint 1006 may comprise an elastomeric ring 1054. In various embodiments, the compression torsion joint 1006 may comprise a torsion limiter 1056. In various embodiments, the compression torsion joint 1006 may comprise a compression collar 1058. In one embodiment, the compression torsion joint 1006 may comprise a vertical spring 1060. In one embodiment, the compression torsion joint 1006 may comprise a combination of the elastomeric ring 1054, the torsion limiter 1056, the compression collar 1058, and the vertical spring 1060.

Figure 47A:
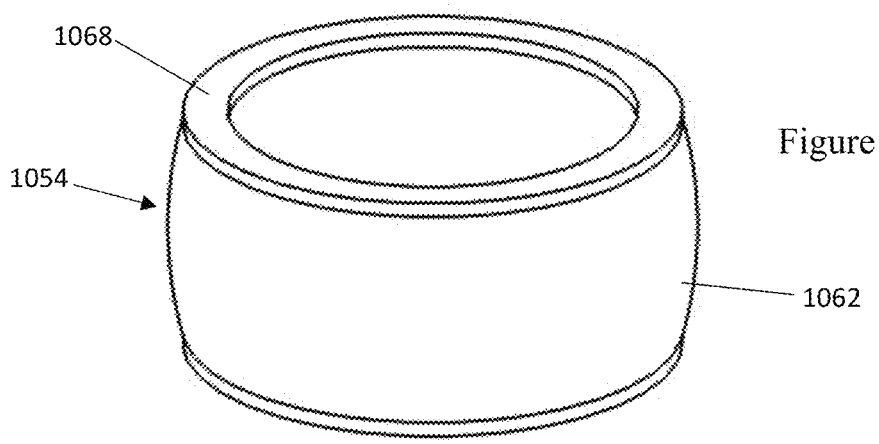
FIG. 47A is a perspective view representatively illustrating an additional embodiment of an elastomeric ring in accordance with exemplary embodiments of the present technology.
Figure 47B:
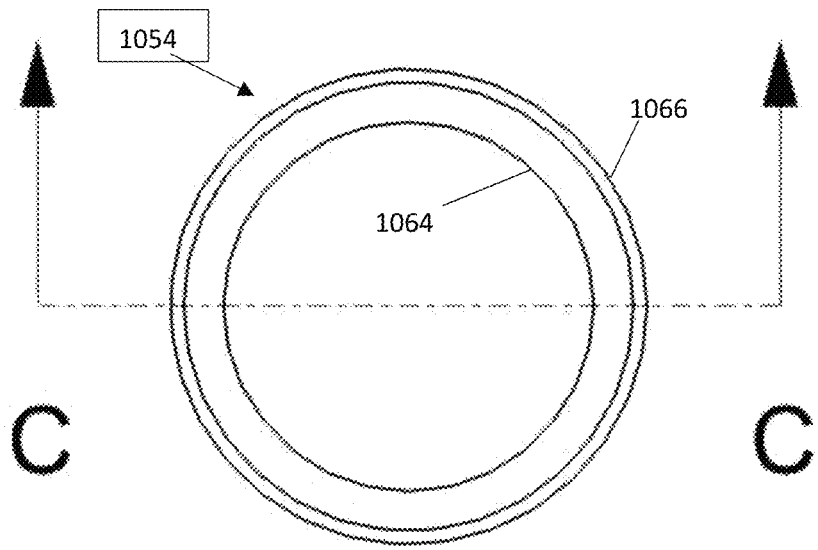
FIG. 47B is a top view representatively illustrating the additional embodiment of the elastomeric ring of the mounting bracket of FIG. 47A in accordance with exemplary embodiments of the present technology.
Figure 47C:
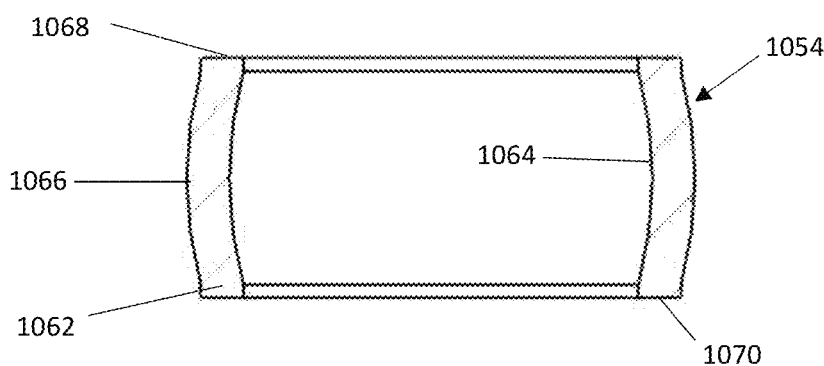
FIG. 47C is a side, cross-section view taken along the line C-C in FIG. 47A representatively illustrating the additional embodiment of the elastomeric ring of the mounting bracket of FIG. 47A in accordance with exemplary embodiments of the present technology.
Figure 48A:
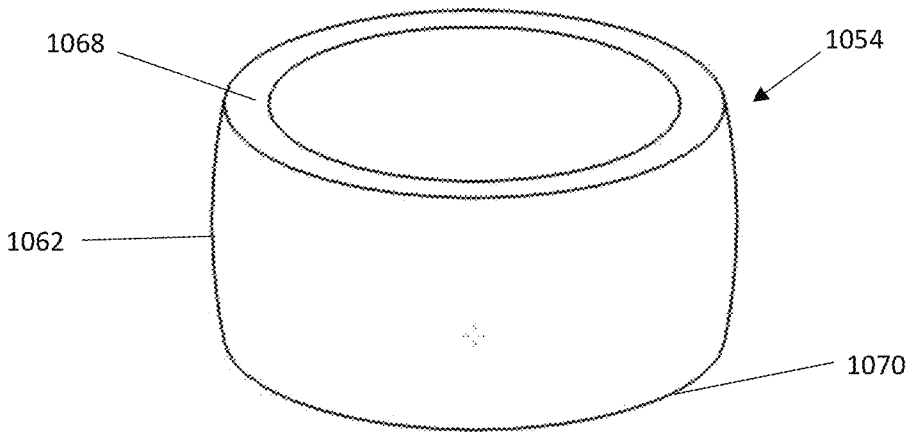
FIG. 48A is a perspective view representatively illustrating an additional embodiment of an elastomeric ring in accordance with exemplary embodiments of the present technology.
Figure 48B:
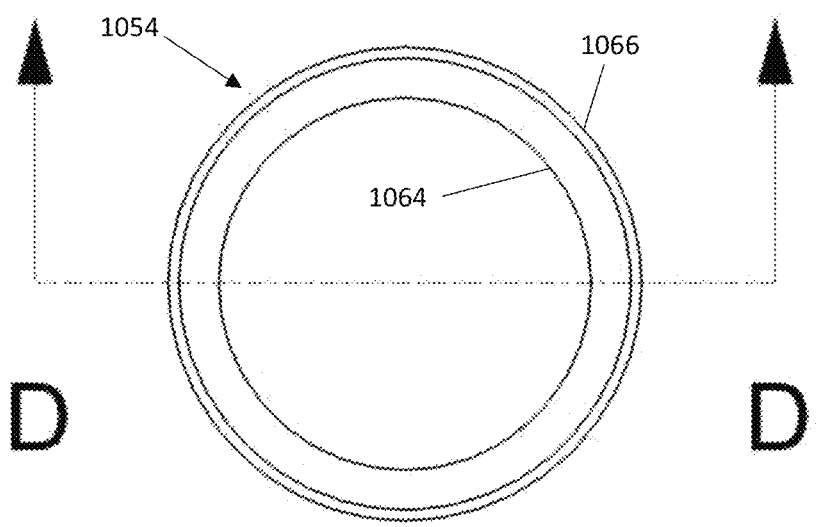
FIG. 48B is a top view representatively illustrating the additional embodiment of the elastomeric ring of the mounting bracket of FIG. 48A in accordance with exemplary embodiments of the present technology.
Figure 48C:
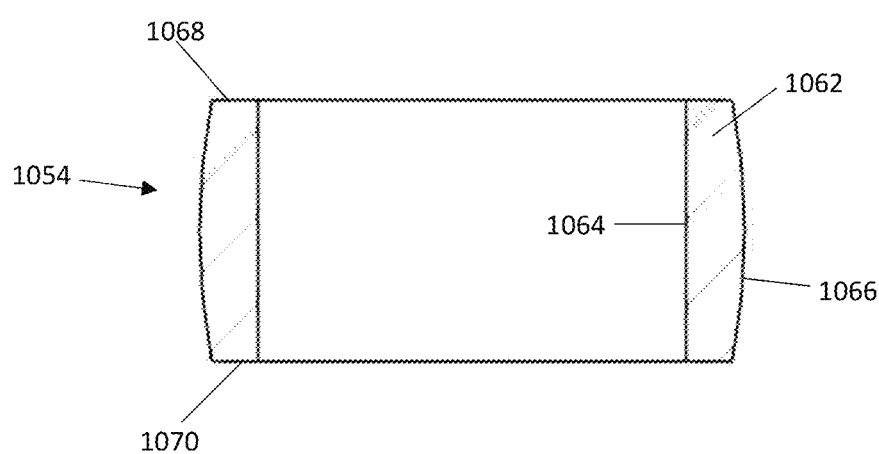
FIG. 48C is a side, cross-section view taken along the line D-D in FIG. 48A representatively illustrating the additional embodiment of the elastomeric ring of the mounting bracket of FIG. 47A in accordance with exemplary embodiments of the present technology.
Figure 49A:
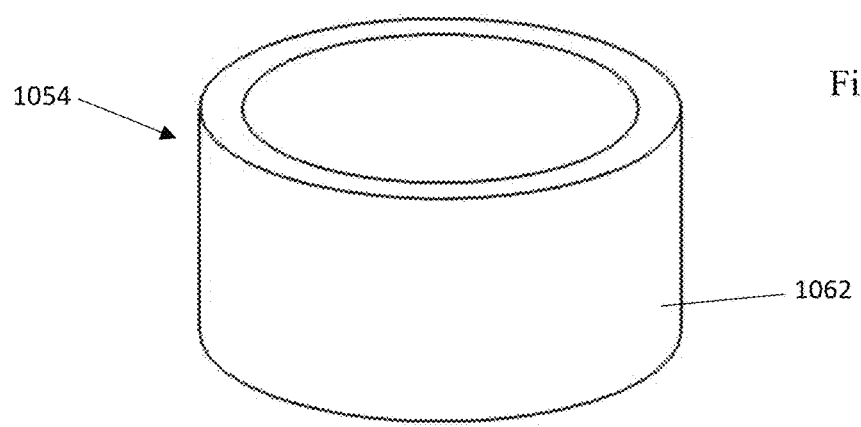
FIG. 49A is a perspective view representatively illustrating an additional embodiment of an elastomeric ring in accordance with exemplary embodiments of the present technology.
Figure 49B:
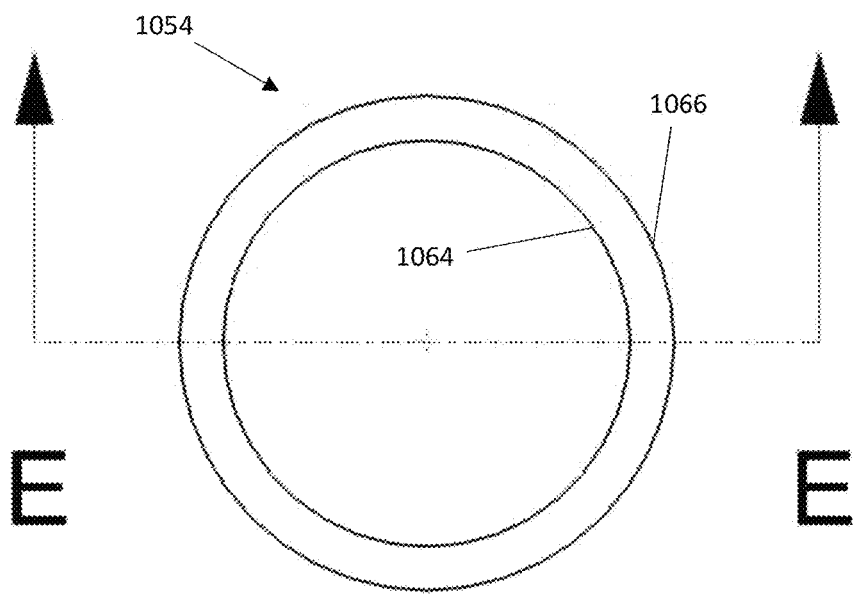
FIG. 49B is a top view representatively illustrating the additional embodiment of the elastomeric ring of the mounting bracket of FIG. 48A in accordance with exemplary embodiments of the present technology.
Figure 49C:
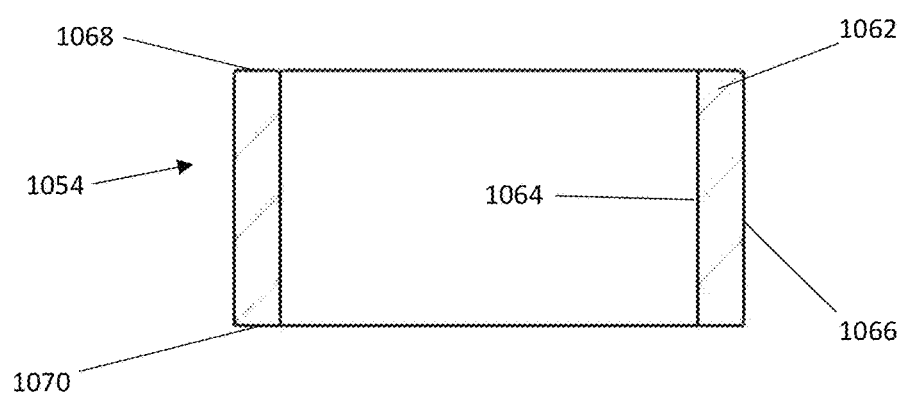
FIG. 49C is a side, cross-section view taken along the line D-D in FIG. 48A representatively illustrating the additional embodiment of the elastomeric ring of the mounting bracket of FIG. 47A in accordance with exemplary embodiments of FIG. 50A is a perspective view representatively illustrating a compression cap for a mounting bracket in accordance with exemplary embodiments of the present technology.

In various embodiments, the elastomeric rings shown in FIGS. 47-49 are similar to the elastomeric ring discussed above in FIGS. 19, 22A and 22B. The elastomeric rings 1054 generally may comprise a wall 1062 with inner 1064, outer 1066, upper 1068, and lower 1070 surfaces. In various embodiments, the inner surface 1064 of the wall 1062 may comprise a substantially smooth surface. In various embodiments, the inner surface 1064 may comprise a ridged surface, a surface with raised portions, and or a wall with varying thickness. In one embodiment, shown in FIGS. 47A-47C, the inner and outer surfaces 1064, 1066 may be curved from the upper 1068 to lower surface 1070, and/or concave with respect to the center of the elastomeric ring 1054. In one embodiment, the outer surface 1066 may be curved, and/or convex with respect to the center of the elastomeric ring 1054. In one embodiment, shown in FIGS. 48A-48C, the inner surfaces 1064 may be generally straight and the and outer surfaces 1066 may be curved from the upper 1068 to lower surface 1070, and/or concave with respect to the center of the elastomeric ring 1054. In one embodiment, shown in FIGS. 49A-49C, the inner and outer surfaces 1064, 1066 may be generally straight from the upper 1068 to lower surface 1070.

Referring now to FIGS. 43, 44, and 47-50, the upper surface 1068 of the elastomeric ring 1054 may be received in the channel 1020 in the upper flange 1010 in the upper member 1002. The outer surface 1066 generally abuts the lip 1016 of the upper flange 1010 of the upper member 1002. The lower surface 1070 of the elastomeric ring 1054 may be received in the channel 1048 in the lower flange 1038 in the lower member 1004. The outer surface 1066 generally abuts the lip 1050 of the lower flange 1038 of the lower member 1004.

Figure 41:
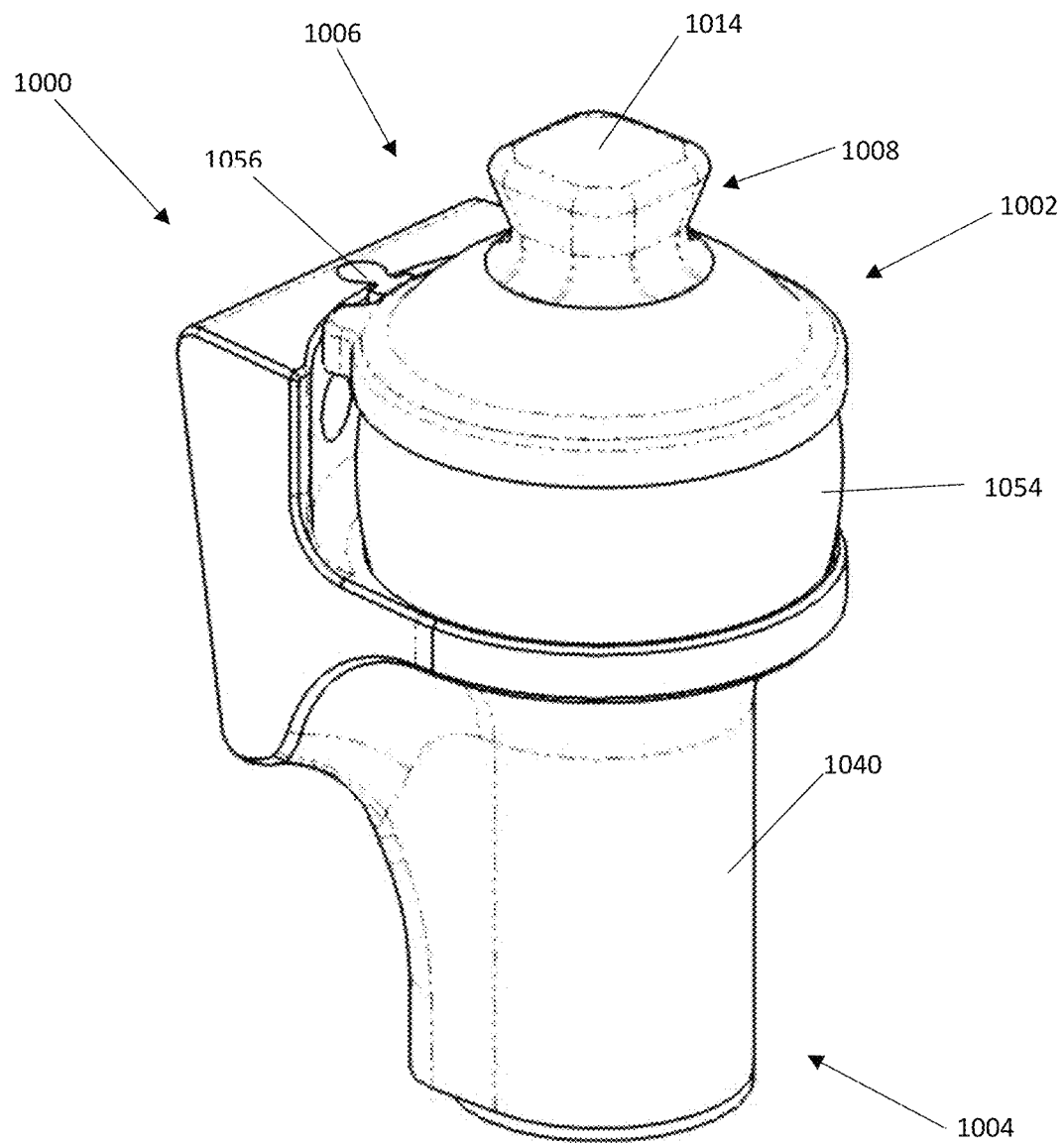
FIG. 41 is a perspective view representatively illustrating an additional embodiment of a mounting bracket in accordance with exemplary embodiments of the present technology.
Figure 42:
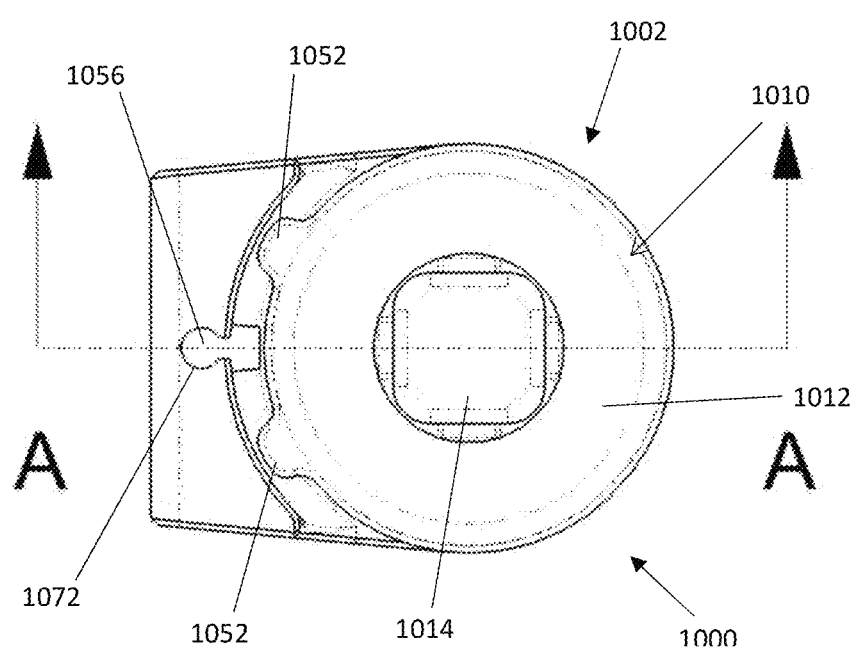
FIG. 42 is a top view representatively illustrating the additional embodiment of the mounting bracket of FIG. 41, in accordance with exemplary embodiments of the present technology.

In one embodiment, shown in FIGS. 41-43, the torsion limiter 1056 may be received in an aperture 1072 located within an upper portion of the mounting portion 1036 of the lower member 1004. In use, the torsion limiter 1056 is configured to contact the stops 1052 on the upper member 1002 to limit the torsional rotation of the upper member 1002 with respect to the lower member 1004 during use. The torsion limiter 1056 may comprise an elastomeric material including but not limited to natural rubber, synthetic rubber, a combination of natural rubber and synthetic rubber, polyurethane, and the like.

In various embodiments, as shown in FIGS. 43 and 44 the compression collar 1058 may be received on the mating post 1022 and abut the lower surface 1018 of the upper flange 1010. In one embodiment, when assembled, a gap may exist between the lower surface of the compression collar 1058 and an upper surface of the upper collar 1044. A gap may also exist between a lower surface of torsion limiter 1056 and the upper surface of the lower flange 1038. In another embodiment, when assembled, the lower surface of the compression collar 1058 may abut an upper surface of the upper collar 1044.

In various embodiments, the vertical spring 1060 may be received within the cylindrical collar 1024 of the mating post 1022. The vertical spring 1060 may comprise material an elastomeric material including but not limited to natural rubber, synthetic rubber, a combination of natural rubber and synthetic rubber, polyurethane, and the like. The vertical spring 1060 limits the amount of vertical movement of the upper member 1002 with respect to the lower member 1004.

In various embodiments, the vertical spring 1060 may reside between a lower surface of the cylindrical collar 1024 and a compression cap 1074. In one embodiment, the vertical spring 1060 may reside between a plug 1076 located within the cylindrical collar 1024 adjacent the lower surface and the compression cap 1074. The vertical spring 1060 limits the amount of vertical movement of the upper member 1002 with respect to the lower member 1004 by contacting the lower surface of the cylindrical collar 1024 within the mating post 1022 and the compression cap 1074.

Figure 50A:
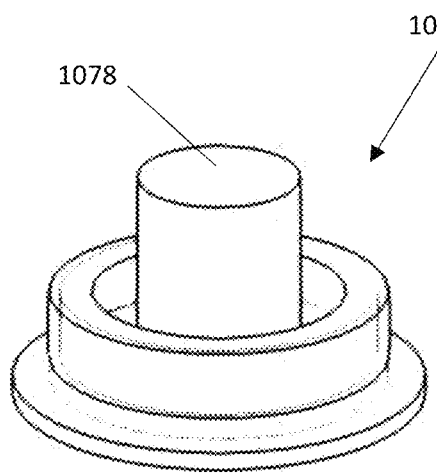
FIG. 50B is a top view representatively illustrating the compression cap of FIG. 50A for a mounting bracket, in accordance with exemplary embodiments of the present technology.
FIG. 50C is a side view representatively illustrating the compression cap of FIG. 50A for a mounting bracket, in accordance with exemplary embodiments of the present technology.
FIG. 50D is a bottom view representatively illustrating the compression cap of FIG. 50A for a mounting bracket, in accordance with exemplary embodiments of the present technology.
Figure 50B:
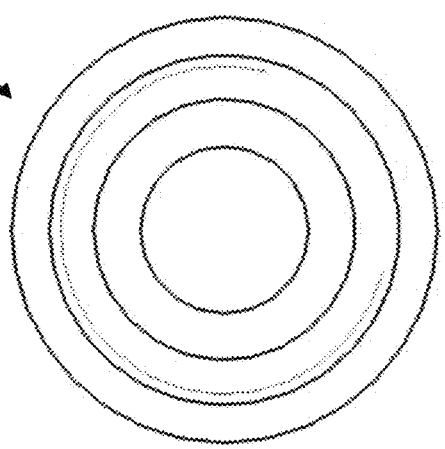
Figure 50C:
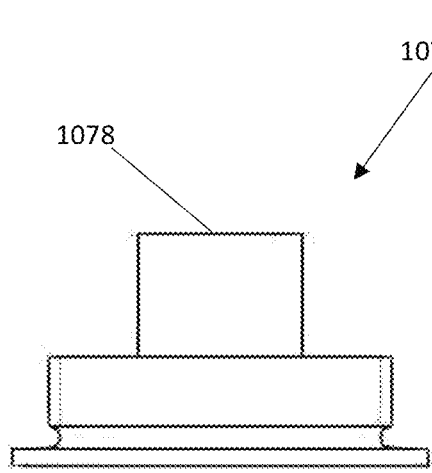
Figure 50D:
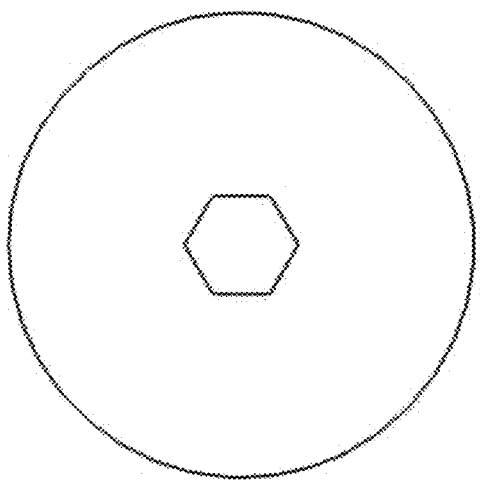
Figure 51A:
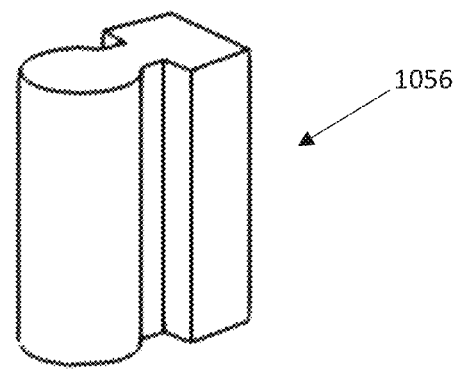
FIG. 51A is a perspective view of a torsion limiter for a mounting bracket, in accordance with exemplary embodiments of the present technology.
Figure 51B:
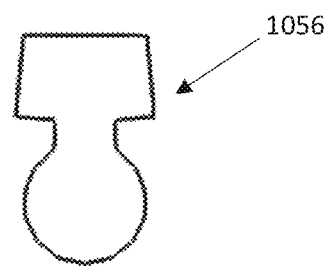
FIG. 51B is a top or bottom view of the torsion limiter of FIG. 51A for a mounting bracket, in accordance with exemplary embodiments of the present technology.

In various embodiments, referring to FIGS. 45 and 50A-B, the compression cap 1074 may comprise threads which are received within internal threads (check figures) located in an internal wall in the cylindrical collar 1024 of the mating post 1022. The compression cap 1074 may be used in conjunction with the mating post 1022, which is received within the sleeve 1132, to couple the upper member 1002 to the lower member 1004. The sleeve 1132 may comprise a low-friction material that facilitates smooth movement between the upper and lower members 1002, 1004. In various embodiments, the compression cap 1074 may comprise an elevated post 1078 that contacts a lower surface of the vertical spring 1060.

In use, the cylindrical collar 1024 of the mating post 1022 is received within the sleeve 1132, which is received in the upper and lower collars 1044, 1046 of the mating portion 1040 when the upper and lower members 1002, 1004 are connected.

The sleeve 1132 is similar to the sleeve 910 discussed above in FIG. 25. The sleeve 1132 may comprise a cylindrical wall and first and second ends. The sleeve 1132 fits within the mating portion 1040 of the lower member 1004. The sleeve 1132 may be inserted at a lower end of the lower member 1004 and may extend along the length of the mating portion 1040. The first end of the sleeve 1132 may abut a lip formed in the interior of the upper collar 1044 of the lower member 1004. The lip is configured to retain the first end within the mating portion 1040.

The sleeve 1132 may be made from any suitable low-friction material. In one embodiment the low friction sleeve is made from plastic to allow for smooth movement between the components of the prosthetic foot. In one embodiment a low coefficient plastic bushing material may be used.

In use under load, the vertical spring 1060 and the elastomeric ring 1054 in conjunction with compression collar 1058 provide a limited amount of vertical movement of the upper member 1002 with respect to the lower member 1004. The compression collar 1058, the elastomeric ring 1054, and the vertical spring 1060 limit vertical movement while the torsion limiter 1056 limits the torsional movement. The elastomeric ring 1054 provides vertical shock absorption and torsional stability during the gate cycle and while standing. The vertical spring 1060 provides vertical shock absorption and compression when in use.

The mounting bracket 1000 provides a multi-phase system. When the initial load is applied to the prosthetic foot 100, the elastomeric ring 1054 provides both a soft resistance for vertical compression and torsional rotation. Under compression, the elastomeric ring 1054 and the vertical spring 1060 simultaneously provide resistance. The elastomeric ring 1054 carries a small portion of the compressive load relative to the vertical spring 1060, which carries the majority of the compressive load. Once a larger load is applied, the vertical spring 1060 is compressed between the plug 1076 located within the cylindrical collar 1024 and the compression cap 1074 and the lower surface of the compression collar 1058 will contact an upper surface of the upper collar 1044, thereby only allowing a limited amount of vertical movement of the upper member 1002 with respect to the lower member 1004. The compression collar 1058 limits the vertical movement while the elastomeric ring 1054 and vertical spring 1060 provides vertical shock absorption during the gate cycle and while standing.

When a greater torsional load is applied, the elastomeric ring 1054 gives increasingly stiff torsional stability until the torsion limiter 1056 contacts the stops 1052 to limit the amount of torsional rotation. In one embodiment, the torsion limiter 1056 and the stops 1052 serve to restrict the torsional rotation approximately 5-10 degrees. In one embodiment, the torsion limiter 1056 and the stops 1052 serve to restrict the torsional rotation approximately plus or minus 8 degrees.

In various embodiments, the elastomeric ring 1054 may comprise a lower durometer than the torsion limiter 1056 and compression collar 1058 thereby providing an initial soft resistance to vertical load and torsional rotation. The higher durometer compression collar 1058 provides a greater resistance during high vertical loads. The compression collar 1058 can comprise different heights that affect the sensation of the mounting bracket 1000 during vertical compression. If the compression collar 1058 is taller, it can make contact before the torsion limiter 1056. The higher durometer torsion limiter 1056 provides a greater resistance during torsional high loads. Thus, the system described above may provide multi-phase resistance to vertical loading and torsional rotation based on the user's needs.

According to various embodiments the upper and lower members 1002, 1004 may be made from Titanium (any type) or any other suitable material. In one embodiment the upper member 1002 may comprise titanium. In one embodiment the lower member 1004 may comprise alloy aluminum. Some other types of material that may be used for the upper and lower members 1002, 1004 comprise mild steel, alloy steel, steel, high strength stainless steel such as 13-8, alloy aluminum such as the 2000 and 7000 series, and any suitable composite material.

In various embodiments, the upper and lower members 1002, 1004 described above can be an integral piece or multiple pieces joined together by any suitable method. In some embodiments, depending on the type of material, the upper and lower members 1002, 1004 may be fabricated by milling, casting, forging, powdered metal, and the like. In one embodiment, the upper and lower members 1002, 1004 may be fabricated on a titanium CNC milling machine. More specifically, in one embodiment the upper and lower members 1002, 1004 may be unitary made from alloy aluminum fabricated using a CNC milling machine. In other embodiments, the aluminum, titanium, magnesium or other suitable material for the upper and lower members 1002, 1004 may be fabricated using a CNC milling machine. In other embodiments, the aluminum, titanium, magnesium or other suitable for the upper and lower members 1002, 1004 may be fabricated by casting, forging, powdered metal, and the like. In other embodiments, a chrome moly, steel, or other suitable material for the upper and lower members 1002, 1004 can be made from multiple pieces and coupled together by welding or any other suitable method According to various embodiments and referring to FIGS. 41-44 the upper and lower members 1002, 1004 may be coupled by the elastomeric ring 1054. The elastomeric ring 1054 may comprise any rubber, polyurethane, and/or elastomeric materials. The elastomeric ring 1054 may be bonded to the upper and lower members 1002, 1004 using an adhesive. The upper surface 1068 of the elastomeric ring 1054 may be received in and bonded within the channel 1020 in the upper flange 1010 in the upper member 1002. The lower surface 1070 of the elastomeric ring 1054 may be received in and bonded the channel 1048 in the lower flange 1038 in the lower member 1004. The elastomeric ring 1054 may act as a shock for absorbing force on the downward strike during the user's stride.

In various embodiments, the elastomeric ring 1054 may comprise an adhesive bonding and thus coupling the lower member to the upper member. Further, the adhesive bonding of the elastomeric ring 1054 may produce distributed stresses. Though other modulus values are contemplated, and various moduli may be used as well, a stiffer adhesive is preferred compared to a flexible adhesive. The elastomeric ring 1054 creates a space between the upper flange 1010 of the upper member 1002 and the lower flange 1038 of the lower member 106. The adhesive may be commingled with the elastomeric ring 1054.

The prosthetic foot 100 can be adjusted to accommodate a user in part by adjusting characteristics of the elastomeric ring 1054 between the upper member 1002 and lower member 1004. For example, in various embodiments, the durometer of the elastomeric ring 1054 can be increased for users with more heel strike force, which may be caused by additional weight or dynamic activity.

In various embodiments and as shown the elastomeric ring 1054, the torsion limiter 1056, and the vertical spring 1060 may comprise an elastomeric material. The elastomeric material may comprise a general elastomeric material, polyurethane, natural rubber, a synthetic rubber, or various combinations of natural and synthetic rubber, plastic, metal and the like. The durometer of the elastomeric material of both the elastomeric ring 1054, the torsion limiter 1056, and the vertical spring 1060 may be varied to provide additional adjustment of the prosthetic foot. The elastomeric material of the elastomeric ring 1054, the torsion limiter 1056, and the vertical spring 1060 supports load. Further, since the elastomeric ring 1054 couples the upper and lower members 1002, 1004, the members are capable of torsional rotation during use of the prosthetic foot 100. The adjustable durometer of the elastomeric material allows the adjustment of the spring rate of the elastomeric ring based on user needs such as activity level, compliance level, weight changes, and the like. For example, in various embodiments, the durometer of the elastomeric material can be increased for users with more heel strike force, which may be caused by additional weight of the user or dynamic activity of the user. Increased heel strike force also provides greater compression of the heel member. As stated above the elastomeric ring 1054 and the vertical spring 1060 may comprise a lower durometer than the torsion limiter 1056 thereby providing an initial soft resistance to vertical load and torsional rotation. The higher durometer torsion limiter 1056 provides a greater resistance during high torsional loads.

Figure 56:
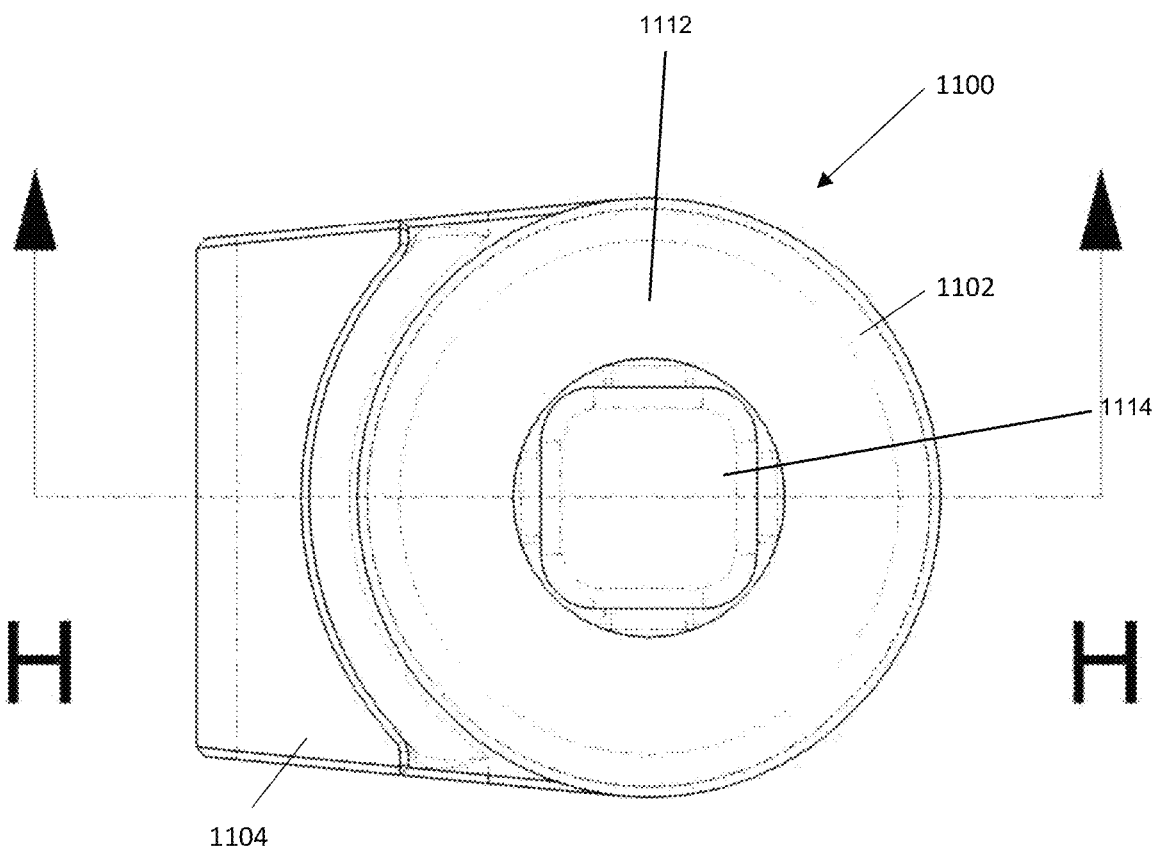
FIG. 56 is a top view representatively illustrating an additional embodiment of a mounting bracket, in accordance with exemplary embodiments of the present technology.
Figure 57:
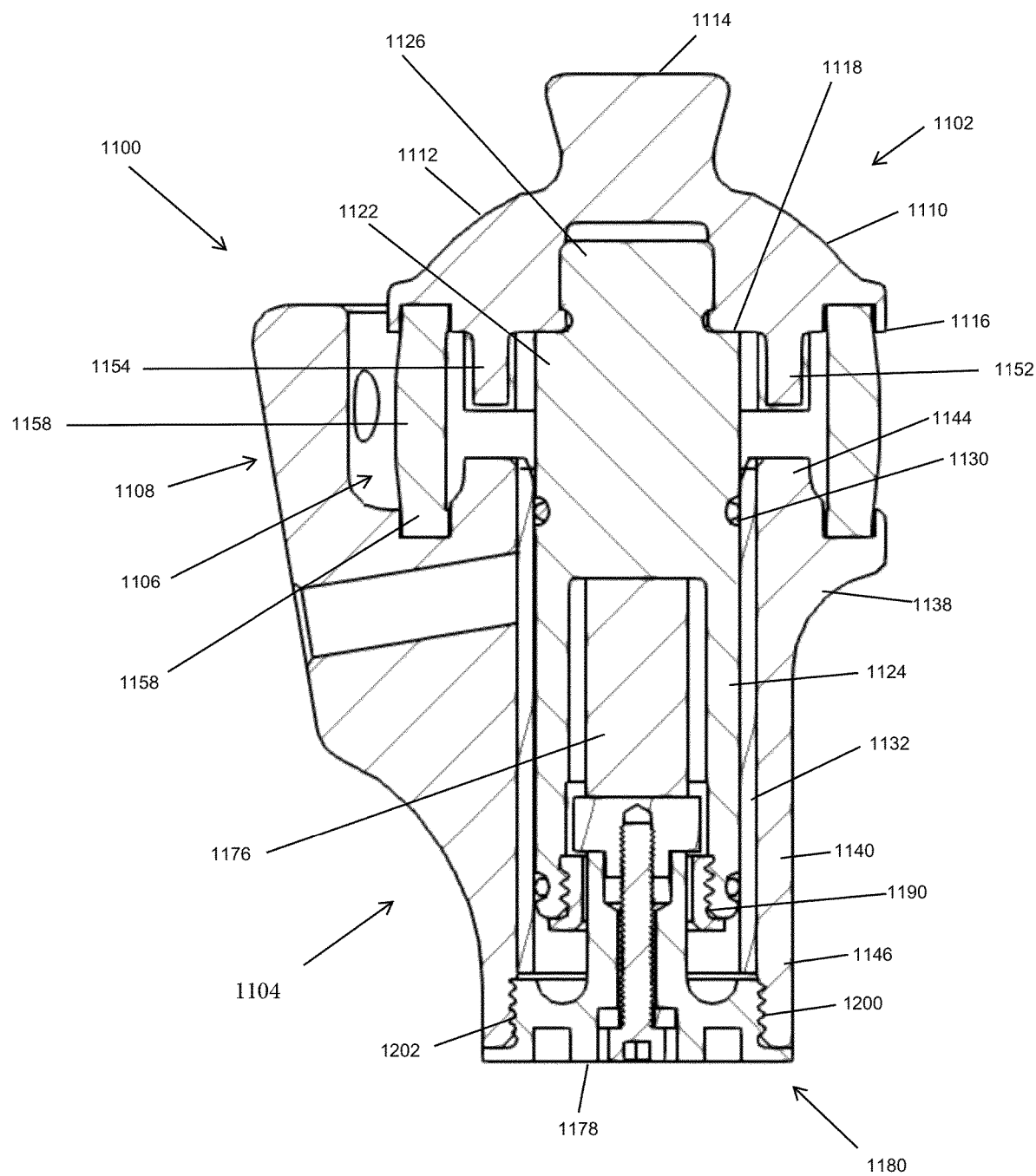
FIG. 57 is a side, cross-section view taken along the line H-H in FIG. 56 representatively illustrating portions of the mounting bracket in accordance with exemplary embodiments of the present technology.
Figure 58:
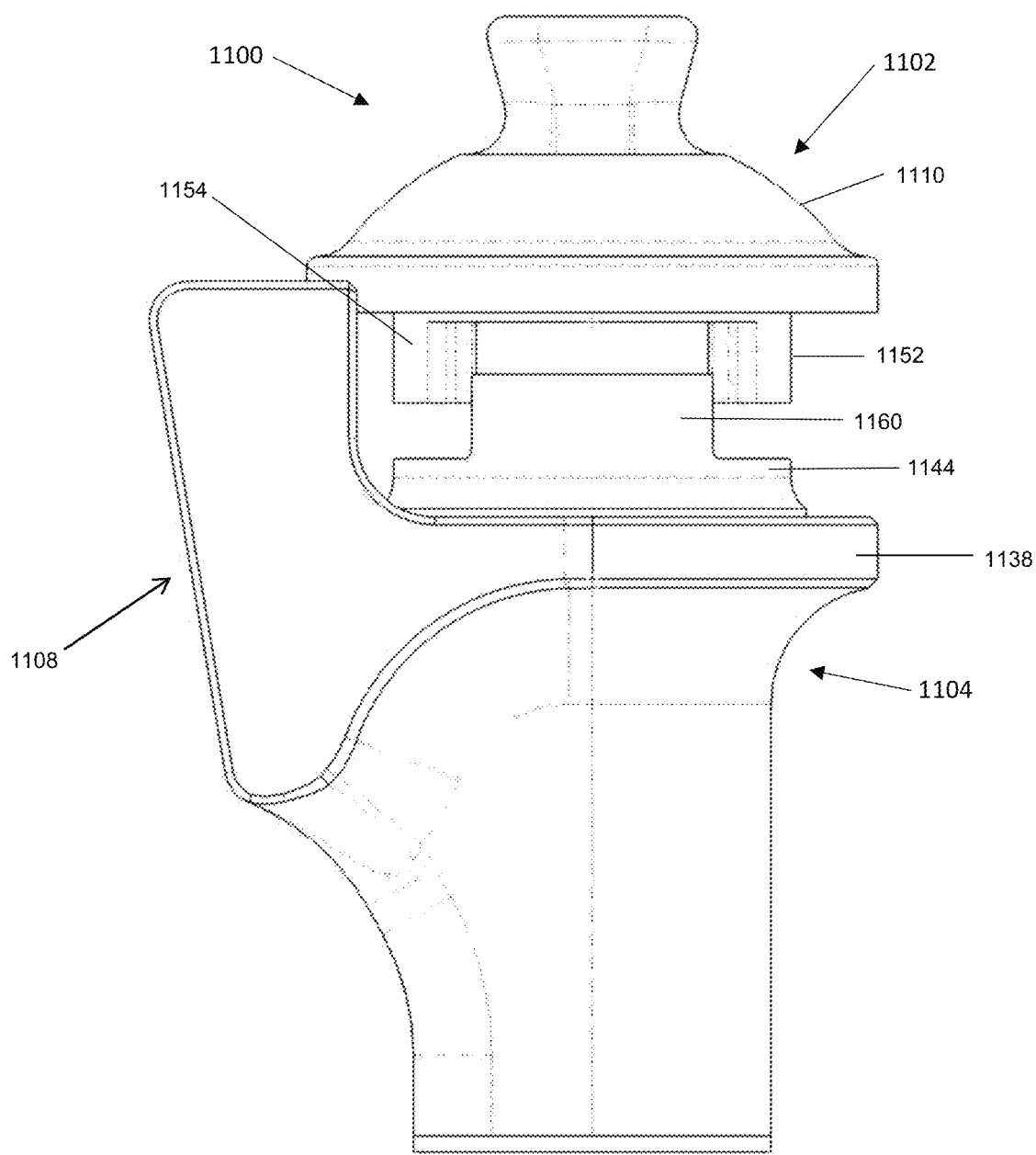
FIG. 58 is a side view of the mounting bracket showing upper and lower members and with the elastomeric ring removed.
Figure 75:
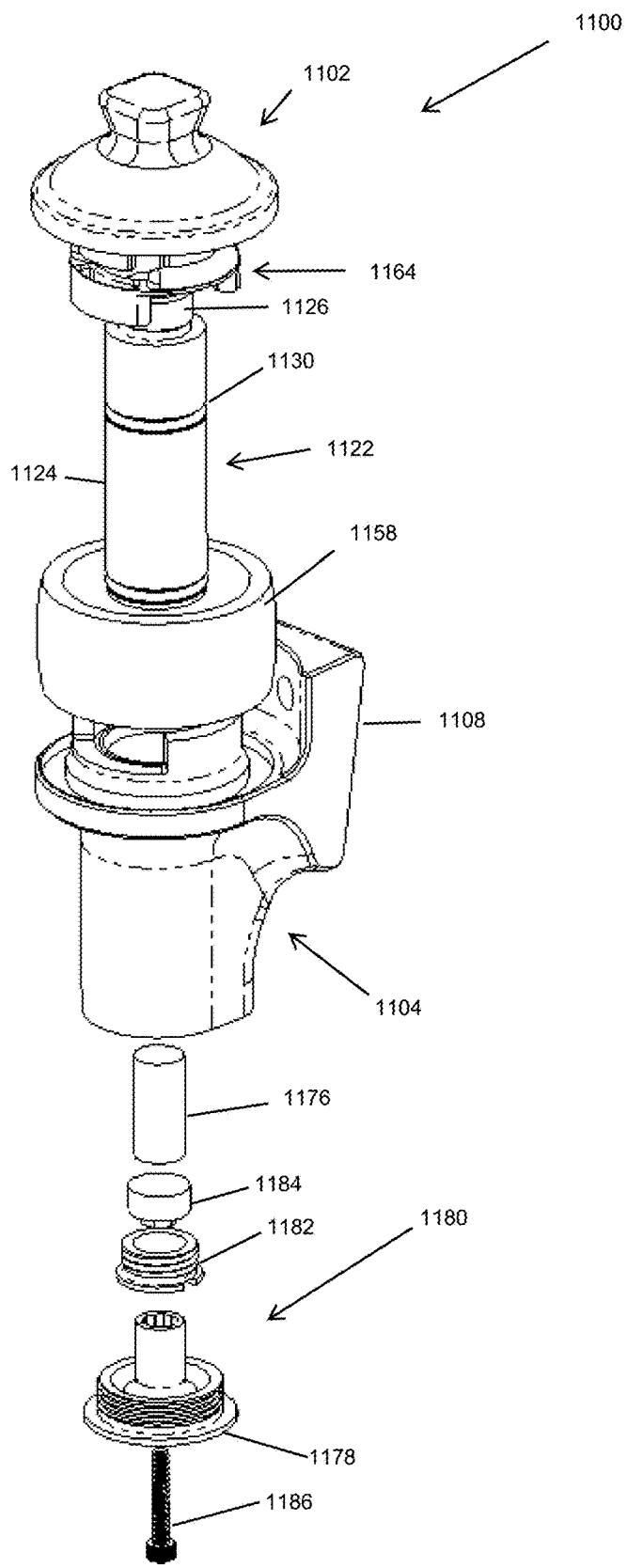
FIG. 75 is an exploded, perspective view representatively illustrating the mounting bracket in accordance with exemplary embodiments of the present technology.
Figure 76:
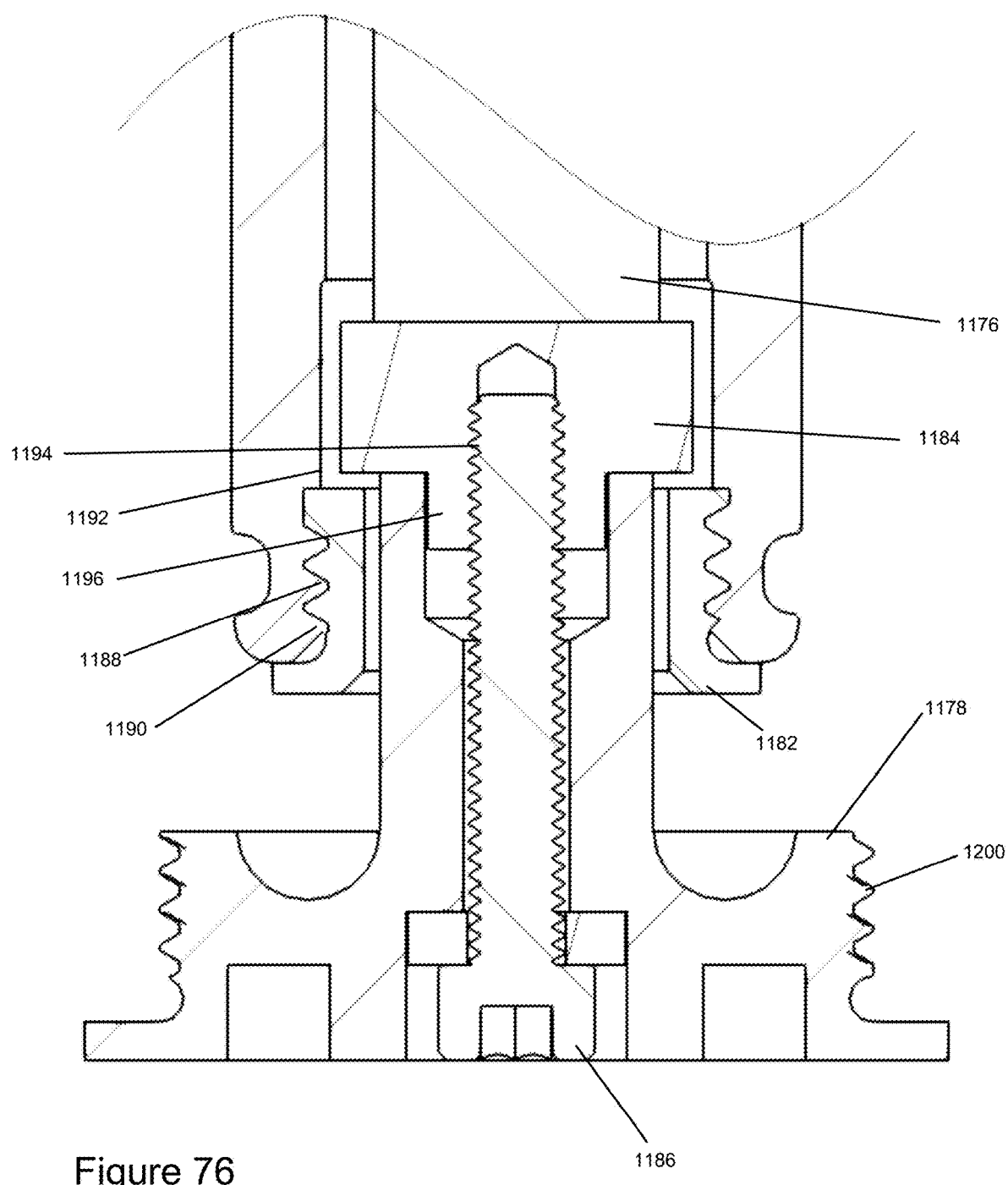
FIG. 76 is a side, cross-section view of a retention system in accordance with exemplary embodiments of the present technology.

Referring now to FIGS. 56, 57 and 75, in various embodiments, an additional embodiment of a mounting bracket 1100 is shown. Like the previous mounting brackets discussed above, the mounting bracket 1100 may be attached to the top member 120 of the prosthetic foot 100 and configured for attachment to a user. In various embodiments, the mounting bracket 1100 may comprise an upper member 1102, a lower member 1104, and a compression torsion joint 1106. The upper member 1102 may be configured for attachment to a user's residual limb. The lower member 1104 may be configured to attach to a prosthetic foot 100. In one embodiment the lower member 1104 is coupled to the prosthetic foot 100.

Figure 67:
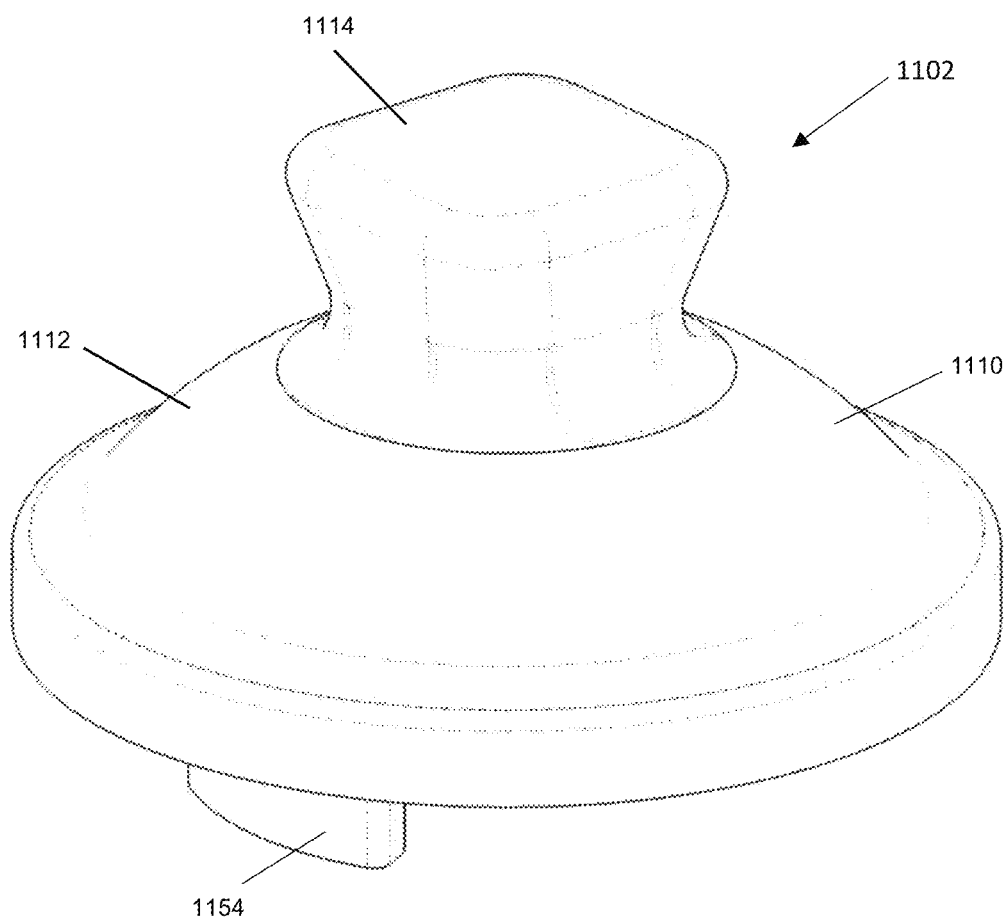
FIG. 67 is a top, perspective view of the upper member of the mounting bracket in accordance with exemplary embodiments of the present technology.
Figure 70:
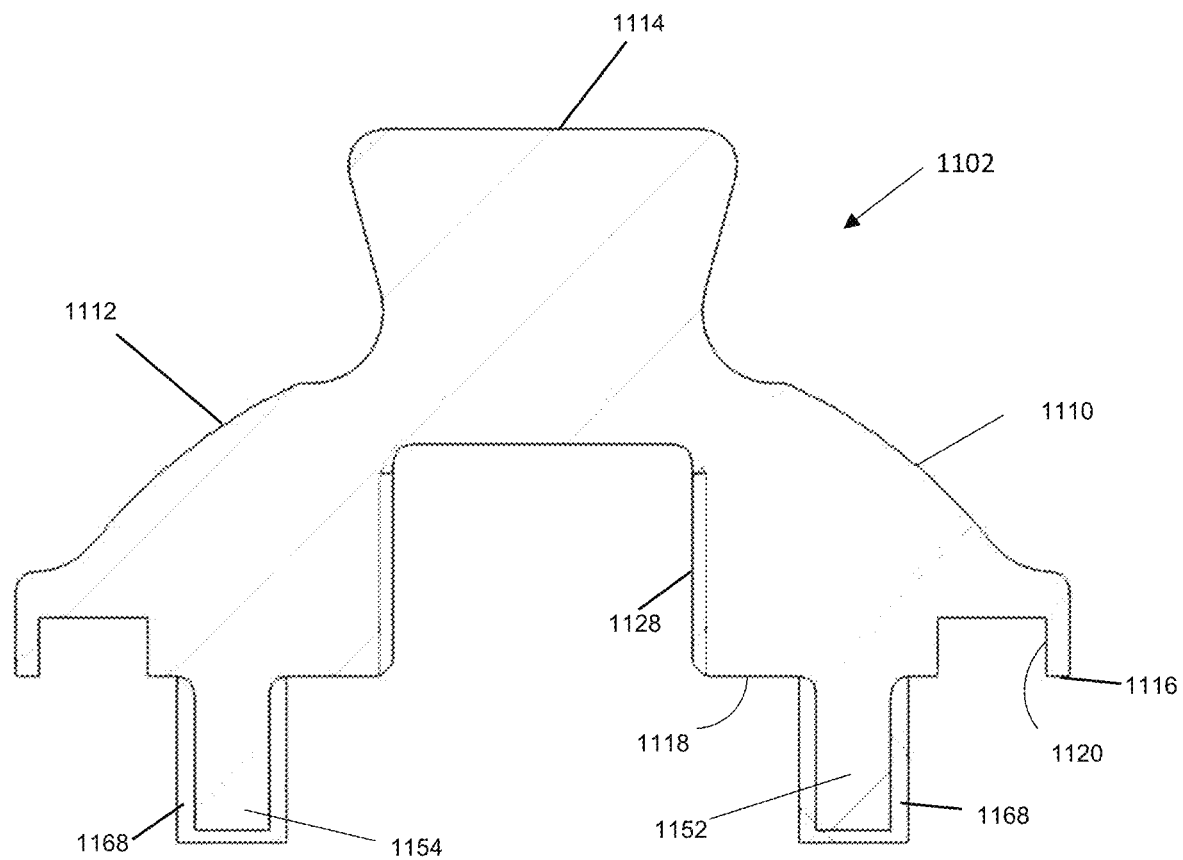
FIG. 70 is a front, cross-section view taken along the line J-J in FIG. 59 of the upper member of the mounting bracket in accordance with exemplary embodiments of the present technology.
Figure 71:
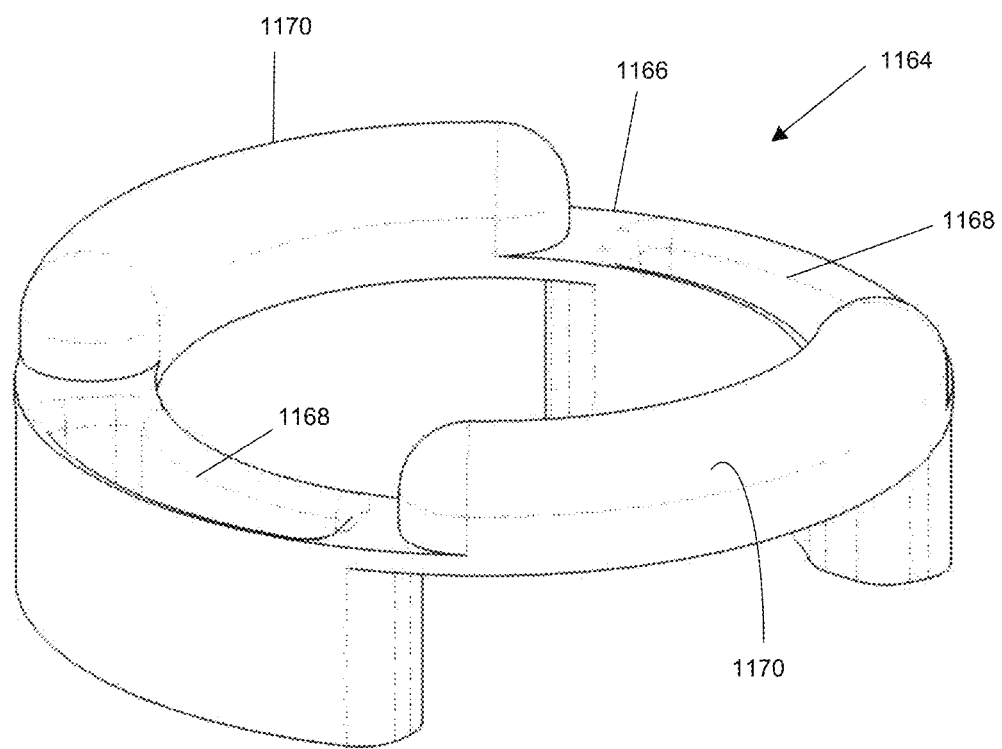
FIG. 71 is a perspective view of an internal bumper which facilitates the coupling of the upper member and lower member of the mounting bracket in accordance with exemplary embodiments of the present technology.
Figure 72:
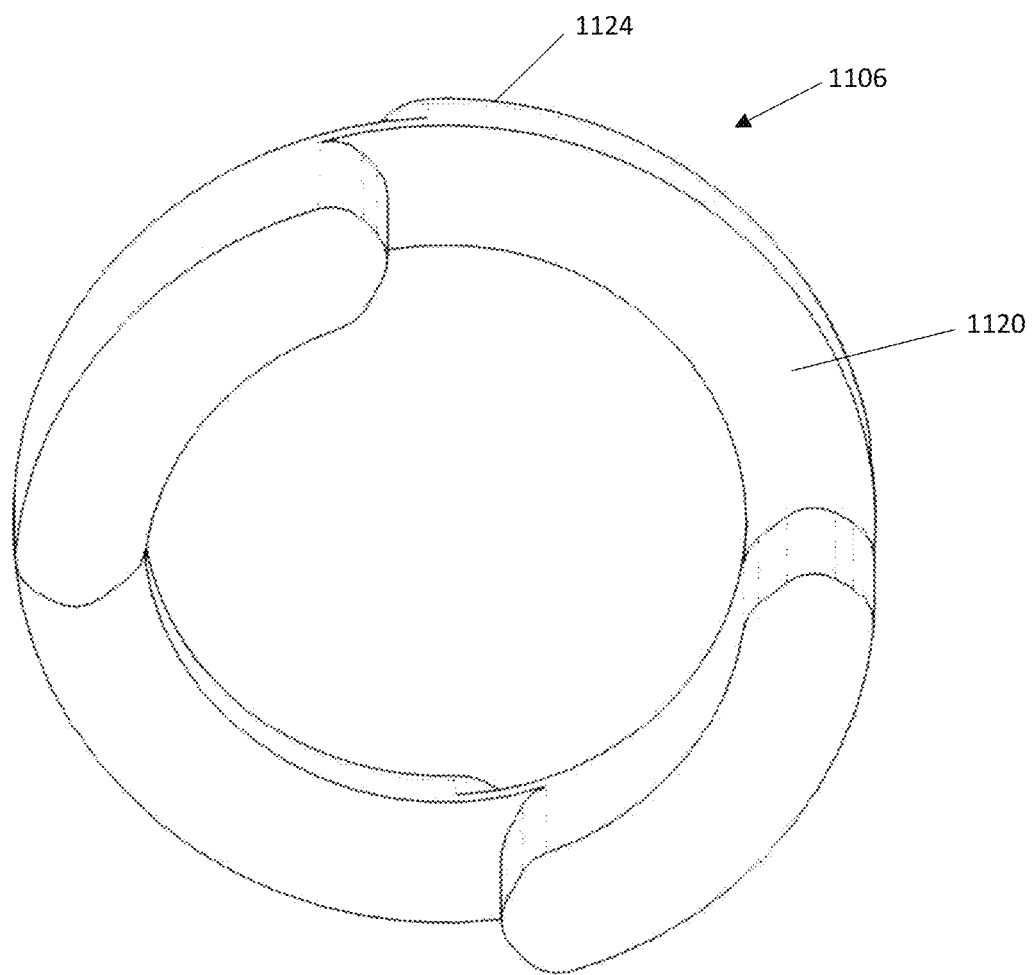
FIG. 72 is a lower, perspective view of the internal bumper of the mounting bracket in accordance with exemplary embodiments of the present technology.
Figure 73:
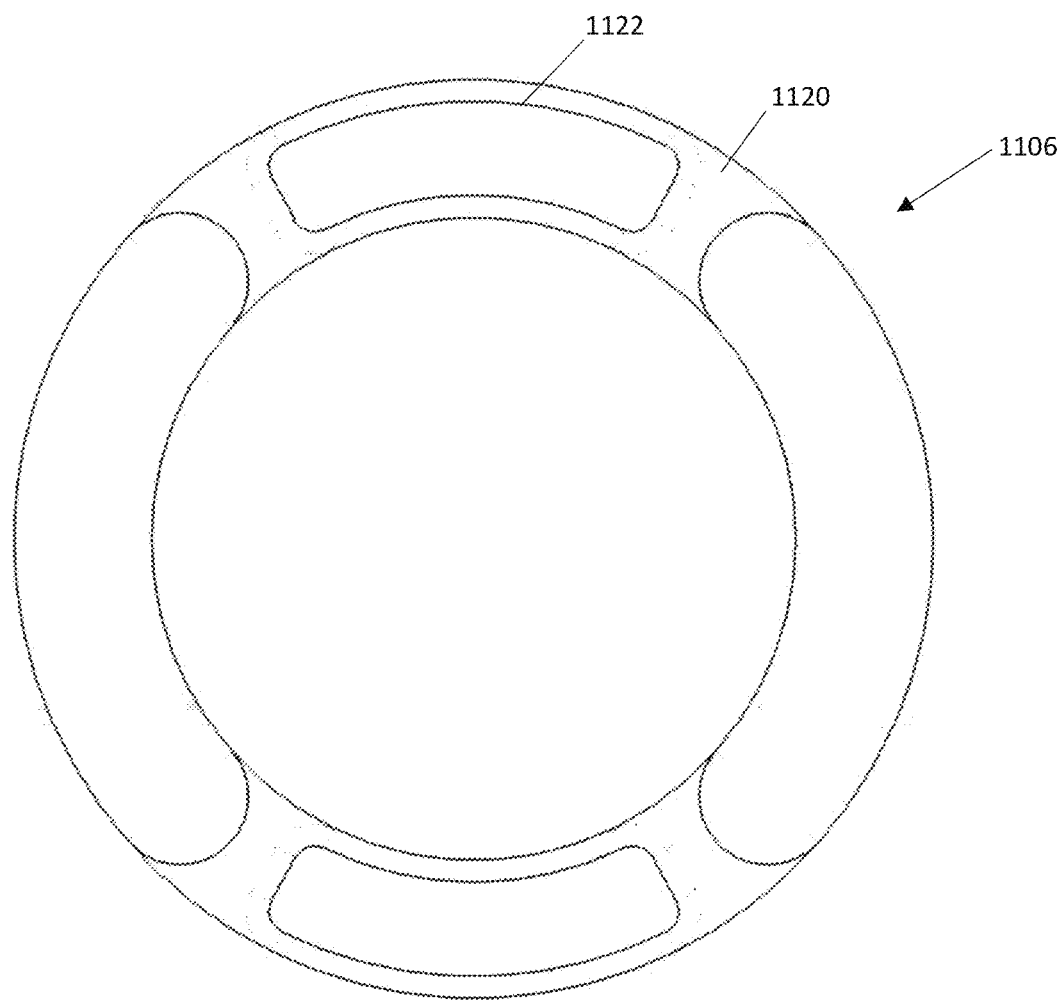
FIG. 73 is a bottom view of the internal bumper of the mounting bracket in accordance with exemplary embodiments of the present technology.
Figure 74:
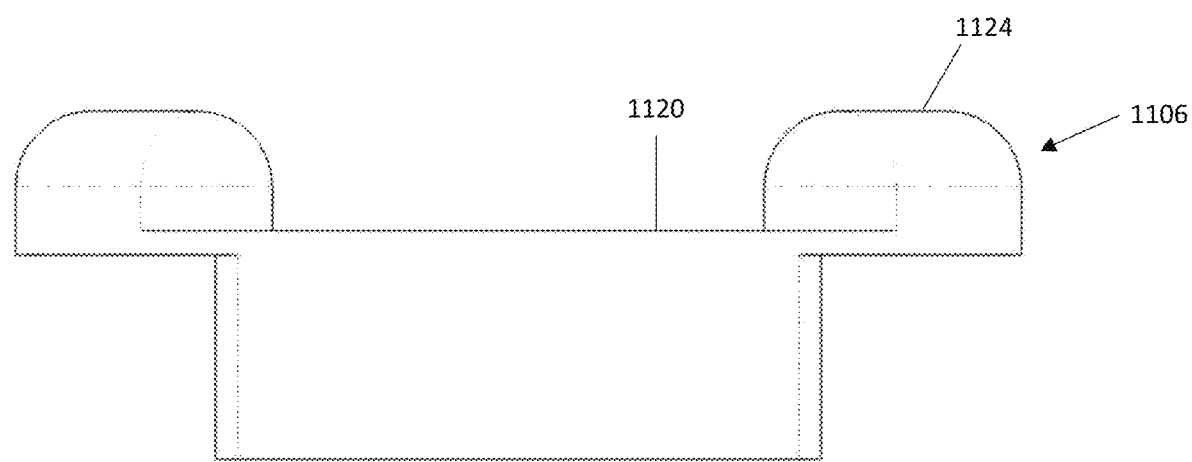
FIG. 74 is a side view of the internal bumper of the mounting bracket in accordance with exemplary embodiments of the present technology.

Referring now to FIGS. 57, 67 and 70, the upper member 1102 may comprise mounting portion 1108 and an upper flange 1110. The mounting portion 1108 may be configured to attach to a user's residual limb. The mounting portion 1108 may comprise a spherical dome 1112 and an attachment portion 1114, which is a standard male pyramid adapter used in the prosthetic industry. The pyramid adapter may be coupled with a standard receiver used in the practice of prosthetics, for example, a Staats style attachment, which is commonly known in the prosthetic industry. The attachment portion 1114 may use a standard receiver adapter, as understood by one of ordinary skill in the art. According to various embodiments the attachment portion 1114 may facilitate attachment to the residual limb of the user. The attachment portion 1114 may comprise a centerline that is aligned with the weight line of the user.

The spherical dome 1112 may be located on the upper flange 1110. In various embodiments, shown in FIGS. 57, 66, and 70 the upper flange 1110 may comprise a downwardly depending lip 1116 around its perimeter and a lower surface 1118 with a channel 1120 contained therein.

In various embodiments, as shown in FIGS. 57 and 75, the mounting bracket 1100 may also comprise a mating post 1122, similar to mating post 826 shown in FIGS. 27A and 27B and mating post 1022 shown in FIGS. 44, 52A and 52B above. The mating post 1122 may comprise a cylindrical collar 1124 depending downwardly from a lower surface 1118 of the upper flange 1110 once the mating post 1122 is coupled with the upper member 1102. In various embodiments the mating post 1122 may be a separate component that is removable or may be an integral piece. An upper portion 1126 of the mating post 1122 (see also FIG. 75) may be coupled to the upper member 1102 within a recess 1128 (see also FIG. 70) by any known method, such as screw fit, pressed, and the like. In one embodiment the mating post 1122 may be coupled to the upper member 1102 by a threaded connection. The mating post 1122 may comprise threads (not shown) on the upper portion 1126 of the cylindrical collar 1124 that are received by threads (not shown) within the recess 1128 in the upper member 1102. The mating post 1122 may further comprise at least one recess 1130 (see also FIG. 75) on the perimeter of the cylindrical collar 1124 that may receive O-rings (not shown). The O-rings serve to fill the clearance between the outer diameter of mating post 1122 and the inner diameter of a sleeve 1132 to provide smooth, and silent action between relatively moving components. In one embodiment, the mating post 1122 comprises at least one recess 1034 (See FIGS. 52A and 52B) on the perimeter of the cylindrical collar 1124 that may receive grease or another lubricant during assembly.

Referring now to FIGS. 57 and 60-64, in various embodiments, the lower member 1104 may comprise the mounting portion 1108, a lower flange 1138, and a mating portion 1140. The mounting portion 1108 may be located at a rear edge of the lower flange 1138. The mounting portion 1108 may comprise at least one threaded aperture 1142 used to couple the mounting bracket 1100 to the prosthetic foot 100. In one embodiment, the mounting portion 1108 comprises 3 threaded apertures 1142 which receive fasteners to couple the mounting bracket 1100 to the prosthetic foot 100.

In various embodiments, as shown in FIG. 9, an upper end 862 of the prosthetic foot 100 may be connected to the mounting portion 1108 of the lower member 1104 via mechanical connection whereby fasteners 864 are received within apertures (not shown) residing in the upper end 862 of the prosthetic foot 100 and the mounting portion 1108 of lower member 1104. While the 1000, 1100 mounting bracket is not shown in FIG. 9, the mounting bracket 1000, 1100 may be coupled in the same manner as mounting bracket 800. While a bolted connection is shown any mechanical connection may be contemplated, such as screws, rivets, and the like. The bolted connection materials may comprise Titanium or any other suitable material. Other types of material may comprise mild steel, alloy steel, high strength stainless steel such as 13-8, and alloy aluminum such as the 2000 and 7000 series.

Figure 61:
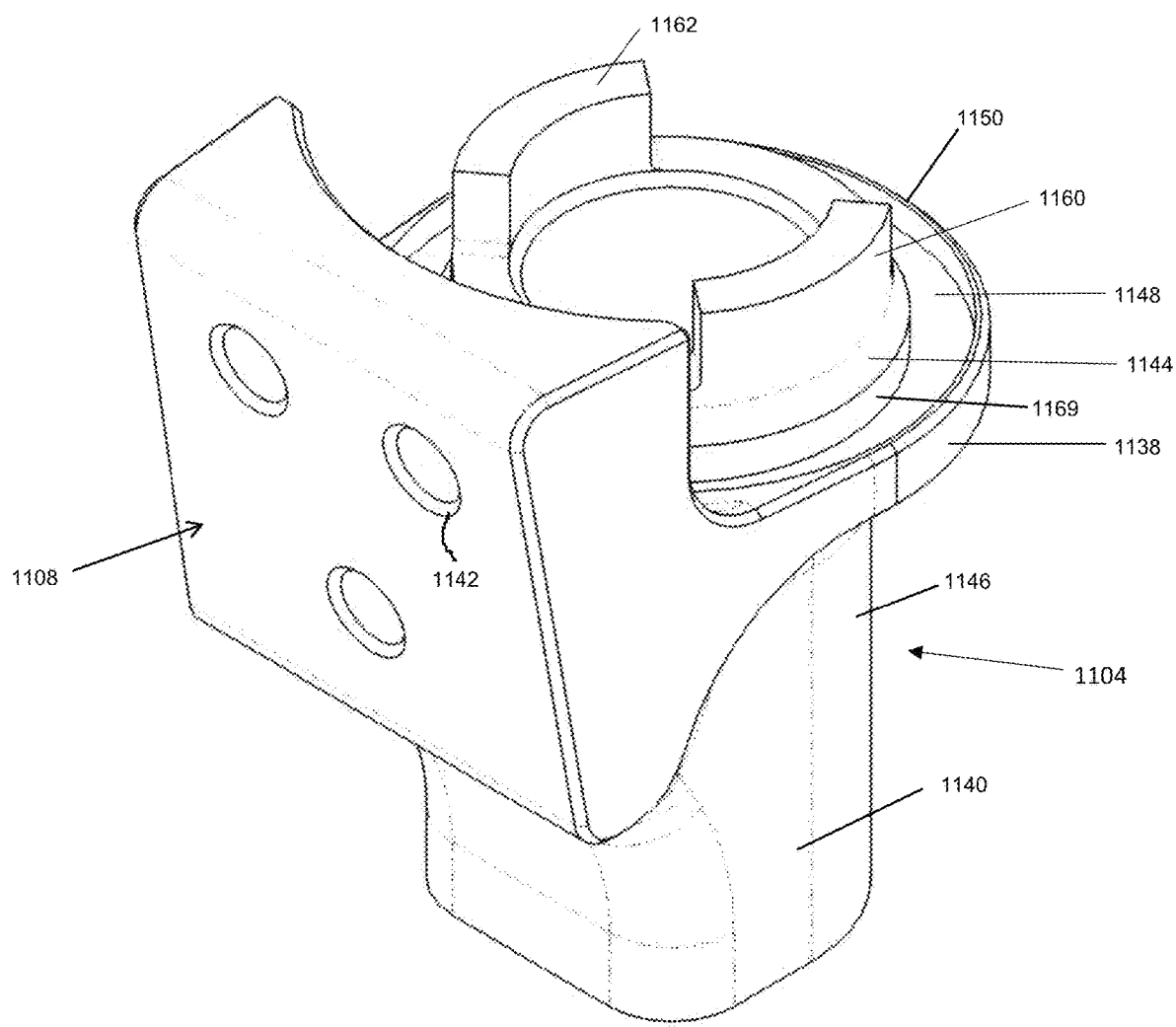
FIG. 61 is a rear perspective view of a lower member of the mounting bracket in accordance with exemplary embodiments of the present technology.
Figure 62:
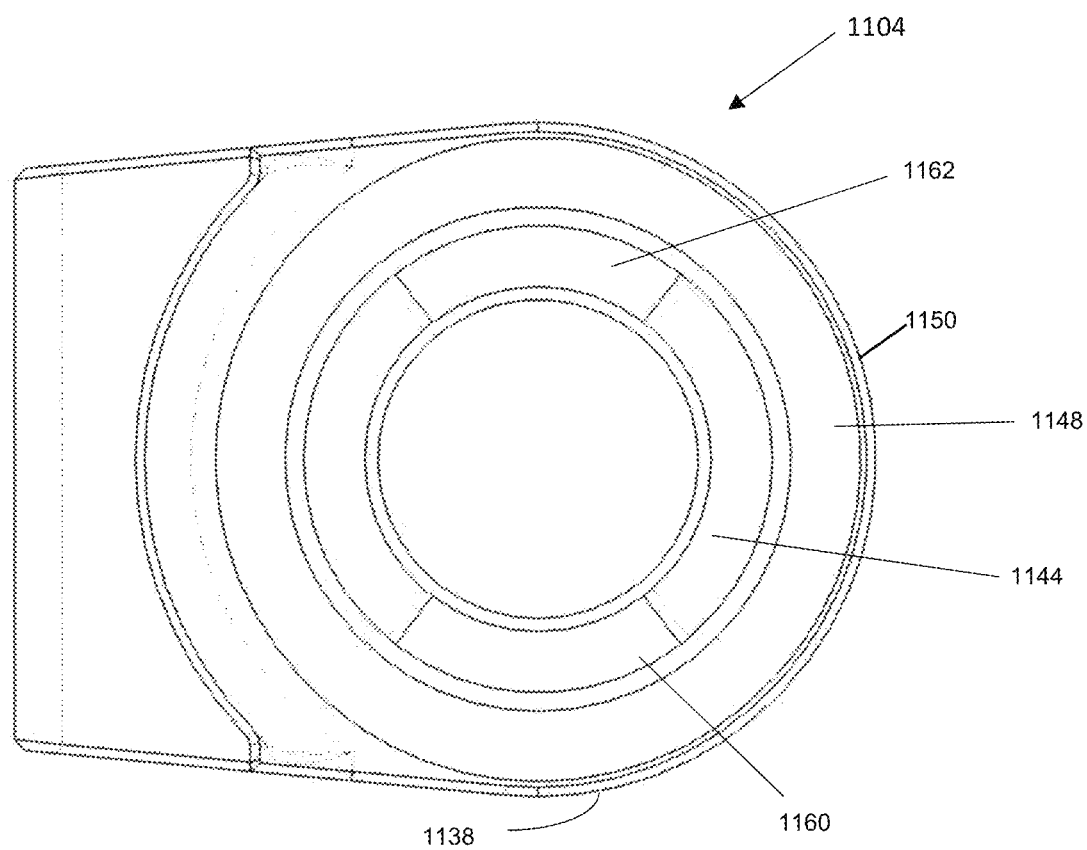
FIG. 62 is a top view of the lower member of the mounting bracket in accordance with exemplary embodiments of the present technology.
Figure 63:
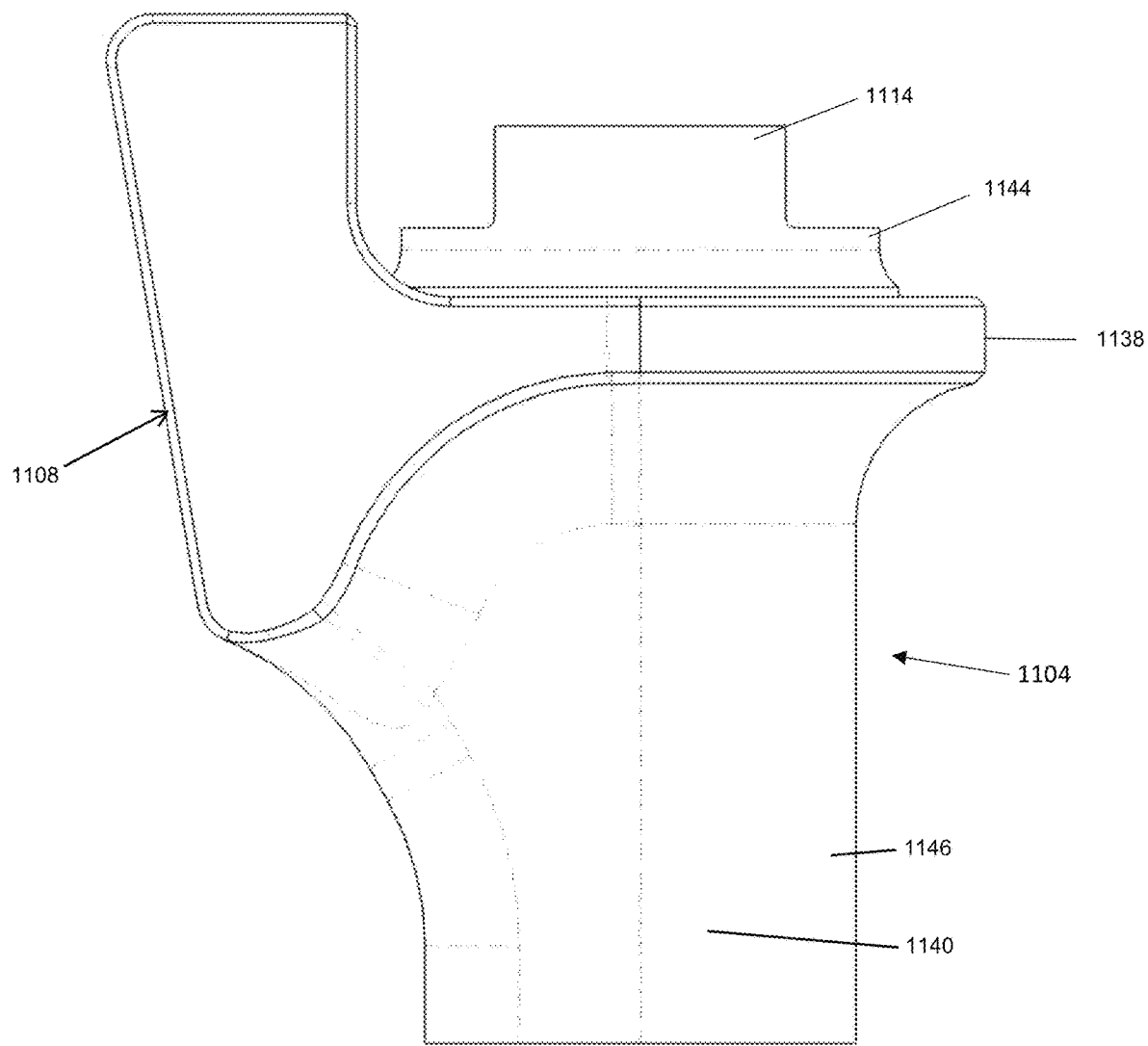
FIG. 63 is a side view of the lower member of the mounting bracket in accordance with exemplary embodiments of the present technology.
Figure 64:
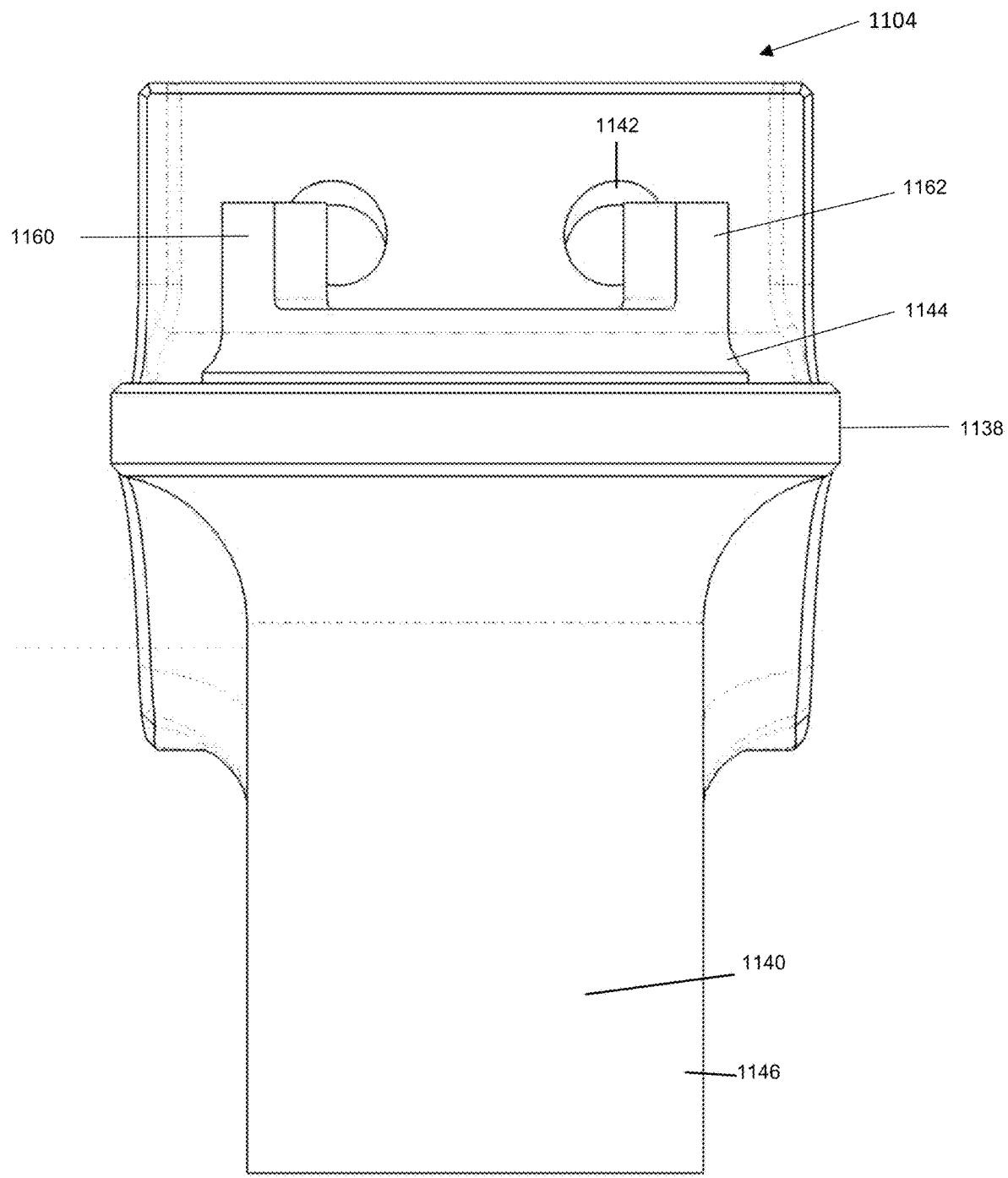
FIG. 64 is a front view of the lower member of the mounting bracket in accordance with exemplary embodiments of the present technology.
Figure 65:
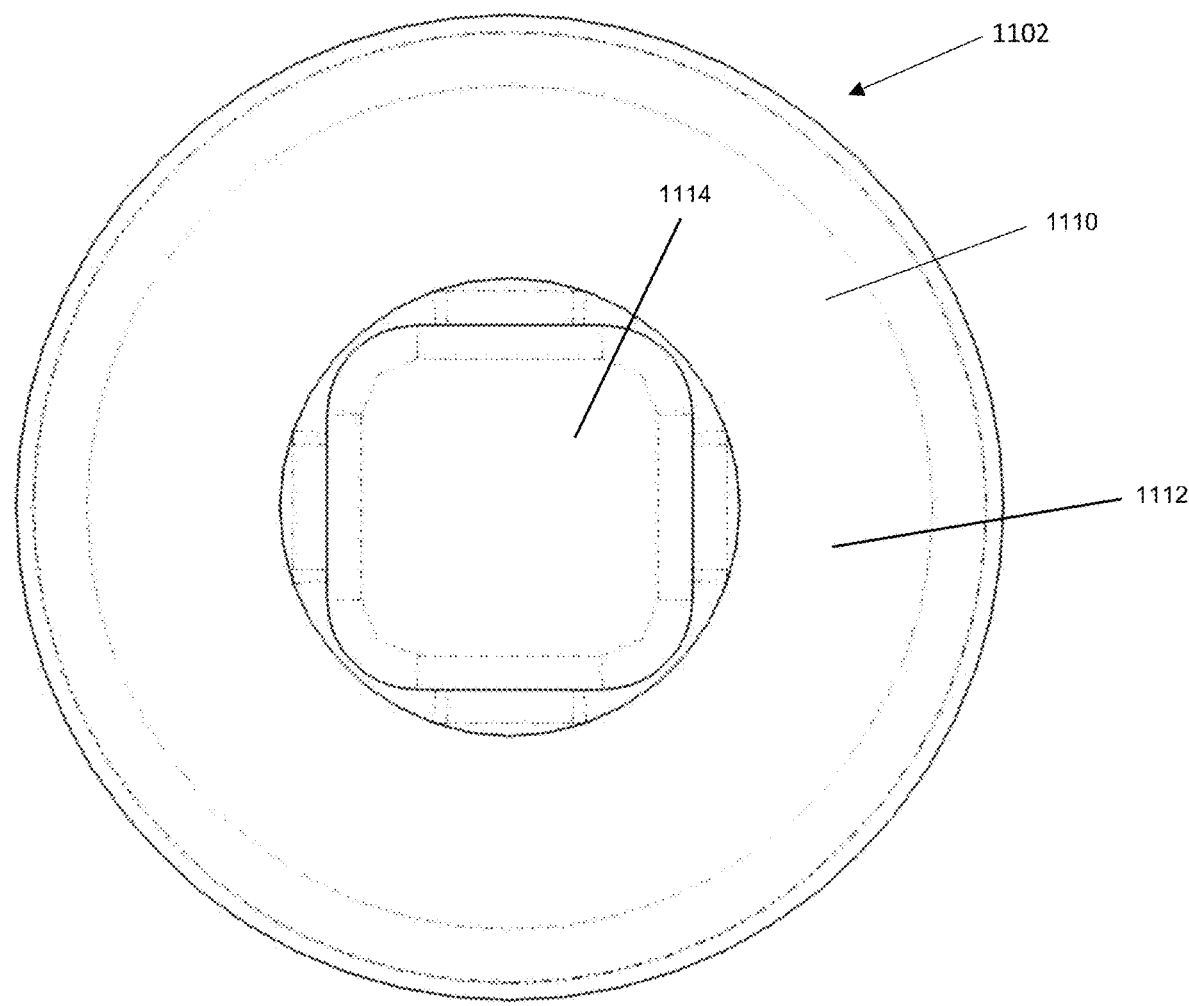
FIG. 65 is a top view of an upper member of the mounting bracket in accordance with exemplary embodiments of the present technology.

The mating portion 1140 of the lower member 1104 may comprise an upper collar 1144 and a lower collar 1146. The upper collar 1144 depends upwardly from the lower flange 1138 while the lower collar 1146 depends downwardly from the lower flange 1138. As shown in FIG. 57, the upper and lower collars 1144, 1146 of the mating portion 1140 combine to receive the cylindrical collar 1124 of the mating post 1122 when the upper and lower members 1102, 1104 are connected. As shown in FIGS. 61 and 62, the lower flange 1138 may comprise a recessed channel 1148 and a lip 1150 surrounding at least a portion of the perimeter.

Figure 66:
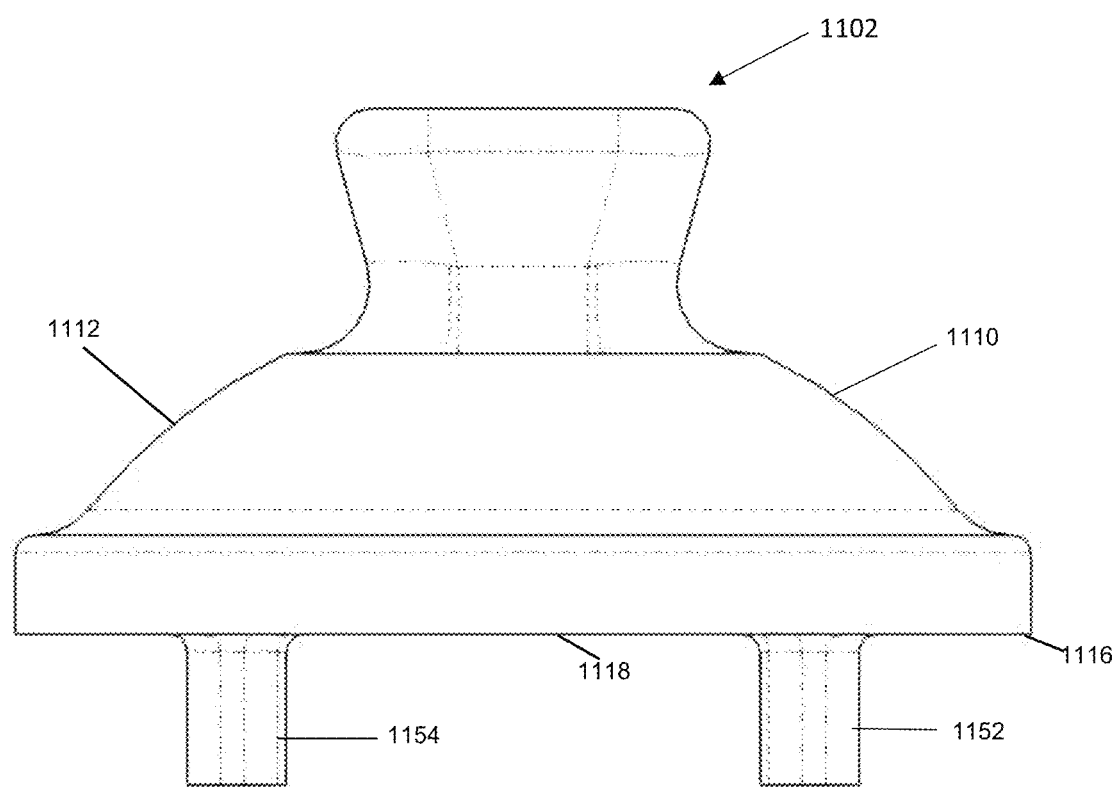
FIG. 66 is a side view of the upper member of the mounting bracket in accordance with exemplary embodiments of the present technology.
Figure 68:
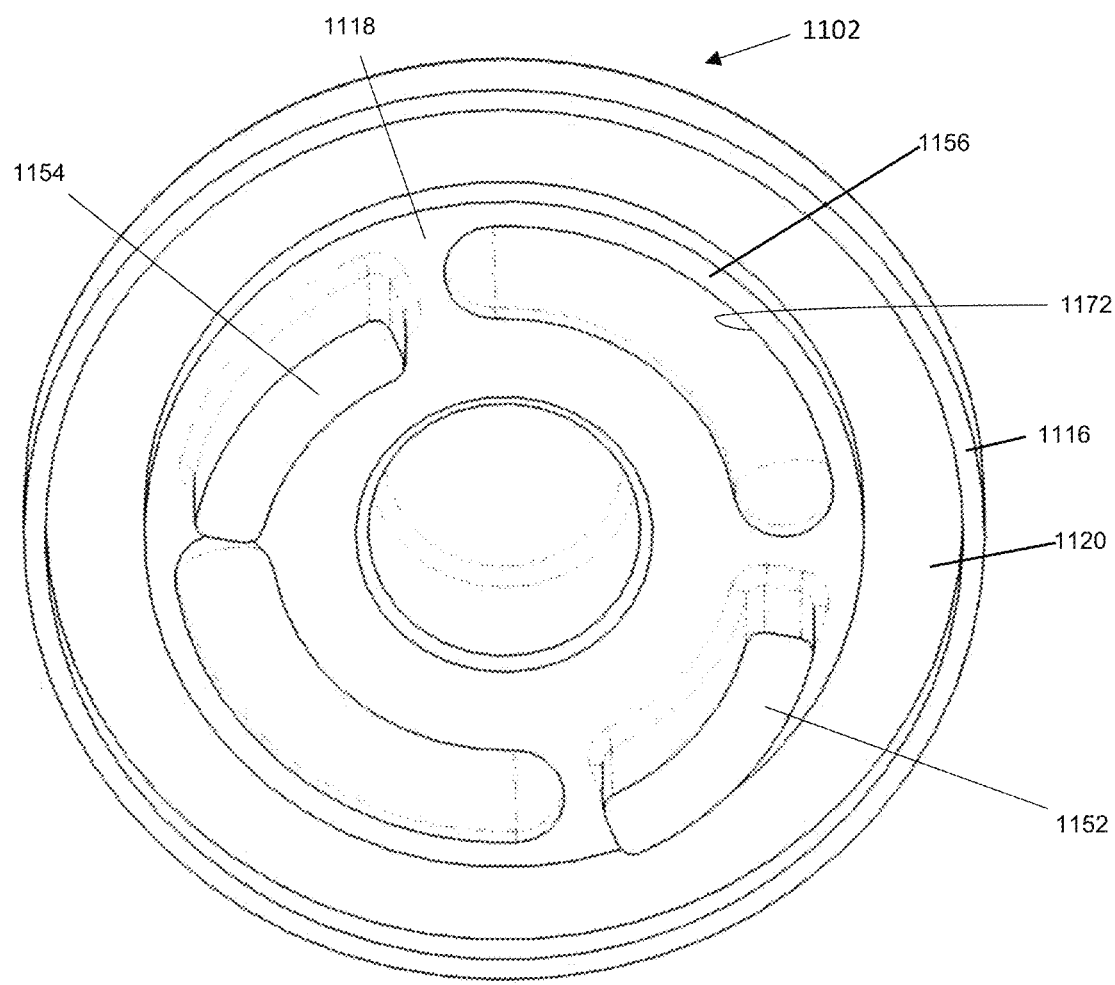
FIG. 68 is a lower, perspective view of the upper member of the mounting bracket in accordance with exemplary embodiments of the present technology.
Figure 69:
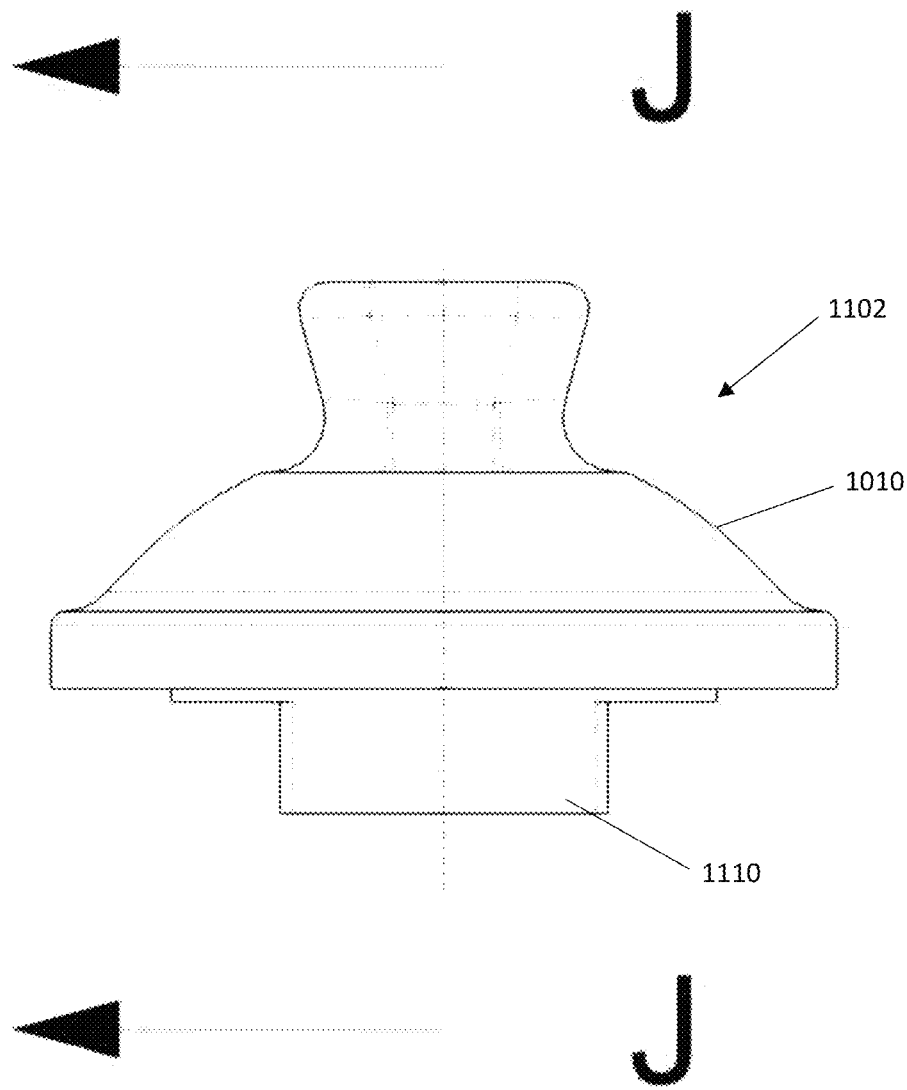
FIG. 69 is a front view of the upper member of the mounting bracket in accordance with exemplary embodiments of the present technology.

In various embodiments, referring now to FIGS. 66 and 68, the upper member 1102 may comprise at least one ear depending from the lower surface 1118 of the upper flange 1110. In one embodiment the upper member 1102 may comprise a pair of depending ears 1152 and 1154. The ear or ears 1152 and 1154 may depend downwardly from the lower surface 1118 of the upper flange 1110. As shown in FIG. 68, the ear or ears 1152 and 1154 may be located inwardly of the channel 1120 on lower surface 1118 the upper flange 1110 such that they are contained within the outer perimeter of the upper and lower members 1102, 1104 and inside of an elastomeric ring 1158 (see also FIG. 57). The ear or ears 1152 and 1154 may be located The ear or ears 1152 and 1154 serve to limit rotation of the upper member 1102 with respect to the lower member 1104 during use as will be discussed in detail below. The ear or ears 1152 and 1154 may reside on the upper member 1102 adjacent and inwardly from an inner perimeter 1156 of the channel 1120 located on upper flange 1110 and project downwardly therefrom. As shown in FIG. 68, the ears 1152 and 1154 may reside on the lower surface 1118 of the upper member 1102 opposite one another and inward from an inner perimeter 1156 of the channel 1120 located on upper flange 1110 and project downwardly therefrom.

Referring now to FIGS. 58, 59 and 61-64, in various embodiments, the lower member 1104 may comprise at least one ear depending upwardly from the upper collar 1144 of the lower flange 1138. In one embodiment the lower member 1104 may comprise a pair of depending ears 1160 and 1162. The ear or ears 1160 and 1162 depend upwardly from the upper collar 1044 of the lower flange 1138. The ear or ears 1160 and 1162 are located inwardly of the channel 1148 on the upper collar 1144 of the lower flange 1138 such that they are fully contained within the outer perimeter of the upper and lower members 1102, 1104 and inside of the elastomeric ring 1158. As shown in FIG. 61, the ears 1160 and 1162 may be located opposite of one another on the upper collar 1144 inward of an interior perimeter 1169 of the channel 1148.

While the upper member 1102 and lower member 1104 are shown with pairs of depending ears, one of the upper and lower members may comprise a single depending ear, while the other comprises a pair of depending ears. As such, in one embodiment, a single depending ear may be included on one of the upper and lower members while the other comprises a pair of depending ears. For example, in one embodiment the upper member 1102 may comprise a pair of ears 1152 and 1154 depending downwardly from the upper collar 1044 of the lower flange 1138 and the lower member 1104 may comprise at least one ear depending upwardly from the upper collar 1044 of the lower flange 1138.

Referring now to FIG. 71-74 an internal bumper 1164 will be discussed. The internal bumper 1164 may comprise a ring 1166, a pair of recesses 1168, and a pair of depending arms 1170. The ring 1166 resides inwardly of the channels 1120 and 1148 of the upper and lower members 1102, 1104, respectively. The internal bumper 1164 may comprise a torsion stop resilient material. The internal bumper 1164 may be comprised of elastomeric material similar to the material described above with regards to the elastomeric ring 1158, the torsion limiter 1056, and vertical spring 1176. The internal bumper 1164 may be formed as a single piece, as shown, or multiple pieces. The primary function of the recesses 1168 of the internal bumper 1164 is to encase the pair of depending ears 1152 and 1154 of the upper member 1102 (See FIG. 70) to eliminate any metal on metal contact at the end of the rotational motion when depending ears 1152 and 1154 of the upper member 1102 are rotated to contact the depending ears 1160 and 1162 of the lower member 1104.

The pair of depending arms 1170 may comprise bumpers for the end of vertical travel. The pair of depending arms 1170 protrude upwardly and are inserted within a pair of recessed slots 1172 in the upper dome body of the upper member 1102, See FIG. 68. In use, depending ears 1160 and 1162 of the lower member 1104 will contact the pair of depending arms 1170 when the end of vertical travel is reached and prevent the metal on metal contact for end of vertical travel, just as it does for the encased pair of depending ears 1152 and 1154 of the upper member 1102 during rotational travel.

The internal bumper 1164 may be modified in accordance with the orientation of the ears on the upper and lower members 1102, 1104. For example, as shown in FIGS. 71-74, if the upper member 1102 comprises a pair of depending ears 1152 and 1154, the internal bumper will comprise a pair of recesses to accommodate the pair of depending ears 1152 and 1154. If the upper member 1102 comprises a single depending ear, the internal bumper will comprise a single recesses to accommodate the single of depending ear.

Figure 81:
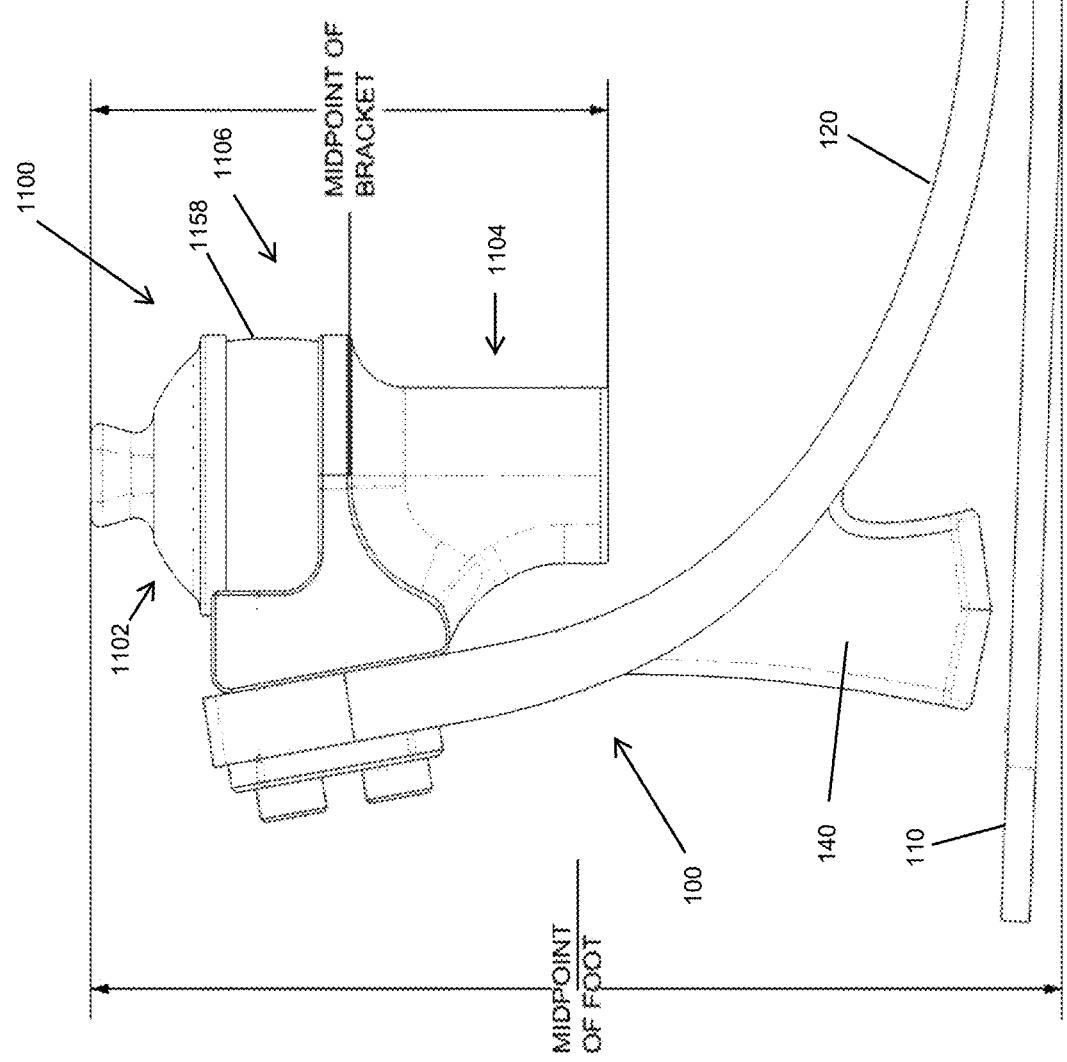
FIG. 81 is a side view representatively illustrating the mounting bracket shown in FIGS. 56-57 on a prosthetic foot in accordance with exemplary embodiments of the present technology.

In various embodiments, referring to FIGS. 57 and 75, the compression torsion joint 1106 may comprise an elastomeric ring 1158. In various embodiments, the compression torsion joint 1106 may comprise the internal bumper 1164. In various embodiments, the compression torsion joint 1106 may comprise a vertical spring 1176. In one embodiment, the compression torsion joint 1106 may comprise a combination of the elastomeric ring 1158, internal bumper 1164, and the vertical spring 1176. In one embodiment, shown in FIG. 81, the compression torsion joint 1106 may be located above a midpoint of a height of the mounting bracket 1100. In one embodiment, shown in FIG. 81, the compression torsion joint 1106 may be located above a midpoint of a height of the prosthetic foot 100. The compression torsion joint 1106 is placed in close proximity to the mounting portion 1108 of the mounting bracket 1100, which attaches to the prosthetic foot 100 and to the user. This reduces moments/loads on the compression torsion joint 1106, the foot 100, and user. This placement, in conjunction with the foot design, permits the most compact and lightest-weight bracket solution for carrying the required loads while allowing the compression and torsion motions. Further, in one embodiment, the mounting bracket 1100 attaches to the prosthetic foot 100 nearly parallel to the vertical axis of the foot, which requires the compression torsion joint 1106 being above the midpoint of the mounting bracket 1100 to the prosthetic foot 100 by the lower member 1104 to accommodate the mounting of the bracket to the prosthetic foot 100.

In various embodiments, the elastomeric ring 1158 shown in FIG. 57 is similar to the elastomeric ring 1054 discussed above in FIGS. 19, 22A, 22B and 47-49. The elastomeric rings 1054/1158 generally may comprise a wall 1062 with inner 1064, outer 1066, upper 1068, and lower 1070 surfaces. In various embodiments, the inner surface 1064 of the wall 1062 may comprise a substantially smooth surface. In various embodiments, the inner surface 1064 may comprise a ridged surface, a surface with raised portions, and or a wall with varying thickness. In one embodiment, shown in FIGS. 47A-47C, the inner and outer surfaces 1064, 1066 may be curved from the upper 1068 to lower surface 1070, and/or concave with respect to the center of the elastomeric ring 1158. In one embodiment, the outer surface 1066 may be curved, and/or convex with respect to the center of the elastomeric ring 1054/1158. In one embodiment, shown in FIGS. 48A-48C, the inner surfaces 1064 may be generally straight and the and outer surfaces 1066 may be curved from the upper 1068 to lower surface 1070, and/or concave with respect to the center of the elastomeric ring 1054/1158. In one embodiment, shown in FIGS. 49A-49C, the inner and outer surfaces 1064, 1066 may be generally straight from the upper 1068 to lower surface 1070.

Referring now to FIGS. 43, 44, 47-50, and 57 the upper surface 1068 of the elastomeric ring 1054/1158 may be received in the channel 1120 in the upper flange 1110 in the upper member 1102. The outer surface 1066 generally abuts the lip 1016 of the upper flange 1110 of the upper member 1102. The lower surface 1070 of the elastomeric ring 1054/1158 may be received in the channel 1048 in the lower flange 1138 in the lower member 1104. The outer surface 1066 generally abuts the lip 1050 of the lower flange 1138 of the lower member 1104.

In various embodiments, referring to FIGS. 57 and 75 the vertical spring 1176 may be received within the cylindrical collar 1124 of the mating post 1122. The vertical spring 1176 may comprise an elastomeric material including but not limited to natural rubber, synthetic rubber, a combination of natural rubber and synthetic rubber, polyurethane, and the like. The vertical spring 1176 resists and limits the amount of vertical movement of the upper member 1102 with respect to the lower member 1104.

In various embodiments, the vertical spring 1176 may reside between a lower surface of the cylindrical collar 1124 and a compression cap 1178. In one embodiment, the vertical spring 1176 may reside between a spacer (not shown) located within the cylindrical collar 1124 and the compression cap 1178. The vertical spring 1176 limits the amount of vertical movement of the upper member 1102 with respect to the lower member 1104 by contacting the lower surface of the cylindrical collar 1124 within the mating post 1122 and the compression cap 1178.

Referring now to FIGS. 57 and 75-77, in various embodiments, the mounting bracket 1100 may comprise a retention system 1180. The retention system 1180 is utilized as a failsafe to ensure that the upper member 1102 does not disconnect from the lower member 1104 in the situation where the bond on the elastomeric ring 1158 that connects the upper and lower members 1102, 1104 fails. In various embodiments, the retention system 1180 may comprise a retention ring 1182, a plug 1184, and a retention connector 1186.

Figure 78A:
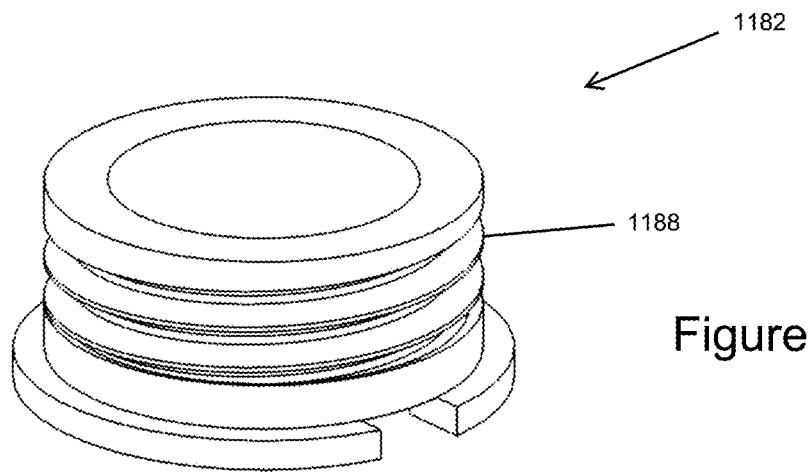
FIG. 78A is a perspective view of a retention ring for the retention system in accordance with exemplary embodiments of the present technology.
Figure 78B:
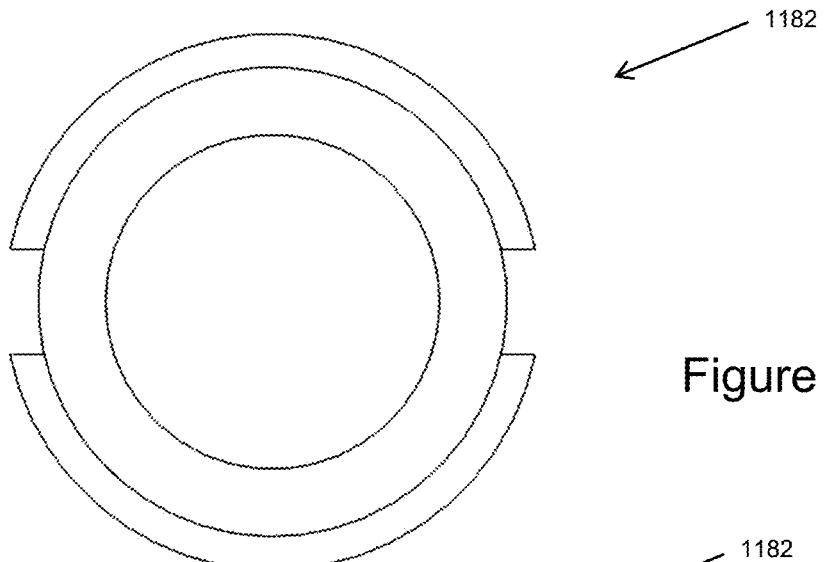
FIG. 78B is a top view of the retention ring for the retention system in accordance with exemplary embodiments of the present technology.
Figure 78C:
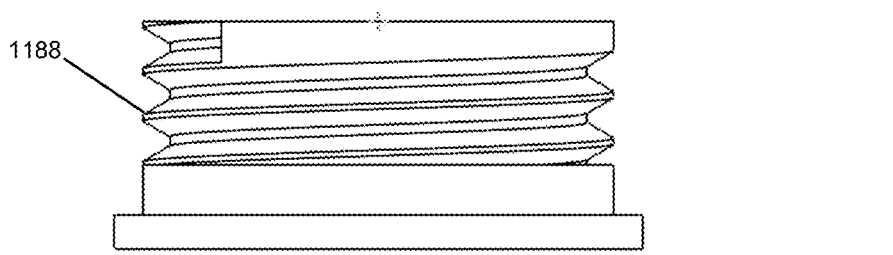
FIG. 78C is a side view of the retention ring for the retention system in accordance with exemplary embodiments of the present technology.
Figure 79A:
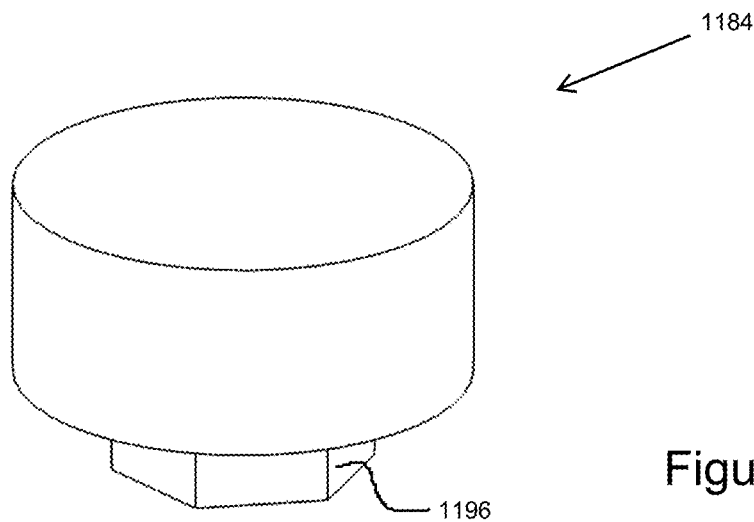
FIG. 79A is a perspective view of a plug for the retention system in accordance with exemplary embodiments of the present technology.
Figure 79B:
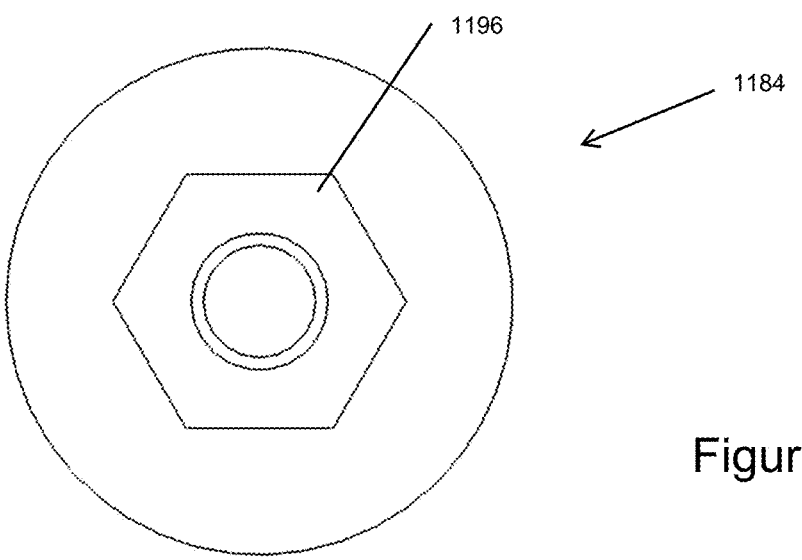
FIG. 79B is a top view of the plug for the retention system in accordance with exemplary embodiments of the present technology.
Figure 79C:
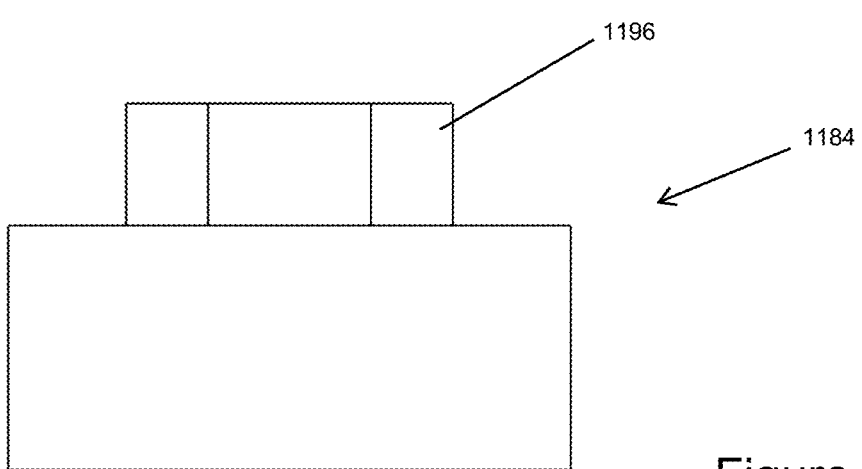
FIG. 79C is a side view of the plug for the retention system in accordance with exemplary embodiments of the present technology.
Figure 80A:
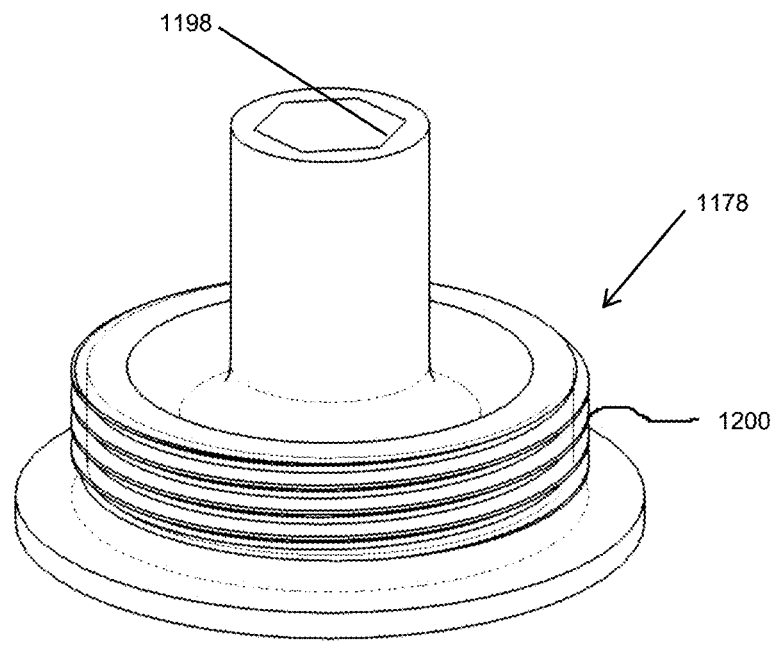
FIG. 80A is a perspective view of a compression collar in accordance with exemplary embodiments of the present technology.
Figure 80B:
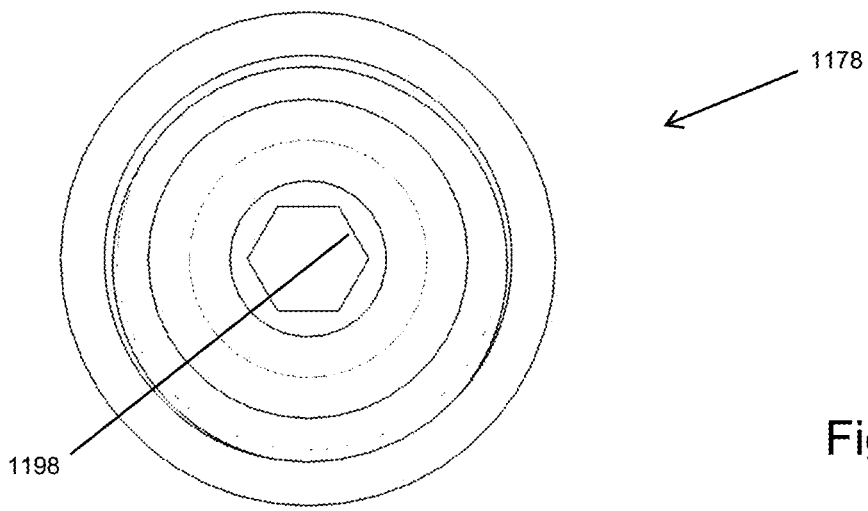
FIG. 80B is a top view of the compression collar in accordance with exemplary embodiments of the present technology.
Figure 80C:
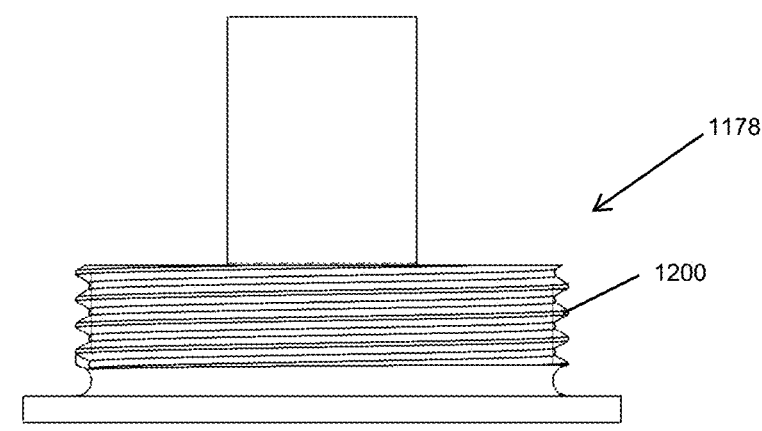
FIG. 80C is a side view of the compression collar in accordance with exemplary embodiments of the present technology.

In various embodiments, shown in FIGS. 78A-C, the retention ring 1182 may contain threads 1188 which are received within internal threads 1190 located in an internal wall 1192 in the cylindrical collar 1124 of the mating post 1122. The plug 1184, shown in FIGS. 79A-C may be received within the internal wall 1192 in the cylindrical collar 1124 and comprises internal threads 1194, which receive the retention connector 1186, and a mating collar 1196.

The retention connector 1186 is used in conjunction with the compression cap 1178 and is received within the internal threads 1194 in the plug 1184. When tightened, the retention connector 1186 seats the mating collar 1196 within the mating recess 1198 in the compression cap 1178. In one embodiment, the retention connector 1186 is a screw.

In various embodiments, referring now to FIGS. 76 and 80A-C the retention system 1180 may comprise the compression cap 1178. The compression cap 1178 carries some of the vertical load imparted to the upper member 1102 through the vertical spring 1176 and the retention system 1180 to the lower member 1104. The compression cap 1178 may be press fit or may contain threads 1200 that mate with internal threads 1202 in the lower collar 1146 of the mating portion 1140. The compression cap 1178 may be used in conjunction with the mating post 1122, which is received within the sleeve 1132, to couple the upper member 1102 to the lower member 1104. The sleeve 1132 may comprise a low-friction material that facilitates smooth movement between the upper and lower members 1102, 1104.

In use, the cylindrical collar 1124 of the mating post 1122 is received within the sleeve 1132, which is received in the upper and lower collars 1144, 1146 of the mating portion 1140 when the upper and lower members 1102, 1104 are connected.

The compression cap 1178 also keeps dirt, sand, or small objects from entering the mating portion 1140 of the lower member 1104. Objects such as small rocks or sand could wear away the moving internal members eventually causing damage or failure.

The sleeve 1132 is similar to the sleeve 910 discussed above in FIG. 25. The sleeve 1132 may comprise a cylindrical wall and first and second ends. The sleeve 1132 fits within the mating portion 1140 of the lower member 1104. The sleeve 1132 may be inserted at a lower end of the lower member 1104 and may extend along the length of the mating portion 1140. The first end of the sleeve 1132 may abut a lip formed in the interior of the upper collar 1044 of the lower member 1104. The lip is configured to retain the first end within the mating portion 1140.

The sleeve 1132 may be made from any suitable low-friction material. In one embodiment the low friction sleeve is made from plastic to allow for smooth movement between the components of the prosthetic foot. In one embodiment a low coefficient plastic bushing material may be used.

In use under load, the vertical spring 1176 and the elastomeric ring 1158 in conjunction with the internal bumper 1164 provide a limited amount of vertical movement of the upper member 1102 with respect to the lower member 1104. The internal bumper 1164, the elastomeric ring 1158, and the vertical spring 1176 limit vertical movement while the torsion limiter 1056 limits the torsional movement. The elastomeric ring 1158 provides vertical shock absorption and torsional stability during the gate cycle and while standing. The vertical spring 1176 provides vertical shock absorption and compression when in use.

The mounting bracket 1100 provides a multi-phase system. When the initial load is applied to the prosthetic foot 100, the elastomeric ring 1158 provides both a soft resistance for vertical compression and torsional rotation. Under compression, the elastomeric ring 1158 and the vertical spring 1176 simultaneously provide resistance. The elastomeric ring 1158 carries a large portion of the compressive load relative to the vertical spring 1176. Once a larger load is applied, the vertical spring 1176 is compressed between the plug 1084 located within the cylindrical collar 1124 and the compression cap 1178, thereby only allowing a limited amount of vertical movement of the upper member 1102 with respect to the lower member 1104. This is in concert with the internal bumper 1164, which encapsulates ears 1152 and 1154 of upper member 1102, contacting upper collar 1144 of lower member 1104.

According to various embodiments and referring to FIG. 57 the upper and lower members 1102, 1104 may be coupled by the elastomeric ring 1158. The elastomeric ring 1158 may comprise any rubber, polyurethane, and/or elastomeric materials. The elastomeric ring 1158 may be bonded to the upper and lower members 1102, 1104 using an adhesive. The upper surface of the elastomeric ring 1158 may be received in and bonded within the channel 1120 in the upper flange 1110 in the upper member 1102. The lower surface of the elastomeric ring 1158 may be received in and bonded within the channel 1148 in the lower flange 1138 in the lower member 1104. The elastomeric ring 1158 may act as a shock for absorbing force on the downward strike during the user's stride.

In various embodiments, the elastomeric ring 1158 may comprise an adhesive bonding and thus coupling the lower member to the upper member. Further, the adhesive bonding of the elastomeric ring 1158 may produce distributed stresses. Though other modulus values are contemplated, and various moduli may be used as well, a stiffer adhesive is preferred compared to a flexible adhesive. The elastomeric ring 1158 creates a space between the upper flange 1110 of the upper member 1102 and the lower flange 1138 of the lower member 1104. The adhesive may be commingled with the elastomeric ring 1158.

The prosthetic foot 100 can be adjusted to accommodate a user in part by adjusting characteristics of the elastomeric ring 1158 between the upper member 1102 and lower member 1104. For example, in various embodiments, the durometer of the elastomeric ring 1158 can be increased for users with more heel strike force, which may be caused by additional weight or dynamic activity.

In various embodiments and as shown the elastomeric ring 1158, internal bumper 1164, and the vertical spring 1176 may comprise an elastomeric material. The elastomeric material may comprise a general elastomeric material, polyurethane, natural rubber, a synthetic rubber, or various combinations of natural and synthetic rubber, plastic, metal and the like. The durometer of the elastomeric material of both the elastomeric ring 1158, the internal bumper 1164, and the vertical spring 1176 may be varied to provide additional adjustment of the prosthetic foot. The elastomeric material of the elastomeric ring 1158, the internal bumper 1164, and the vertical spring 1176 supports load. Further, since the elastomeric ring 1158 couples the upper and lower members 1102, 1104, the members are capable of torsional rotation during use of the prosthetic foot 100. The adjustable durometer of the elastomeric material allows the adjustment of the spring rate of the elastomeric ring based on user needs such as activity level, compliance level, weight changes, and the like. For example, in various embodiments, the durometer of the elastomeric material can be increased for users with more heel strike force, which may be caused by additional weight of the user or dynamic activity of the user. Increased heel strike force also provides greater compression of the heel member. As stated above the elastomeric ring 1158 and the vertical spring 1176 may comprise a lower durometer than the internal bumper 1164 thereby providing an initial soft resistance to vertical load and torsional rotation. The higher durometer internal bumper 1164 provides a greater resistance during high torsional loads.

The depending ears 1152 and 1154 of the upper member 1102, and the depending ears 1160 and 1162 of the lower member 1104, when assembled with the internal bumper 1164 serve to limit rotation of the upper member 1102 with respect to the lower member 1104 during use as will be discussed in detail below.

In various embodiments, the depending ears 1152 and 1154 of the upper member 1102, and the depending ears 1160 and 1162 of the lower member 1104 may be activated when the upper member 1102 of the mounting bracket 1100 rotates enough to overcome the torsional stiffness of the elastomeric ring 1158 and allow depending ears 1152 and 1154 of the upper member 1102, and the depending ears 1160 and 1162 of the lower member 1104 to contact one another. The depending ears 1152 and 1154 of the upper member 1102, and the depending ears 1160 and 1162 of the lower member 1104 engage with each other at the same angle of rotation regardless of the amount of vertical compression experienced by the mounting bracket 1100.

Figure 59:
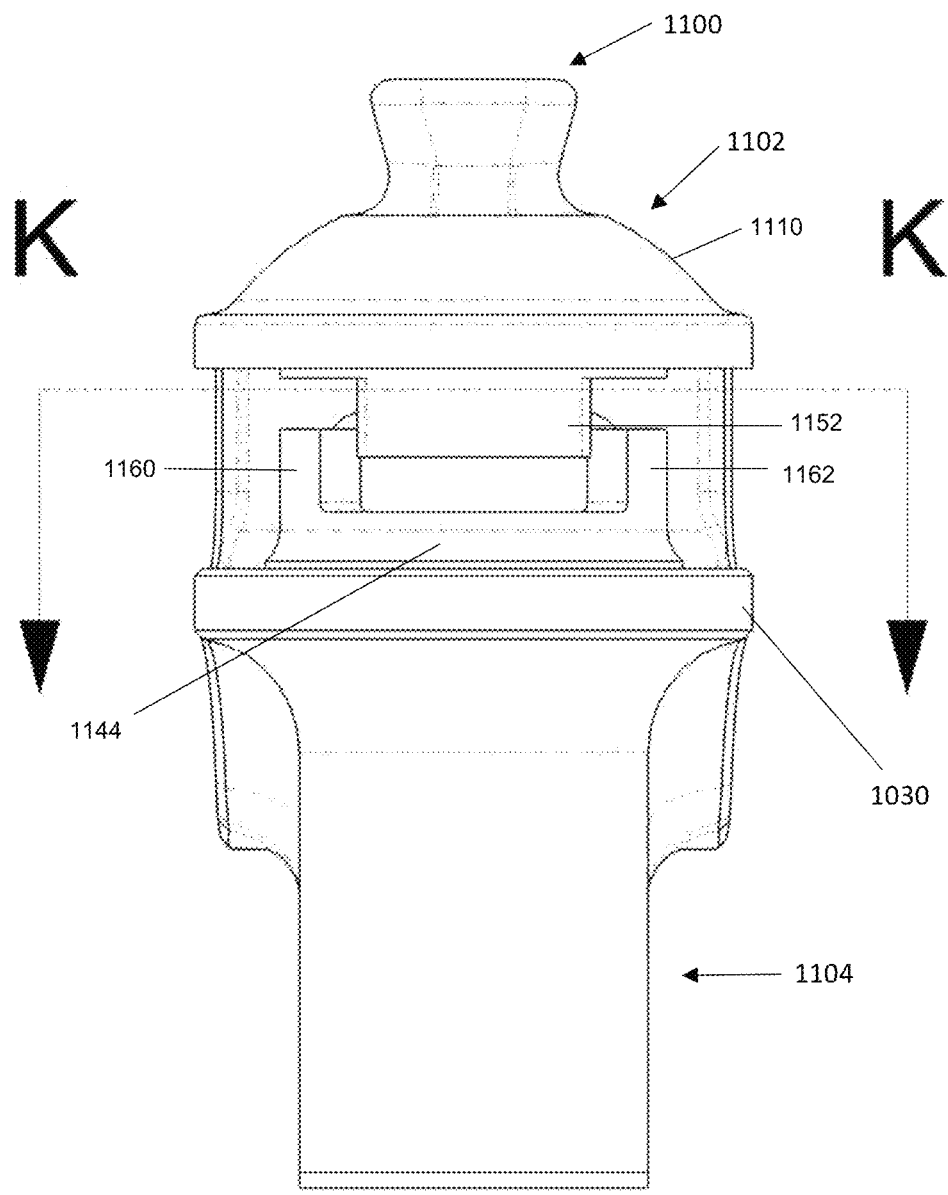
FIG. 59 is a front view of the mounting bracket showing upper and lower members and with the elastomeric ring removed.
Figure 60:
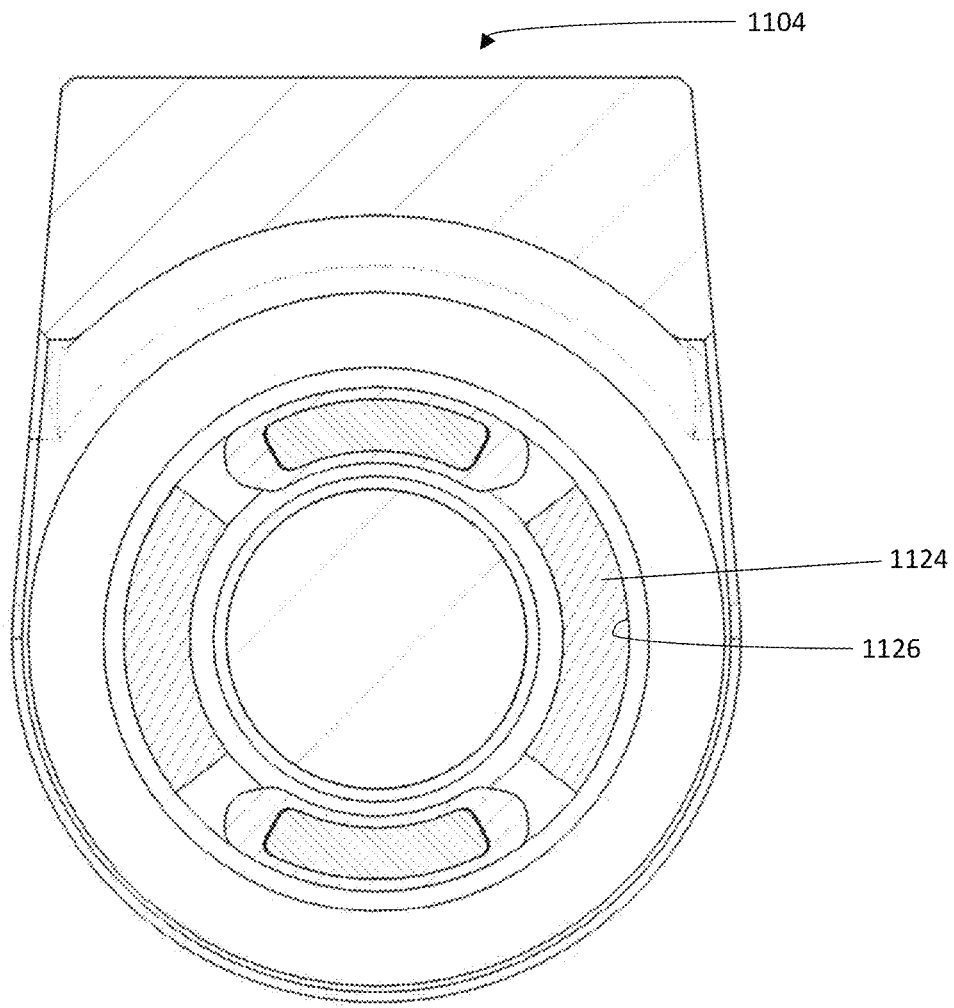
FIG. 60 is a top, cross-section view taken along the line K-K in FIG. 59 representatively illustrating portions of the mounting bracket in accordance with exemplary embodiments of the present technology.

FIG. 59 shows the gap between the depending ears 1152 and 1154 of the upper member 1102, and the depending ears 1160 and 1162 of the lower member 1104 and how the ears will act as stops when rotated until they contact each other. The depending ears 1152 and 1154 of the upper member 1102 are surrounded by the internal bumper 1164 to soften the end of rotational travel. See FIG. 75. The depending ears 1160 and 1162 of the lower member 1104 contact the lower surface 1118 of upper member 1102 at the end of vertical travel regardless of the amount of torsional travel. The depending ears 1152 and 1154 of the upper member 1102 contact the upper collar 1044 at the end of vertical travel regardless of the amount of torsional travel. In one embodiment the depending ears 1160 and 1162 of the lower member 1104 may restrict the amount of vertical travel simultaneously with the depending ears 1152 and 1154 of the upper member 1102. In another embodiment the depending ears 1160 and 1162 of the lower member 1104 may restrict the amount of vertical travel exclusively. In another embodiment the depending ears 1152 and 1154 of the upper member 1102 may restrict the amount of vertical travel exclusively.

According to various embodiments the upper and lower members 1102, 1104 may be made from Titanium (any type) or any other suitable material. In one embodiment the upper member 1102 may comprise titanium. In one embodiment the lower member 1104 may comprise alloy aluminum. Some other types of material that may be used for the upper and lower members 1102, 1104 comprise mild steel, alloy steel, steel, high strength stainless steel such as 13-8, alloy aluminum such as the 2000 and 7000 series, and any suitable composite material.

In various embodiments, the upper and lower members 1102, 1104 described above can be an integral piece or multiple pieces joined together by any suitable method. In some embodiments, depending on the type of material, the upper and lower members 1102, 1104 may be fabricated by milling, casting, forging, powdered metal, and the like. In one embodiment, the upper and lower members 1002, 1004 may be fabricated on a titanium CNC milling machine. More specifically, in one embodiment the upper and lower members 1102, 1104 may be unitary made from alloy aluminum fabricated using a CNC milling machine. In other embodiments, the aluminum, titanium, magnesium or other suitable material for the upper and lower members 1102, 1104 may be fabricated using a CNC milling machine. In other embodiments, the aluminum, titanium, magnesium or other suitable for the upper and lower members 1102, 1104 may be fabricated by casting, forging, powdered metal, and the like. In other embodiments, a chrome moly, steel, or other suitable material for the upper and lower members 1102, 1104 can be made from multiple pieces and coupled together by welding or any other suitable method.

The technology has been described with reference to specific exemplary embodiments. Various modifications and changes, however, may be made without departing from the scope of the present technology. The description and figures are to be regarded in an illustrative manner, rather than a restrictive one and all such modifications are intended to be included within the scope of the present technology. Accordingly, the scope of the technology should be determined by the generic embodiments described and their legal equivalents rather than by merely the specific examples described above. For example, the steps recited in any method or process embodiment may be executed in any order, unless otherwise expressly specified, and are not limited to the explicit order presented in the specific examples. Additionally, the components and/or elements recited in any apparatus embodiment may be assembled or otherwise operationally configured in a variety of permutations to produce substantially the same result as the present technology and are accordingly not limited to the specific configuration recited in the specific examples.

Benefits, other advantages and solutions to problems have been described above with regard to particular embodiments; however, any benefit, advantage, solution to problems or any element that may cause any particular benefit, advantage or solution to occur or to become more pronounced are not to be construed as critical, required or essential features or components.

As used herein, the terms "comprises", "comprising", or any variation thereof, are intended to reference a non-exclusive inclusion, such that a process, method, article, composition or apparatus that comprises a list of elements does not include only those elements recited, but may also include other elements not expressly listed or inherent to such process, method, article, composition or apparatus. Other combinations and/or modifications of the above-described structures, arrangements, applications, proportions, elements, materials or components used in the practice of the present technology, in addition to those not specifically recited, may be varied or otherwise particularly adapted to specific environments, manufacturing specifications, design parameters or other operating requirements without departing from the general principles of the same.

The present technology has been described above with reference to a preferred embodiment. However, changes and modifications may be made to the preferred embodiment without departing from the scope of the present technology. These and other changes or modifications are intended to be included within the scope of the present technology, as expressed in the following claims.

What is claimed:

1. A mounting bracket for attaching a prosthetic foot to a residual limb, comprising:
    an upper member comprising an upper flange, a mating post, and mounting portion configured to attach to the residual limb;
    a lower member comprising a mating portion, a lower flange, and a mounting portion configured to attach to the prosthetic foot;
    a compression torsion joint coupling the upper member to the lower member and configured to limit vertical movement and torsional movement of the upper member with respect to the lower member; and
    a retention system comprising:
        a compression cap coupled to the mating portion of the lower member;
        a collar coupled within a lower end of the mating post of the upper member;
        a plug located above the collar;
        a connector received within a lower end of the compression cap and coupled to the plug.

2. The mounting bracket of claim 1, wherein the mating post of the upper member is received within the mating portion of the lower member.

3. The mounting bracket of claim 1, wherein the upper flange and lower flange each comprise a channel adjacent to a perimeter of the upper flange and lower flange.

4. The mounting bracket of claim 3, wherein the compression torsion joint comprises an elastomeric ring configured to limit the vertical movement and the torsional movement of the upper member with respect to the lower member.

5. The mounting bracket of claim 1, wherein the compression torsion joint is not located outwardly of a perimeter of the upper flange and the lower flange.

6. The mounting bracket of claim 4, wherein an upper surface of the elastomeric ring is received within the channel in the upper flange and a lower surface of the elastomeric ring is received in the channel in the lower flange.

7. The mounting bracket of claim 4, wherein the compression torsion joint comprises a vertical spring configured to limit the vertical movement.

8. The mounting bracket of claim 6, wherein the upper surface of the elastomeric ring is coupled to the channel in the upper flange and the lower surface of the elastomeric ring is coupled to the channel in the lower flange.

9. The mounting bracket of claim 8, wherein the upper member comprises a pair of ears depending downwardly from a lower surface of the upper flange, and the lower member comprises a pair of ears depending upwardly from an upper collar of the lower flange.

10. The mounting bracket of claim 9, wherein the pair of ears depending from the upper flange are located opposite one another inwardly of an interior perimeter of the channel.

11. The mounting bracket of claim 10, wherein the pair of ears depending from the upper collar are located opposite one another inwardly of an interior perimeter of the channel.

12. The mounting bracket of claim 11, wherein the pair of ears on the upper flange and lower flange are configured to restrict the torsional movement of the upper member with respect to the lower member.

13. The mounting bracket of claim 10, wherein the compression torsion joint comprises an internal bumper coupled to the pair of ears depending from of the upper collar.

14. The mounting bracket of claim 13, wherein the internal bumper comprises a pair of recesses that receive the pair of ears depending from the upper collar.

15. The mounting bracket of claim 10, wherein the pair of ears of the upper and lower members are located between and surrounded by the upper member, lower member, and the elastomeric ring.

16. A mounting bracket for attaching a prosthetic foot to a residual limb, comprising:
   an upper member comprising:
      an upper flange with a channel;
      a mating post;
      a pair of ears depending downwardly from a lower surface of the upper flange and located inwardly of an inner perimeter of the channel; and
      a mounting portion configured to attach to the residual limb;
   a lower member comprising:
      a lower flange with a channel;
      a mating portion configured to receive the mating post;
      a pair of ears depending upwardly from an upper collar of the lower flange and located inwardly of the channel; and
      a mounting portion configured to attach to the prosthetic foot;
   a compression torsion joint coupling the upper member to the lower member and configured to limit vertical movement and torsional movement of the upper member with respect to the lower member, comprising an elastomeric ring having an upper surface coupled to the channel of the upper flange and a lower surface coupled to the channel of the lower flange; and
   a retention system comprising:
      a compression cap coupled to the mating portion of the lower member;
      a collar coupled within a lower end of the mating post of the upper member;
      a plug located above the collar; and
      a connector received within a lower end of the compression cap and coupled to the plug.

17. The mounting bracket of claim 16, wherein the compression torsion joint is not located outwardly of a perimeter of the upper flange and the lower flange.

18. The mounting bracket of claim 17, wherein the pair of ears of the upper and lower members are located between and surrounded by the upper member, lower member, and the elastomeric ring.

19. A prosthetic foot for use within a foot shell and configured to attach to a residual limb, comprising:
   a resilient bottom member comprising a front end, a rear end, and having no inflection point, wherein a center point of a radius of curvature of the front end of the resilient bottom member is above the bottom member and the rear end of the resilient bottom member is straight;
   a resilient top member comprising a front end and a rear end, wherein the front end of the resilient top member is connected to the front end of the resilient bottom member, and wherein the resilient top member is positioned over the resilient bottom member;
   a bumper member attached to an underside of the rear end of the resilient top member; and
   a mounting bracket coupled to the resilient top member, the mounting bracket comprising:
      an upper member comprising:
         an upper flange with a channel;
         a mating post;
         a pair of ears depending downwardly from a lower surface of the upper flange and located inwardly of an inner perimeter of the channel; and
         a mounting portion configured to attach to the residual limb;
      a lower member comprising:
         a lower flange with a channel;
         a mating portion configured to receive the mating post;
         a pair of ears depending upwardly from an upper collar of the lower flange and located inwardly of the channel; and
         a mounting portion configured to attach to the prosthetic foot;
      a compression torsion joint coupling the upper member to the lower member and configured to limit vertical movement and torsional movement of the upper member with respect to the lower member, comprising an elastomeric ring having an upper surface coupled to the channel of the upper flange and a lower surface coupled to the channel of the lower flange; and
      a retention system comprising:
         a compression cap coupled to the mating portion of the lower member;
         a collar coupled within a lower end of the mating post of the upper member;
         a plug located above the collar; and
         a connector received within a lower end of the compression cap and coupled to the plug.

* * * * *